(12) United States Patent
Bowers et al.

(10) Patent No.: US 12,031,985 B2
(45) Date of Patent: Jul. 9, 2024

(54) DETECTION OF TARGETS

(71) Applicant: First Light Biosciences, Inc., Chelmsford, MA (US)

(72) Inventors: Jayson L. Bowers, Cambridge, MA (US); Michael Cappillino, Haverhill, MA (US); Sadanand Gite, Arlington, MA (US); Don Straus, Charlestown, MA (US)

(73) Assignee: FIRST LIGHT DIAGNOSTICS, INC., Chelmsford, MA (US)

( * ) Notice: Subject to any disclaimer, the term of this patent is extended or adjusted under 35 U.S.C. 154(b) by 743 days.

(21) Appl. No.: 16/389,852

(22) Filed: Apr. 19, 2019

(65) Prior Publication Data

US 2019/0324034 A1    Oct. 24, 2019

Related U.S. Application Data

(60) Provisional application No. 62/660,075, filed on Apr. 19, 2018, provisional application No. 62/711,784, filed on Jul. 30, 2018.

(51) Int. Cl.
*G01N 33/569* (2006.01)
*B01L 3/00* (2006.01)
(Continued)

(52) U.S. Cl.
CPC ...... *G01N 33/56911* (2013.01); *B01L 3/5025* (2013.01); *G01N 21/6428* (2013.01);
(Continued)

(58) Field of Classification Search
CPC ......... G01N 33/56911; G01N 21/6428; G01N 33/5302; G01N 33/54326; G01N 33/582;
(Continued)

(56) References Cited

U.S. PATENT DOCUMENTS 2,672,431 A    3/1954  Goetz
2,761,813 A    9/1956  Goetz
(Continued)

FOREIGN PATENT DOCUMENTS

AU    760425 B2    5/2003
CN    2486557 Y    4/2002
(Continued)

OTHER PUBLICATIONS

Al-Hakiem, 1982, Development of Fluoroimmunoassays for the Determination of Individual or Combined Levels of Procainamide and N-Acetylprocainamide in Serum, J Immunoassay 3(1):91-110.
(Continued)

*Primary Examiner* — Christopher L Chin
(74) *Attorney, Agent, or Firm* — BALLARD SPAHR LLP

(57) ABSTRACT

Methods and cartridges for detecting targets are provided. A biological sample is introduced to a cartridge. Targets in the sample are photonically labeled with fluorescent particles in a first liquid layer in the cassette. Photonically-labeled targets are separated out of the sample into a second liquid layer within the cassette, detected, and counted to show presence of the targets in the subject. Cartridges include a receiving reservoir, a mixing well for introducing the sample to photonic labels and magnetic particles, and an imaging well for detecting and counting targets from the sample. The sample may be a human stool sample. A filter may be used to filter particulates out of the sample.

25 Claims, 43 Drawing Sheets

(51) Int. Cl.
  *G01N 21/64*  (2006.01)
  *G01N 33/53*  (2006.01)
  *G01N 33/543*  (2006.01)
  *G01N 33/58*  (2006.01)

(52) U.S. Cl.
  CPC ... *G01N 33/5302* (2013.01); *G01N 33/54326* (2013.01); *G01N 33/582* (2013.01); *B01L 2300/0681* (2013.01); *B01L 2400/043* (2013.01); *G01N 2021/6439* (2013.01); *G01N 2469/10* (2013.01); *G01N 2800/26* (2013.01)

(58) Field of Classification Search
  CPC ....... G01N 2021/6439; G01N 2469/10; G01N 2800/26; G01N 15/1463; G01N 33/54366; G01N 2015/1006; G01N 2015/1486; G01N 21/645; B01L 3/5025; B01L 2300/0681; B01L 2400/043; B01L 2200/0647; B01L 3/502
  USPC ............ 422/554, 82.08; 435/6.1, 6.19, 7.32; 436/172, 526, 537, 538, 541
  See application file for complete search history.

(56) References Cited

U.S. PATENT DOCUMENTS

| | | |
|---|---|---|
| 3,694,317 A | 9/1972 | Scher |
| 3,981,776 A | 9/1976 | Saxholm |
| 4,097,586 A | 6/1978 | Gross |
| 4,098,876 A | 7/1978 | Piasio et al. |
| 4,115,535 A | 9/1978 | Giaever |
| 4,125,375 A | 11/1978 | Hunter |
| 4,129,419 A | 12/1978 | Hermann, Jr. |
| 4,141,687 A | 2/1979 | Forrest et al. |
| 4,157,323 A | 6/1979 | Yen et al. |
| 4,177,253 A | 12/1979 | Davies et al. |
| 4,222,744 A | 9/1980 | McConnell |
| 4,436,826 A | 3/1984 | Wang |
| 4,438,068 A | 3/1984 | Forrest |
| 4,454,233 A | 6/1984 | Wang |
| 4,455,370 A | 6/1984 | Bartelsman et al. |
| 4,477,578 A | 10/1984 | Miles et al. |
| 4,537,861 A | 8/1985 | Elings et al. |
| 4,562,157 A | 12/1985 | Lowe et al. |
| 4,565,783 A | 1/1986 | Hansen et al. |
| 4,582,810 A | 4/1986 | Rosenstein |
| 4,587,213 A | 5/1986 | Malecki |
| 4,614,585 A | 9/1986 | Mehra et al. |
| 4,693,972 A | 9/1987 | Mansour et al. |
| 4,731,337 A | 3/1988 | Luotola et al. |
| 4,745,077 A | 5/1988 | Holian et al. |
| 4,750,820 A | 6/1988 | Pareigat |
| 4,777,137 A | 10/1988 | Lemonnier |
| 4,777,145 A | 10/1988 | Luotola et al. |
| 4,912,037 A | 3/1990 | Lemonnier |
| 4,922,092 A | 5/1990 | Rushbrooke et al. |
| 4,959,301 A | 9/1990 | Weaver et al. |
| 4,981,783 A | 1/1991 | Augenlicht |
| 4,988,302 A | 1/1991 | Smith et al. |
| 4,988,618 A | 1/1991 | Li et al. |
| 5,073,497 A | 12/1991 | Schwartz |
| 5,089,413 A | 2/1992 | Nelson et al. |
| 5,130,733 A | 7/1992 | Taniguchi et al. |
| 5,137,812 A | 8/1992 | Matner |
| 5,190,666 A | 3/1993 | Bisconte |
| 5,232,838 A | 8/1993 | Nelson et al. |
| 5,238,810 A | 8/1993 | Fujiwara et al. |
| 5,258,284 A | 11/1993 | Morris, Jr. et al. |
| 5,262,526 A | 11/1993 | Sasamoto et al. |
| 5,292,644 A | 3/1994 | Berg |
| 5,306,420 A | 4/1994 | Bisconte |
| 5,321,545 A | 6/1994 | Bisconte |
| 5,348,885 A | 9/1994 | Labarthe |
| 5,355,215 A | 10/1994 | Schroeder et al. |
| 5,366,867 A | 11/1994 | Kawakami et al. |
| 5,464,749 A | 11/1995 | Schwarzberg et al. |
| 5,474,910 A | 12/1995 | Alfano |
| 5,510,246 A | 4/1996 | Morgan |
| 5,538,857 A | 7/1996 | Rosenthal et al. |
| 5,541,069 A | 7/1996 | Mortensen et al. |
| 5,552,272 A | 9/1996 | Bogart |
| 5,558,839 A | 9/1996 | Matte et al. |
| 5,582,982 A | 12/1996 | Cubbage et al. |
| 5,585,241 A | 12/1996 | Lindmo |
| 5,604,351 A | 2/1997 | Bisconte |
| 5,606,413 A | 2/1997 | Bellus et al. |
| 5,624,850 A | 4/1997 | Kumar et al. |
| 5,648,274 A | 7/1997 | Chandler |
| 5,652,939 A | 7/1997 | Verlinden et al. |
| 5,653,939 A | 8/1997 | Hollis et al. |
| 5,663,057 A | 9/1997 | Drocourt et al. |
| 5,672,880 A | 9/1997 | Kain |
| 5,681,530 A | 10/1997 | Kuster et al. |
| 5,681,712 A | 10/1997 | Nelson |
| 5,694,478 A | 12/1997 | Braier et al. |
| 5,705,402 A | 1/1998 | Leland et al. |
| 5,736,405 A | 4/1998 | Alfano et al. |
| 5,744,322 A | 4/1998 | Krejcarek et al. |
| 5,766,868 A | 6/1998 | Seto |
| 5,792,617 A | 8/1998 | Rotman |
| 5,814,454 A | 9/1998 | Ju |
| 5,821,066 A | 10/1998 | Pyle et al. |
| 5,828,716 A | 10/1998 | Bisconte de Saint Julien |
| 5,852,498 A | 12/1998 | Youvan et al. |
| 5,861,251 A | 1/1999 | Park et al. |
| 5,861,270 A | 1/1999 | Nelis |
| 5,861,306 A | 1/1999 | Pugh et al. |
| 5,891,394 A | 4/1999 | Drocourt et al. |
| 5,914,245 A | 6/1999 | Bylina et al. |
| 5,958,790 A | 9/1999 | Cerny |
| 5,968,766 A | 10/1999 | Powers |
| 5,976,892 A | 11/1999 | Bisconte |
| 5,981,180 A | 11/1999 | Chandler et al. |
| 5,985,675 A | 11/1999 | Charm et al. |
| 5,989,835 A | 11/1999 | Dunlay et al. |
| 5,993,740 A | 11/1999 | Niiyama et al. |
| 6,048,723 A | 4/2000 | Banes |
| 6,051,393 A | 4/2000 | Jones et al. |
| 6,051,395 A | 4/2000 | Rocco |
| 6,121,055 A | 9/2000 | Hargreaves |
| 6,122,396 A | 9/2000 | King et al. |
| 6,130,931 A | 10/2000 | Laurila et al. |
| 6,140,653 A | 10/2000 | Che |
| 6,165,742 A | 12/2000 | Øfjord et al. |
| 6,171,780 B1 | 1/2001 | Pham et al. |
| 6,200,762 B1 | 3/2001 | Zlokarnik et al. |
| 6,214,560 B1 | 4/2001 | Yguerabide et al. |
| 6,258,326 B1 | 7/2001 | Modlin |
| 6,259,807 B1 | 7/2001 | Ravkin |
| 6,268,222 B1 | 7/2001 | Chandler et al. |
| 6,274,384 B1 | 8/2001 | Starzl et al. |
| 6,287,849 B1 | 9/2001 | McNerney et al. |
| 6,306,589 B1 | 10/2001 | Muller et al. |
| 6,309,822 B1 | 10/2001 | Fodor et al. |
| 6,345,115 B1 | 2/2002 | Ramm et al. |
| 6,358,730 B1 | 3/2002 | Kane |
| 6,472,166 B1 | 10/2002 | Wardlaw et al. |
| 6,582,912 B1 | 6/2003 | Rousseau et al. |
| 6,602,704 B1 | 8/2003 | Maxwell et al. |
| 6,623,983 B1 | 9/2003 | Terstappen et al. |
| 6,649,418 B1 | 11/2003 | Geisberg |
| 6,664,528 B1 | 12/2003 | Cartlidge et al. |
| 6,710,879 B1 | 3/2004 | Hansen et al. |
| 6,727,071 B1 | 4/2004 | Dunlay et al. |
| 6,764,648 B1 | 7/2004 | Roach et al. |
| 6,790,655 B2 | 9/2004 | Lyman et al. |
| 6,792,132 B1 | 9/2004 | Hara et al. |
| 6,852,527 B2 | 2/2005 | Chan et al. |
| 6,919,960 B2 | 7/2005 | Hansen et al. |
| 6,969,607 B2 | 11/2005 | Minton |
| 7,068,365 B2 | 6/2006 | Hansen et al. |
| 7,110,585 B2 | 9/2006 | Cork et al. |
| 7,160,687 B1 | 1/2007 | Kapur et al. |

(56) References Cited

U.S. PATENT DOCUMENTS

| | | |
|---|---|---|
| 7,582,415 B2 | 9/2009 | Straus |
| 7,763,405 B2 | 7/2010 | Wu et al. |
| 7,763,455 B2 | 7/2010 | Cima et al. |
| 7,820,430 B2 | 10/2010 | Weng et al. |
| 8,021,848 B2 | 9/2011 | Straus |
| 9,090,462 B2 | 7/2015 | Straus |
| 9,290,382 B2 | 3/2016 | Straus |
| 9,632,085 B2 | 4/2017 | Super et al. |
| 9,643,180 B2 | 5/2017 | Abrams et al. |
| 2001/0039032 A1 | 11/2001 | Matsumura et al. |
| 2001/0039060 A1 | 11/2001 | Siiman et al. |
| 2002/0028471 A1 | 3/2002 | Oberhardt |
| 2002/0055092 A1 | 5/2002 | Hochman |
| 2002/0137106 A1 | 9/2002 | Leung et al. |
| 2003/0036058 A1 | 2/2003 | Becker et al. |
| 2003/0068638 A1 | 4/2003 | Cork et al. |
| 2003/0082516 A1 | 5/2003 | Straus |
| 2003/0124532 A1 | 7/2003 | Powers et al. |
| 2003/0143580 A1 | 7/2003 | Straus |
| 2003/0170613 A1 | 9/2003 | Straus |
| 2004/0048395 A1 | 3/2004 | Lee et al. |
| 2004/0171121 A1 | 9/2004 | Leppla et al. |
| 2004/0172000 A1 | 9/2004 | Roe et al. |
| 2004/0246483 A1 | 12/2004 | Hansen et al. |
| 2005/0013737 A1 | 1/2005 | Chow et al. |
| 2005/0053942 A1 | 3/2005 | Kauppinen et al. |
| 2005/0148085 A1 | 7/2005 | Larsen |
| 2005/0152955 A1 | 7/2005 | Akhave et al. |
| 2005/0153430 A1 | 7/2005 | Ohtaka |
| 2005/0191687 A1 | 9/2005 | Wang et al. |
| 2005/0220670 A1 | 10/2005 | Palmieri et al. |
| 2005/0221403 A1 | 10/2005 | Gazenko |
| 2005/0225766 A1 | 10/2005 | Hansen et al. |
| 2005/0226779 A1 | 10/2005 | Oldham et al. |
| 2006/0006067 A1 | 1/2006 | Unger |
| 2006/0046246 A1 | 3/2006 | Zeng et al. |
| 2006/0051816 A1 | 3/2006 | Hsieh et al. |
| 2006/0121055 A1 | 6/2006 | Campbell et al. |
| 2006/0129327 A1 | 6/2006 | Kim et al. |
| 2006/0188967 A1 | 8/2006 | Nalin et al. |
| 2006/0210435 A1 | 9/2006 | Alavie et al. |
| 2006/0216696 A1 | 9/2006 | Goguen |
| 2006/0256340 A1 | 11/2006 | Hansen et al. |
| 2006/0292552 A1 | 12/2006 | Haquette et al. |
| 2007/0014695 A1 | 1/2007 | Yue et al. |
| 2007/0172899 A1 | 7/2007 | Graham et al. |
| 2007/0184546 A1 | 8/2007 | Farrelly et al. |
| 2007/0202681 A1 | 8/2007 | Wang |
| 2007/0212681 A1 | 9/2007 | Shapiro et al. |
| 2007/0212747 A1 | 9/2007 | Browne et al. |
| 2008/0003571 A1 | 1/2008 | McKernan et al. |
| 2008/0014576 A1 | 1/2008 | Jovanovich et al. |
| 2008/0032328 A1 | 2/2008 | Cline et al. |
| 2008/0038738 A1 | 2/2008 | Weigum et al. |
| 2008/0200343 A1 | 8/2008 | Clemens et al. |
| 2008/0206099 A1 | 8/2008 | Aruga et al. |
| 2009/0075274 A1 | 3/2009 | Slepnev et al. |
| 2009/0137029 A1 | 5/2009 | Breidenthal et al. |
| 2009/0315987 A1 | 12/2009 | Straus |
| 2010/0028986 A1 | 2/2010 | Hanafusa |
| 2010/0248281 A1 | 9/2010 | Straus |
| 2011/0028563 A1 | 2/2011 | Found |
| 2012/0045826 A1 | 2/2012 | Yantz et al. |
| 2012/0046203 A1 | 2/2012 | Walsh et al. |
| 2012/0149007 A1 | 6/2012 | Abrams et al. |
| 2013/0011566 A1 | 1/2013 | Colin et al. |
| 2013/0216454 A1 | 8/2013 | Blecka et al. |
| 2015/0152467 A1 | 6/2015 | Ingber et al. |
| 2016/0084828 A1 | 3/2016 | Coy |
| 2016/0152694 A1 | 6/2016 | Ambrosino et al. |
| 2016/0289729 A1 | 10/2016 | Richards et al. |
| 2017/0029864 A1 | 2/2017 | Straus |
| 2018/0088141 A1 | 3/2018 | Vacic et al. |
| 2019/0324034 A1 | 10/2019 | Bowers et al. |
| 2019/0366338 A1 | 12/2019 | Yantz et al. |

FOREIGN PATENT DOCUMENTS

| | | |
|---|---|---|
| CN | 101254482 A | 9/2008 |
| DE | 19608320 A1 | 8/1997 |
| DE | 19631997 A1 | 2/1998 |
| DE | 19940810 A1 | 5/2000 |
| EP | 0171174 A2 | 2/1986 |
| EP | 0574977 A1 | 12/1993 |
| EP | 0753732 A2 | 1/1997 |
| EP | 1207394 A2 | 5/2002 |
| EP | 1508374 A2 | 2/2005 |
| JP | S62-501647 A | 7/1987 |
| JP | H02-502405 A | 8/1990 |
| JP | H02-278155 A | 11/1990 |
| JP | H3-83598 | 4/1991 |
| JP | H08-201391 A | 8/1996 |
| JP | 10295362 | 11/1998 |
| JP | H11-148901 A | 6/1999 |
| JP | H11-346795 A | 12/1999 |
| JP | 2000-508778 A | 7/2000 |
| JP | 2000-509827 A | 8/2000 |
| JP | 2000-275258 A | 10/2000 |
| JP | 3102240 B2 | 10/2000 |
| JP | 2001-224355 A | 8/2001 |
| JP | 2001-512875 A | 8/2001 |
| JP | 2002-125656 A | 5/2002 |
| JP | 2003-294596 A | 10/2003 |
| JP | 2004-070039 A | 3/2004 |
| JP | 2004-125799 A | 4/2004 |
| JP | 2005-502354 A | 1/2005 |
| JP | 2006-087336 A | 4/2006 |
| JP | 2006-162466 A | 6/2006 |
| JP | 2007-526807 A | 9/2007 |
| JP | 2008-96223 A | 4/2008 |
| JP | 2008-513022 A | 5/2008 |
| JP | 2009-513111 A | 4/2009 |
| WO | 83/01581 A1 | 5/1983 |
| WO | 86/04684 A1 | 8/1986 |
| WO | 89/05456 A1 | 6/1989 |
| WO | 92/05448 A2 | 4/1992 |
| WO | 97/40181 A1 | 10/1997 |
| WO | 9744664 A1 | 11/1997 |
| WO | 98/38490 A1 | 9/1998 |
| WO | 98/50577 A1 | 11/1998 |
| WO | 99/08233 A1 | 2/1999 |
| WO | 9920789 A1 | 4/1999 |
| WO | 99/35483 A1 | 7/1999 |
| WO | 99/36577 A1 | 7/1999 |
| WO | 99/40176 A1 | 8/1999 |
| WO | 9958948 A2 | 11/1999 |
| WO | 0004382 A1 | 1/2000 |
| WO | 0047766 A1 | 8/2000 |
| WO | 01/57522 A2 | 8/2001 |
| WO | 01/61348 A1 | 8/2001 |
| WO | 03/022999 A2 | 3/2003 |
| WO | 03/036290 A1 | 5/2003 |
| WO | 03/073817 A2 | 9/2003 |
| WO | 2005/082254 A2 | 9/2005 |
| WO | 2006/032044 A2 | 3/2006 |
| WO | 2006/106962 A1 | 10/2006 |
| WO | 2007/038478 A2 | 4/2007 |
| WO | 2007/145091 A1 | 12/2007 |
| WO | 2008/005998 A2 | 1/2008 |
| WO | 2008108027 A1 | 9/2008 |
| WO | 2010/036808 A1 | 4/2010 |
| WO | 2010/036827 A1 | 4/2010 |
| WO | 2010/036829 A1 | 4/2010 |
| WO | 2011/117545 A1 | 9/2011 |
| WO | 2012/035302 A1 | 3/2012 |
| WO | 2013/070730 A2 | 5/2013 |
| WO | 2013/158666 A1 | 10/2013 |
| WO | 2020/073015 A1 | 4/2020 |
| WO | 2020/073018 A2 | 4/2020 |

OTHER PUBLICATIONS

Allman, 1981, Fluoroimmunoassay of Progesterone in Human Serum of Plasma, Clin Chem 27:1176-1176.

(56) References Cited

OTHER PUBLICATIONS

Batchelor, 2012, Light and Optics, Machine Vision Handbook, Springer-Verlag, 157-258.
Catalogue of Becton, 2003, Dickinson and Company, p. 28, 29, 32-35, 150 and 151, Japan.
CCD detectors (http://www.astrosurf.com/re/chip.html) published online Feb. 22, 2001, from web archive http://web.archive.org/web/20010222014106/http://astrosurf.com/re/chip.html, retrieved Apr. 12, 2012, 5 pages.
Clean Technology, 1995, 5(8):60-61 (no english translation provided).
Colony Counter (http://www.topac.com/acolyte.html), retrieved Apr. 12, 2005, 3 pages.
Colony Counter Models and Specifications (http://biologics-inc.com/cc-models.htm), retreived Apr. 15, 2005, 3 pages.
Corkidi, 1998, COVASIAM: An Image Analysis Method That Allows Detection of Confluent Microbial Colonies and Colonies of Various Sizes for Automated Counting, Appl Environ Microbiol 64(4):1400-1404.
Crowther, 2000, Methods in Molecular Biology, The ELISA Guidebook, Humana Press, 425 pages.
Definition and Procedure for the Determination of the Method Detection Limit, Appendix B to 40 C.F.R. § 136, available at http://access.gpo.gov, retreived Nov. 20, 2007, pp. 343-346.
Digital Multi-Purpose High Resolution Colony and Plaque Counter, http://www.loats.com/mla.html, retreived Apr. 12, 2005, 3 pages.
Esteban, 1992, Improved Direct Epifluorescent Filter Technique for Rapid Bioburden Control in Intravenous Solutions, J. Parenter. Sci. Technol. 46146-149.
Findlay, 1993, Automated closed-vessel sstem for in vitro diagnostics based on polymerase chain reation, Clin Chem, 39(9):1927-1933.
Freydiere, 1991, Detection of *Salmonellae* by using Rambach agar and by a C8 esterase spot test, J. Clin Microbiol. 29(10):2357-2360.
Frost, 1921, Improved Technic for the Micro or Little Plate Method of Counting Bacteria in Milk, J. Infect. Dis. 28 (2):176-187.
Gite, 2018, A Rapid, Accurate, Single Molecule Counting Method Detects Clostridium difficile Toxin B in Stool Samples, Scientific Reports, 8:1-8.
Gray, 2011, Identification of micro-organisms after milliflex rapid detection—a possibility to Identify nonsterile findings in the milliflex rapid sterility test, PDA J Pharm Sci Technol. 65(1):42-54.
Graziani-Bowering, 1997, A quick, easy and inexpensive method for the isolation of human peripheral blood monocytes, J of Immunol Methods, 207(2):157-168.
Innovative Plate Holder for ProtoCOL, http://www.synbiosis.com retrieved Oct. 16, 2002, 2 pages.
Int Search Report and Written Op mailed Feb. 19, 2020, for Int Application No. PCT/US2019/054885, filed Oct. 4, 2019 (12 pages).
Int Search Report and Written Op mailed Jan. 13, 2010, for Int Application No. PCT/US2009/58237, filed Sep. 24, 2009, (10 pages).
Int Search Report and Written Op mailed Jan. 16, 2020, for Int Application No. PCT/US2019/054884, filed Oct. 4, 2019 (7 pages).
Int Search Report and Written Op mailed Jan. 17, 2020, for Int Application No. PCT/US2019/054887, filed Oct. 4, 2019 (12 pages).
Int Search Report and Written Op mailed Jan. 17, 2020, for Int Application No. PCT/US2019/054888, filed Oct. 4, 2019 12 pages).
Int Search Report and Written Op mailed Jul. 10, 2019, for Int Application No. PCT/US2019/028397, filed Apr. 19, 2019 (11 pages).
Int Search Report and Written Op mailed Nov. 20, 2009, for Int Application No. PCT/US2009/058274, filed Sep. 24, 2009 (10 pages).
Kamentsky, 2001, Laser Scanning Cytometry, Methods Cell Biol. 63:51-87.
Kepner, 1994, Use of fluorochromes fo direct enumeration of total bacteria in environmental samples: past and present, Microbiol Rev. 58(4):603-615.

Kroll, 1989, A Laser-Light Pulse Counting Method for Automatic and Sensitive Counting Of Bacteria Stained with Acridine Orange, J. Appl. Bacteriol. 66:161-167.
Lamture, 1994, Direct Detection of Nucleic Acid Hybridization on the Surface of a Charge Coupled Device, Nucleic Acids Res. 22(11):2121-2125.
Loates Associates Inc., 1999, System Specifications http://www.loats.com/order_info.html, retrieved Apr. 12, 2005, 7 pages.
Loats, 1990, LAI High-Resolution Automated Colony Counting System-Mouse Lymphoma Assay: Performance Analysis, http://loats.com/docs/HRCCval/HRCCval.htm, pp. 1-11.
Logtenberg, 1985, Enumeration of (Auto) Antibody Producing Cells in Human Using the "Spot-ELISA," Immunol. Lett. 9:343-347.
London, 2010, An Automated System for Rapid Non-Destructive Enumeration of Growing Microbes, PLoS One 5(1): e8609, 16 pages.
Masuko, 1991, A Novel Method for Detection and Counting of Single Bacteria in a Wide Field Using an Ultra-High-Sensitivity TV Camera Without a Microscope, FEMS Microbiol. Lett. 81:287-290.
Masuko, 1991, Rapid Detection and Counting of Single Bacteria in a Wide Field Using a Photon-Counting TV Camera, FEMS Microbiol. Lett. 83:231-238.
Mignon-Godefroy, 1997, Solid Phase Cytometry for Detection of Rare Events, Cytometry 27, pp. 336-344.
Miraglia, 1999, Homogeneous Cell-and Bead-Based Assays for High Throughput Screening Using Fluorometric Microvolume Assay Technology, J. Biomol. Screen. 4:193-204.
Moore, 1998, Lymphocyte fractionation using immunomagnetic colloid and a dipole magnet flow sorter, J Biochem Biophys Methods, 37:11-33.
Nargessi, 1980, Magnetizable Sold-Phase Fluoroimmunoassay of Thyroxines by a Sequential Addition Technique. Clin Chem 26(12):1701-1703.
Nargessi, 1984, Immunoassays for Serum C-Reactive Protein Employing Fluorophore-Labelled Reactants, J. Immunol. Methods 71:17-24.
Nealson, 1978, Isolation, identification, and manipulation of luminous bacteria, Methods Enzymol. 57:153-166.
Nebe-von-Caron, 2000, Analysis of bacterial function by multi-colour fluorescence flow cytometry and single cell sorting, J. Microbiol Methods, 42(1):97-114.
Nelis, 2000, Enzymatic Detection of Coliforms and *Escherichia coli* Within 4 Hours, Water Air and Soil Pollut. 123:43-52.
Patterson, 1966, A wide angle camera for photographic search of the ocean bottom, SPIE, C-XII-1-8.
Perkinelmer, Inc., 2007, GeneScreenTM Hybridization Transfer Membranes: transfer and detection protocols, Application Notes, available at http://las.perkinelmer.com, retrieved Feb. 27, 2007.
Porter, 1980, The use of DAPI for identifying and counting aqquatic microflora, Limnol Oceanogr. 25(5):943-948.
Rousseau, 1999, New Miniaturized Highly Sensitive Immunassay Device for Quantitative Measurement of Soluble or Particular Antigen or Antibodies in a Liquid Sample, Clin. Chem. 45(9):1685-1687.
Schultz, 2000, Single Target Molecule Detection with Nonbleaching Multicolor Optical Immunolabels, Proc. Natl. Acad. Sci. USA 97(3):996-1001.
Sorcerer Automated Colony Counting, 2002, Perceptive Instruments, 2 pages.
Supplementary European Search Report and Written Opinion for European Application No. EP 09816857, date of mailing: Mar. 20, 2012, 8 pages.
Susa, 1998, Legionella pneumophila infection in intratracheally inoculated T cell-depleted or -nondepleted A/J mice, J Immunol, 160: 316-321.
Technical Specification http://www.perceptive.co.uk/products/_scc/techspec.html, retrieved Apr. 12, 2005, 2 pages.
Texas Instruments TC211 192×165 Pixel CCD Image Sensor description dated Jan. 1990, 13 pages.
Thomas, 2000, Making gold nanoparticles glow: enhanced emission from a surface-bound fluoroprobe, J Am Chem Soc, 122:2655-2656.

(56) References Cited

OTHER PUBLICATIONS

Tibbe, 1999, Optical Tracking and Detection of Immunomagnetically Selected and Aligned Cells, Nature Biotechnol. 17:1210-1213.
Van Pouche, 2000, A 210-min Solid Phase Cytometry Test for the Enumeration of *Escherichia coli* in Drinking Water, J. Appl. Microbiol. 89:390-396.
Van Poucke, 1999, Solid Phase Cytometry-Based Enzymatic Detection of Coliforms in Drinking Water Within 4 h, Water Supply 17:67-72.
Van Poucke, 2000, Rapid Detection of Fluorescent and Chemiluminescent Total Coliforms and *Escherichia coli* on Membrane Filters J. Microbiol. Methods 42:233-214.
Vidon, 2001, A Simple Chemiluminescence-Based Method for Rapid Enumeration of *Listeria* spp. Microcolonies, J. Appl. Microbiol. 90:988-993.
Viinikka, 1981, A Two-Site Immunofluorometric Assay for Human Placental Lactogen, Clin. Chim. Acta. 114:1-9.
Waggoner, 1990, Fluorescent Probes for Cytometry, Flow Cytometry and Sorting, Wiley-Liss, 209-225.
Wellman, 2006, Magenetically-Assisted Transport Evanescent Field Fluoroimmunoassay, Anal, Chem. 78:4450-4456.
Wilson, 1995, Use of the IUL Countermat Automatic Colony Counter for Spiral Plated Total Viable Counts, Appl. Environ. Microbiol. 61:3158-3160.
Wolniak, 2004, BSCI 427 Principles of Microscopy Fall 2004 Syllabus, http://www.life.umd.edu/cbmg/faculty/wolniak/wolniakmicro.html, retrieved Nov. 8, 2007, 8 pages.
Yasui, 1997, Imaging of Lactobacillus brevis Single Cells and Microcolonies Without a Microscope by an Ultrasensitive Chemiluminescent Enzyme Immunoassay with a Photon-counting Television Camera, Appl. Environ. Microbiol. 63:4528-4533.
Zhao, 2004, Competitive Immunoassay for Microliter Protein Samples with Magnetic Beads and Near-infared Fluorescence Detection, Anal Chem. 76:1871-1876.
First Office Action mailed Aug. 25, 2023 by the Chinese Patent Office in Chinese Application 201980040840 (English translation, 12 pages).

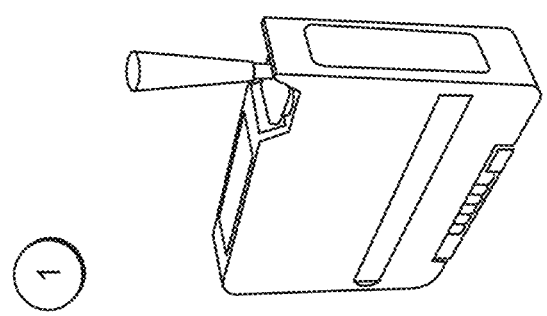
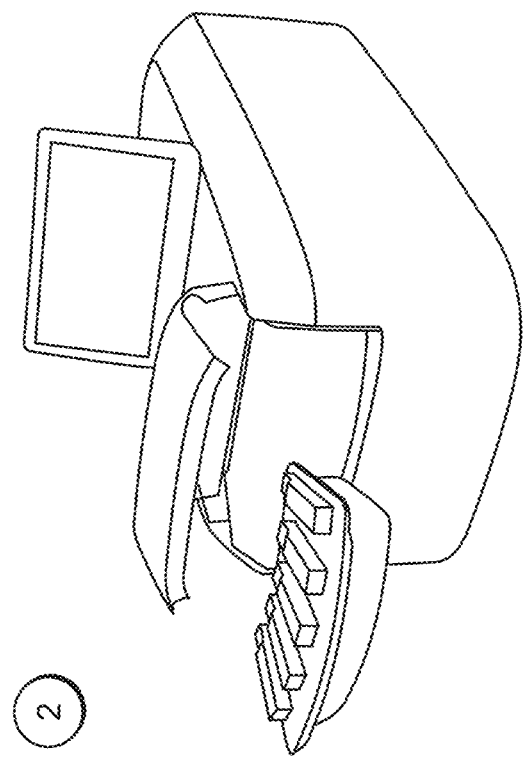
FIG. 22

| Assessment | Test Performance Goal | Example 1 | Example 2 |
|---|---|---|---|
| Limit of Detection (LoD)[19] | ≤150 pg/mL blood (x4) | 10 pg/mL | 7 pg/mL |
| Repeatability (precision) | CV <15% | 1-2% | - |
| Chemical interference testing[42] | No cross-reactivity with off-target microbes | No cross-reactivity with off-target microbes | - |
| Microbial interference Testing[43] | Report performance in the presence of inhibitors and microbes | No inhibition detected | - |
| Performance across samples[39] | No matrix impact at threshold conc. (100 samples) | 59.5% Accuracy | - |
| Stability | 18 months of stability at room temperature | Accelerated stability OK | - |
| Nonhuman primate samples[20] | Accurate calls for NHP anthrax samples using Alpha Platform | NA | 100% accuracy |

FIG. 32

| Sample ID | MultiPath Call | Reference method result (ng/ml) |
|---|---|---|
| C65999 Day - 14 | Negative | <LoD of reference method |
| C65999 36h | Positive | 14.5 |
| C65999 48h | Positive | 22.6 |
| C65999 72h | Positive | 14.4 |
| C65999 84h | Positive | 14.7 |
| C69742 Day - 14 | Negative | <LoD of reference method |
| C69742 36h | Positive | 1.34 |
| C69742 48h* | Positive | 18.7 |
| C69742 72h | Positive | 8.98 |
| C69742 84h | Positive | 7.98 |
| C69742 Day 14 | Negative | <LoD of reference method |
| C69742 Day 21 | Negative | <LoD of reference method |
| C69742 Day 28** | Negative | <LoD of reference method |

FIG. 35

|  | Traditional FISH | MultiPath FISH |
|---|---|---|
| Time | 1-24 hr | 30 min |
| Universal reagent | No | Yes |
| Consumables | Several | MultiPath Cartridge |
| Temperatures | Multiple temps | Isothermal |
| Reagent changes | Multiple | None |
| Manual steps | Multiple | None |
| Cell fixation | Required | Not required |

FIG. 37

| Assessment [data slide #] | Test Performance Goal | | Results |
|---|---|---|---|
| Limit of Detection (LoD)[28] | 10K CFU/mL urine | E. coli K. pneumoniae Enterococcus spp. P. aeruginosa | All targets ≤10,000 CFU/mL |
| Time to result | 30 min | All targets | 30 min |
| Universal conditions | Isothermal with universal reaction diluent | All targets | Universal conditions |
| Inclusivity and Exclusivity[40, 41] | Inclusivity for 10 isolates of each species. | All targets | Can detect all strains; no off-target detection |
| Robustness to Chemical Interference | Performance in presence of potentially inhibitory substances | E. coli | Size-exclusion removes potential interferents |
| Total bacterial cells (In microtiter plates) | 10K cfu/ml total bacteria | All targets | — |

FIG. 38

| | Key Metrics | Test Performance Goal | Strains tested | Results |
|---|---|---|---|---|
| In microtiter plates | AST Accuracy | Correct sensitivity/resistance call for strains of each target species for all drugs tested in spiked urine in 4 hours | E. coli<br>P. aeruginosa<br>Klebsiella spp.<br>Enterococcus spp. | 99% Categorical Agreement in 4.5 hours |
| | Inoculum effects on AST | Report impact of matrix effects | E. coli<br>P. aeruginosa<br>Klebsiella spp. | 100% Categorical Agreement |
| | Matrix effects on AST | Report impact of variable inoculation | E. coli | 96% Categorical Agreement |
| | AST robustness to off-target bacteria | Report impact of polymicrobial infections | E. coli | 99% Categorical Agreement |
| Platform | AST proof-of-concept using Alpha Platform | Correct calls for susceptible and resistant isolates | E. coli | Initial experiment complete | completed ▨

FIG. 40

| E. coli target detected in assay | Concentration of non-target bacteria added | Essential Agreement |
|---|---|---|
| E. coli 1e5 CFU/mL | 1e5 CFU/ml | 100% |
| | 1e6 CFU/ml | 100% |
| | 1e7 CFU/ml | 96% |

|  | Key Metrics | Test Performance Goal | Results |
|---|---|---|---|
| in microtiter plates | Limit of Detection (LoD) | 10,000 cfu/mL urine | All targets ≤10K CFU/mL |
| | Inclusivity and Exclusivity | 10 inclusivity, 10 exclusivity for each species | Detected all strains; no off-target detection |
| | Microbial and Chemical Interference | Performance in presence of potentially inhibitory substances and microbes | Size-exclusion removes potential interferents |
| | Total bacterial cells | 10,000 cfu/ml total bacteria | In process |
|  | Key Metrics | Test Performance Goal | Results |
| in microtiter plates | AST Accuracy | Correct sensitivity/resistance call for strains of each target species for all drugs tested. | 99% Categorical Agreement |
| | Inoculum effects on AST | Report impact of variable inoculation | 100% Categorical Agreement |
| | Matrix effects on AST | Report impact of matrix effects | 96% Categorical Agreement |
| | AST robustness to off-target bacteria | Report impact of polymicrobial samples | 99% Categorical Agreement |
| | AST using Platform | Correct calls for susceptible and resistant isolates | Initial experiment complete | completed ▨

FIG. 45

| Target | Number of strains detected at 5X target LoD | Strains tested |
|---|---|---|
| E. coli | 10/10 | ATCC 25922, BAA-2469, CDC0061, CDC0084, CDC0089, ATCC 700415, ATCC 700417, CDC0019, CDC 0149, U9-40 |
| Klebsiella spp. | 11/11 | K. pneumoniae: ATCC 13883, CDC0034, CDC0043, CDC0076, CDC0087, CDC0107, CDC017, CDC0128, CDC0141<br>K. oxytoca: CDC0071, CDC0146 |
| P. aeruginosa | 10/10 | CDC0232, CDC0233, CDC0234, CDC0236, CDC0242, CDC0246, CDC0253, CDC0261, CDC0263, CDC0266 |
| Enterococcus spp. | 6/6 | ATCC 29212, ATCC 51575, ATCC 51559, ATCC 19434, BAA-2318, BAA 51589 |

FIG. 46

| Target | Number of bacteria species tested for cross-reactivity | Number of species where cross-reactivity was observed |
|---|---|---|
| E. coli | 15 | 0* |
| Klebsiella spp. | 10 | 0 |
| P. aeruginosa | 10 | 0 |
| Enterococcus spp. | 10 | 0 |

\* - low level cross-reactivity observed in 3 of 15 strains, but was not enough to be detected by MultiPath using optimized thresholding

FIG. 47

DETECTION OF TARGETS

CROSS-REFERENCE TO RELATED APPLICATIONS

This application claims the benefit of and priority to U.S. Provisional Application No. 62/660,075, filed Apr. 19, 2018, and U.S. Provisional Application No. 62/711,784, filed Jul. 30, 2018, the contents of each of which are incorporated by reference herein in their entirety.

GOVERNMENT SUPPORT

This invention was made with government support under grant numbers AI055195, AI055195, AI080016, AI078695, AI080016, and AI117058 awarded by the National Institutes of Health as well as contract number HHSO100201500022C awarded by the Biomedical Advanced Research and Development Authority. The government has certain rights in the invention.

TECHNICAL FIELD

The invention generally relates to analysis and detection of microbes and molecules.

BACKGROUND OF THE INVENTION

Detecting microbes and molecules underlie important applications in human medicine, veterinary medicine, agriculture, industrial microbiology, and scientific research. Infectious disease diagnostics is one important field in which detection of microbes plays a central role.

Infectious diseases, caused by a range of pathogens, are a leading cause of death. For example, C. difficile tops the CDC's Urgent Threat Level category for microorganisms, causing more deadly hospital infections than any other pathogen. C. difficile infections (CDIs) are responsible for an estimated 450,000 infections, 29,000 deaths, and $1-6B in health care costs per year in the US. C. difficile infection causes severe diarrhea that can lead to pseudomembranous colitis, toxic megacolon, multi-organ failure, and death. Unfortunately, conventional methods of detection for Clostridium difficile lack sensitivity and specificity.

C. difficile is a common commensal Gram-positive spore-forming anaerobic gut microbe with colonization rates as high as 50% in hospital patients. Most infected patients harbor C. difficile in its dormant and benign spore form. Because the microbial spores can be induced to germinate and become virulent by changes in gut metabolites occurring when other intestinal microbes are eliminated by antimicrobial agents, patients who are taking antibiotics are at a higher risk for C. difficile infection. Virulent toxigenic C. difficile strains secrete cytopathic toxins including Toxin B and Toxin A. Colonized patients with no infection can be distinguished from patients with C. difficile infection based on the level of toxin in the stool. Patients with C. difficile infection have higher levels of Toxin B than do colonized, non-infected patients.

Rapid commercial immunoassays are available for detecting C. difficile toxins in stool samples, but are not clinically sensitive enough to detect all C. difficile infected patients, due to having analytical sensitivities of several ng/ml, which is significantly above the clinical threshold. More sensitive tests, based on the gold standards Cell Cytotoxicity Neutralization Assay (CCNA), are commercially available, but are slow (taking 1-3 days for results), can be subjective, and are too expensive for routine clinical use.

In contrast to current rapid immunoassay tests, nucleic acid amplification tests (NAATs) have high clinical sensitivity. However, those tests detect the presence of the C. difficile genome, but cannot distinguish between patients that are benignly colonized with C. difficile spores from patients that have a C. difficile infection. Although only patients with severe diarrhea should be tested for C. difficile infection, many patients in hospitals have diarrhea due to other causes, such as laxatives, drug reactions, and viral infections. A significant fraction of those patients is colonized with C. difficile in the benign spore form and have no active infection. Accordingly, samples from such patients yield false positive results. Thus, while clinically sensitive, nucleic acid-based assays lack clinical specificity and have relatively poor positive predictive values.

Hospitals that have switched from toxin immunoassays to nucleic acid-based assays have seen increases in C. difficile infection diagnosis rates of 50-100%, due in part to the increase in false positives from colonized, but not infected, patients. False positives are problematic because patients are likely to get unnecessary antibiotic therapy, and antibiotic therapy actually increases the risk of developing C. difficile infection in uninfected patients. False positives can also increase the financial burden for hospitals.

The relatively low sensitivity of available rapid toxin immunoassays and lack of clinical specificity of nucleic acid based tests leave the current market with no single CDI diagnostic test with high clinical sensitivity and specificity that distinguishes colonized patients from those with active C. difficile infections.

SUMMARY OF THE INVENTION

The invention provides methods and devices for detecting microbes and biomarkers in a sample that requires minimal sample preparation. A clinician obtains a sample and places it directly in a cartridge for detection of a desired clinical analyte (or target).

Certain embodiments of the present invention are directed to methods, devices, and kits for detection of target microbes, which are useful for rapid, sensitive, and accurate counting of target microbes in a sample. In one aspect of the invention, a method for determining the presence of a target microbe in a sample is provided. For example, the target microbe could be Clostridium difficile, or components thereof, and detection determines whether a subject has a C. difficile infection. The method includes testing a stool sample from the subject for the presence of C. difficile or components thereof, such as toxin A or toxin B. For example, certain embodiments of methods of the invention can have an analytical sensitivity of 45 pg/ml for a 30 minute C. difficile toxin B test using stool samples and an analytical sensitivity of 365 pg/ml for a 30 minute C. difficile toxin A test using stool samples. Therefore, the invention provides rapid, sensitive detection of target microbes.

Methods and devices of the invention require minimal sample preparation, thereby saving time and cost associated with detection and analysis of microbes. For example, when testing for toxin A and toxin B of Clostridium difficile using a stool sample, sample preparation can entail merely diluting stool in assay buffer which is then passed through a nylon mesh filter to remove large particulates before adding the assay reagents. The simple sample preparation, lack of wash steps, and elimination of stepwise addition of reagents eliminates significant hands-on time, lowers cost, and simplifies instrumentation compared to other testing methods.

Methods of the invention are directed to detecting and counting targets. A target is the entity to be detected. For example, methods of the invention are useful to detect cells, proteins, nucleic acids, and carbohydrates. Examples in the present application demonstrate the detection of secreted molecules. However, the invention is useful to detect a broad range of molecules and cells including biomarkers, hormones, cell-surface proteins, intracellular proteins, nucleic acids and whole cells.

The invention can detect and count targets by tagging them with target-binding photonic and magnetic labels. As an example, a liquid sample obtained by a subject is analyzed after introduction into a cassette or cartridge containing an imaging well with a detection surface at the bottom. The bottom surface of the imaging well is coated with dye-cushion reagents comprising a density agent and a dye that absorbs light. The cartridge also contains magnetic and fluorescent particles which are coated with binding agents, for example antibodies, that bind specifically to the target. When the liquid sample is added, the dye-cushion dissolves, forming a lower dense opaque aqueous layer. The magnetic and fluorescent particles and sample form an upper assay layer. The targets bind to the fluorescent and magnetic labels in the assay layer. The cartridge is placed over a magnet which draws all of the magnetic particles through the dye-cushion layer, depositing the magnetic particles on the detection surface of the imaging well. Targets that are bound to magnetic particles and fluorescent particles will also be deposited on the imaging surface and can be imaged and counted. The dye-cushion functions to optically sequester the sample and unbound fluorescent labels from the detection surface. This can greatly improve the signal-to-noise levels when the sample is imaged, thereby minimizing or eliminating the need for sample preparation by the user and wash steps.

In some examples, the sample is a human stool sample or is derived from human stool, and the targets are pathogens, such as *Clostridium difficile*. Exemplary targets include toxin A and toxin B secreted by *Clostridium difficile*. In another example, the targets comprise Lethal Factor, a subunit of Lethal Toxin, secreted from *Bacillus anthracis*. The skilled artisan is aware of numerous additional targets that are apparent upon consideration of the present disclosure.

In some embodiments, the detection step further comprises counting the targets. Targets of interest are detected and counted on a detection surface by observing fluorescence from the fluorescent particles of the fluorescently-labeled targets. The detecting step comprises digital imaging. Digital imaging comprises illuminating the fluorescent particles and detecting signal emitted from the fluorescent particles on a photoelectric array detector. Any suitable digital imaging device may be used. In certain embodiments, detection does not employ optical magnification of greater than 5× or employs no magnification. In some embodiments, the steps of the method are performed using the cassette or cartridge. The cartridge is pre-loaded with fluorescent particles and magnetic particles. The cartridge includes a receiving reservoir into which a user introduces the sample, a dye-cushion and a detection surface provided in an imaging well in fluidic communication with a mixing well, and a plurality of paired imaging well and mixing well sets in parallel to one another. The cartridge also can include a filter that filters particulates from the sample, such as large particulates that may block fluid flow within the cartridge.

Certain aspects of the invention are directed to performing assays in parallel in multiple channels in the cassette. A first channel comprises sample detection. A second channel comprises a positive control. The positive control comprises detecting and counting targets in a positive control sample where a known amount of targets of interest is introduced. A third channel comprises a neutralization control. The neutralization control comprises detecting and counting targets in a neutralization control sample where neutralization binders are introduced that sequester targets of interest, thereby preventing fluorescent labeling of the targets. The method further comprises calculating a ratio of a detection signal from a sample to a signal detected from the neutralization control. The method further comprises determining whether the ratio exceeds a threshold.

In certain embodiments, the photonic labels can comprise fluorescent particles, fluorophores, chemiluminescent agents, bioluminescent agents, resonance light scattering particles, light absorption or chromogenic signaling agents, quantum dots, or up-converting phosphors.

In certain embodiments, particle reagents are conjugated to binding molecules that bind to the target of interest or component thereof. Examples of binding molecules include an antibody or antigen binding fragment thereof or an aptamer. In certain embodiments, the targets of interest are toxins secreted from a pathogen, such as toxin A and toxin B secreted from *C. difficile*.

Certain aspects of the invention are directed to a cassette or cartridge. The cartridge comprises a receiving reservoir into which a user introduces a sample. The cartridge can also comprise a mixing well for introducing the sample to fluorescent particles and magnetic particles, and an imaging well for detecting and counting targets from the sample. The imaging well is in fluidic communication with the mixing well. In some embodiments of the invention, the cartridge further comprises a plurality of paired imaging well and sample well sets in parallel to one another. The cartridge further comprises a filter for filtering particulates from the sample before mixing and detection.

The imaging well further comprises a dye-cushion and a detection surface. The dye-cushion comprises a density media that holds unbound sample and unbound fluorescent particles in the sample away from the detection surface, and a dye that interferes with transmission of light from unbound fluorescent particles in the sample. When a magnetic field is applied across the dye-cushion, the magnetic field pulls the magnetic particles through the dye-cushion to the detection surface. In some embodiments, the dye-cushion is provided in a dried or lyophilized state in the imaging well within the cartridge until wetted by sample. For example, in some embodiments, the dye-cushion is in dried form in the cartridge and providing the sample hydrates the dye-cushion in dried form.

In some embodiments of the invention, the cartridge further comprises a positive control sample with a known amount of targets. In some examples, the cartridge includes a neutralization control sample including the sample and free binding molecules that bind to the targets to reduce complex formation.

In certain aspects, methods of the invention further comprise detecting and counting targets in a positive control sample, the positive control comprising a known amount of the targets. For example, in certain embodiments, the method further includes repeating the steps with a positive control sample including the sample and a known amount of the targets. The method may also include repeating the steps with a neutralization control sample including the sample and free binding molecules that bind to the targets to reduce complex formation. The method can also include performing both the positive and neutralization controls. The method may include determining whether the targets counted from the sample exceed a threshold of targets counted from the neutralization control sample. The method may include determining whether a ratio of the targets counted from the sample to targets counted from the neutralization control sample exceeds a threshold. The method may also include determining whether the targets counted from the positive control sample exceeds a threshold.

In some embodiments, methods of the invention are carried out in a competitive format which can enable detection of small molecule targets. In such an example, the magnetic particles and fluorescent particles bind to each other to form complexes, and the target binds to one of the magnetic particles or fluorescent particles in order to reduce the number of complexes formed.

In certain aspects, the invention provides a kit including fluorescent particles, magnetic particles, and liquid density reagent or dried density reagent. The fluorescent particles and magnetic particles bind to targets of interest in a sample to form complexes of the targets. The kit may also be formulated for a competitive assay where the fluorescent particles and magnetic particles bind to each other to form complexes, and the targets bind to either the fluorescent particles or magnetic particles to reduce the number of complexes of particles formed. The kit may further include free binding agent and/or a known amount of the targets. The kit may further include a cartridge with a detection surface, multiple cartridges, or a cartridge with multiple wells to allow performance of control tests. In certain embodiments, the liquid density reagent or dried density reagent is stored in the cartridge. The kit may further include a dye disposed in the liquid density reagent or dried density reagent, or dye-cushion. In certain embodiments, the dye interferes with the transmission of light to or from the fluorescent particles. In certain embodiments, the photonic labels include fluorescent particles, fluorophores, chemiluminescent agents, bioluminescent agents, resonance light scattering particles, light absorption or chromogenic signaling agents, quantum dots, or up-converting phosphors. In other embodiments, the fluorescent particles and magnetic particles are conjugated to binding molecules that independently bind to the targets of interest or component thereof. Examples of binding molecules include an antibody or antigen binding fragment thereof or an aptamer. An exemplary component of a target is a secreted component, such as *C. difficile* toxin A or toxin B.

BRIEF DESCRIPTION OF THE DRAWINGS

FIG. 22 shows the platform Workflow for detection of *Clostridium difficile* Toxin B.

FIG. 32 shows analytical performance of the Anthrax Test.

FIG. 35 shows testing NHP inhalation anthrax samples on Example 2.

FIG. 37 shows comparison of Traditional FISH to MultiPath FISH.

FIG. 38 shows the UTI ID Test: studies in microtiter plates.

FIG. 40 shows UTI AST Test: studies in microtiter plates.

FIG. 45 shows Option 1 UTI ID/AST Summary.

FIG. 46 shows FISH Probe Inclusivity.
FIG. 47 shows FISH Probe Exclusivity

DETAILED DESCRIPTION

Methods and devices of the invention enumerate individual targets with simple optical equipment, minimal sample preparation, and rapid turnaround time. The invention can ultrasensitively detect informative targets in complex samples. For example, it can detect low levels of the disease-causing *C. difficile* toxin directly in minimally processed stool samples. As another example, the methods and devices of the invention can be used to detect low concentration of a toxin that causes anthrax.

An assay for *C. difficile* toxin B using the methods of the invention demonstrates performance equivalent to the CCNA reference method which is highly sensitive for the toxin B and used for regulatory clearance of *C. difficile* toxin tests. The analytical sensitivity of the 30 minute *C. difficile* toxin B test in stool samples is found to be high, for example 45 pg/ml, and the analytical sensitivity of the 30 minute *C. difficile* toxin A test in stool samples is found to be 365 pg/ml. Also, the accuracy of tested clinical samples is comparable to that of the cytotoxicity assay, a sensitive reference method.

Methods and devices of the invention require minimal sample preparation, thereby saving time and cost associated with detection and analysis of microbes. The use of a dye-cushion allows detection with minimal sample processing because the due cushion optically sequesters the sample and unbound fluorescent particles from the detection surface. Specifically, preparation for methods of the invention involve merely diluting stool in assay buffer and passing through a nylon mesh filter to remove large particulates before adding the assay reagents. The simple sample preparation, lack of wash steps, and elimination of stepwise addition of reagents eliminates significant hands-on time, lowers cost, and simplifies instrumentation compared to other testing methods.

Figure 1:
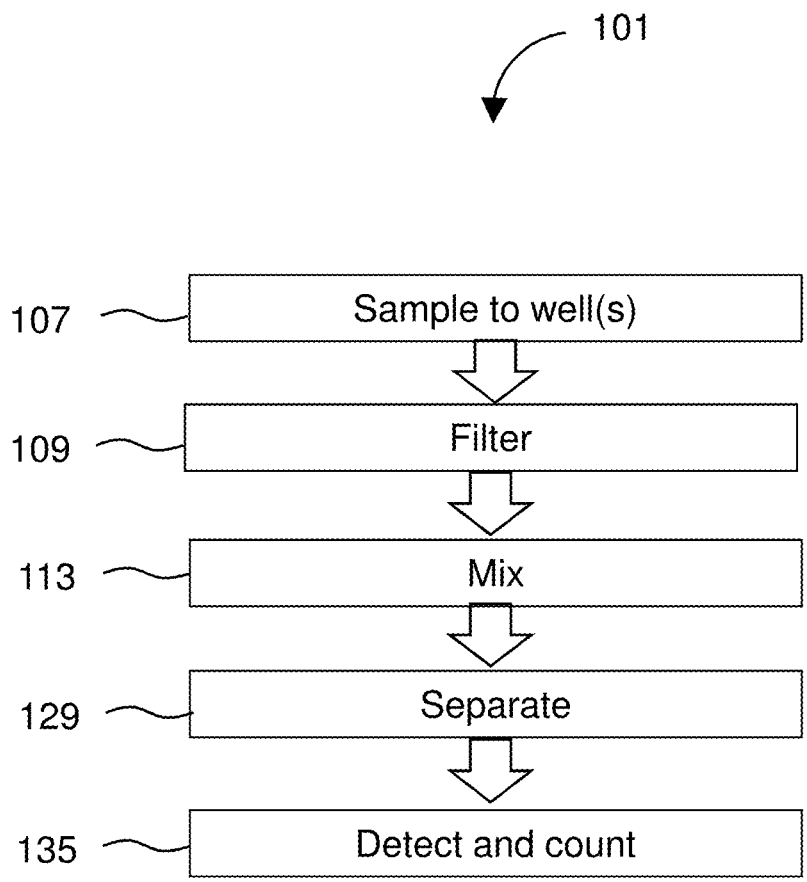
FIG. 1 is a flow chart of an exemplary embodiment of methods of the invention.

FIG. 1 diagrams a method 101 for detecting targets. The method 101 preferably includes obtaining a sample suspected to contain targets of interest, such as a stool sample from a patient with an infection. The sample may be delivered 107 into a collection tube, well, reservoir, or cartridge for processing according to the steps herein. For example, a stool sample may be collected by a patient using a collection cup and delivered to a clinician. The sample may be frozen. The clinician may use a disposable pipette such as a 1 mL plastic graduate transfer pipette to transfer 107 a portion of the sample into a receiving reservoir of a testing device or cartridge. The method may further include filtering 109 the sample, as a stool sample has high potential for particulates. For identifying or detecting the presence of targets in the sample, the method 101 includes mixing 113 the sample with fluorescent particles and magnetic particles that bind only to a particular target. For example, the fluorescent particles and magnetic particles may be conjugated to molecules that independently bind to targets selected from cells, proteins, nucleic acids, carbohydrates, and sugars. In an example, the targets comprise at least one of toxin A and toxin B of *Clostridium difficile*. In an example, the targets comprise Lethal Factor, a subunit of Lethal Toxin, secreted from *Bacillus anthracis*. The method 101 further includes separating 129 magnetic particles, bound and unbound, from the sample. Magnetic particles bound to targets are separated from the rest of the sample. The targets bound to the magnetic particles will also be bound to fluorescent particles. Therefore, if targets are present, the targets will be bound to magnetic particles and fluorescent particles and separated from the rest of the sample. Methods further include detecting 135 and counting targets by observing fluorescence from the fluorescent particles bound to the targets.

Figure 2:
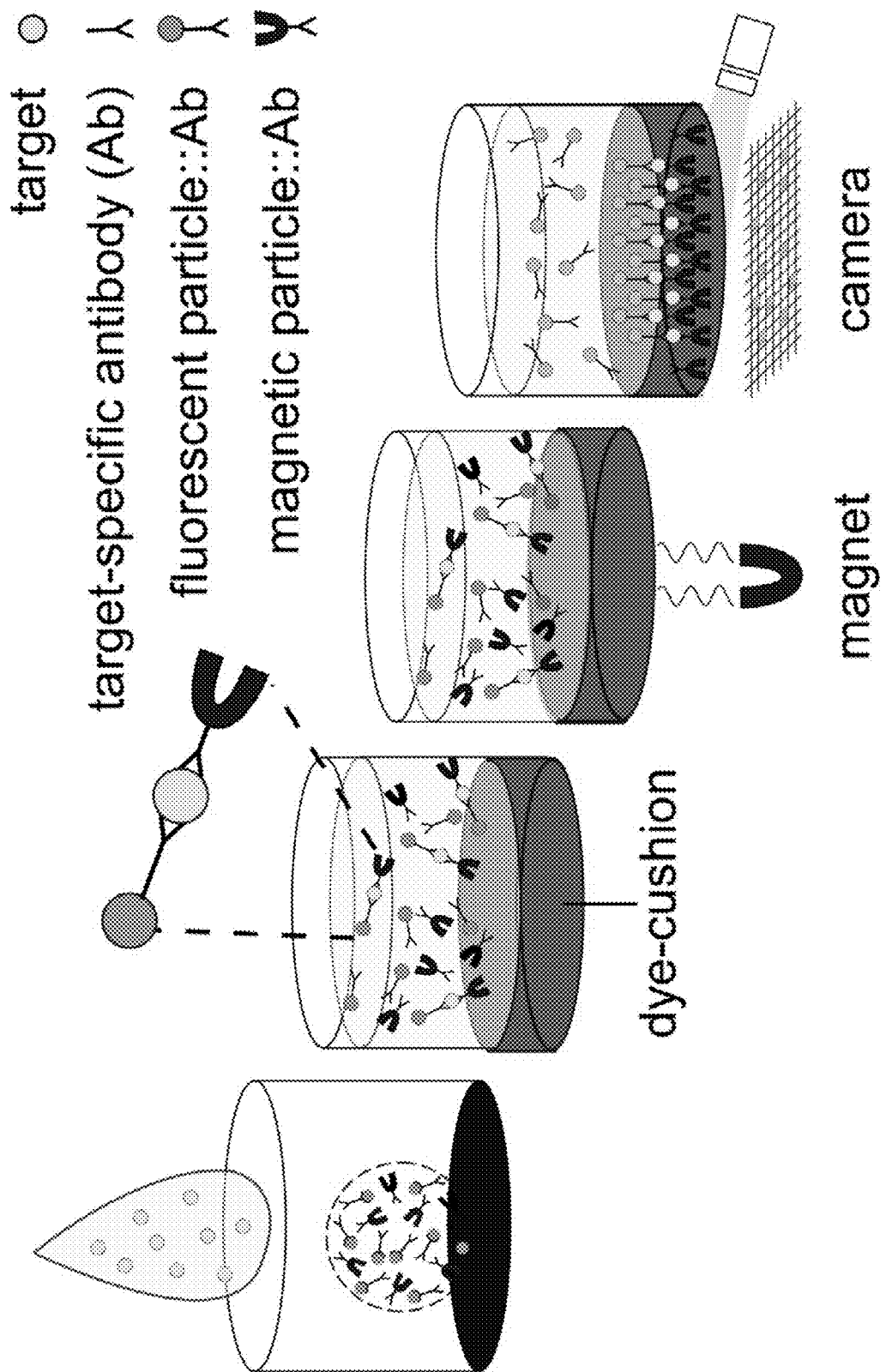
FIG. 2 shows an exemplary embodiment of methods of the invention.

FIG. 2 shows methods according to the invention. Methods detect and count targets by tagging them with target-binding photonic and magnetic labels. As an example, a liquid sample obtained by a subject is analyzed after introduction into a cassette or cartridge containing an imaging well with a detection surface at the bottom. The bottom surface of the imaging well is coated with dye-cushion reagents comprising a density agent and a dye that absorbs light. The cartridge also contains magnetic and fluorescent particles which are coated with binding agents, for example antibodies, that bind specifically to the target. When the liquid sample is added, the dye-cushion dissolves, forming a lower dense opaque aqueous layer. The magnetic and fluorescent particles and sample form an upper assay layer. The targets bind to the fluorescent and magnetic labels in the assay layer. The cartridge is placed over a magnet which draws all of the magnetic particles through the dye-cushion layer, depositing the magnetic particles on the detection surface of the imaging well. Targets that are bound to magnetic particles and fluorescent particles will also be deposited on the imaging surface and can be imaged and counted. The dye-cushion functions to optically sequester the sample and unbound fluorescent labels from the detection surface. This can greatly improve the signal-to-noise levels when the sample is imaged, thereby minimizing or eliminating the need for sample preparation by the user and wash steps.

FIG. 2 shows magnetic particle-bound targets being separated from unbound fluorescent particles and remaining sample by pulling the targets through a density gradient medium using an applied magnetic field. The density medium may be supplied within a tube or well (and may include a dye to provide a "dye-cushion") as pictured, such that the separating may include distributing magnetic particle-bound targets over the dye-cushion and using a magnetic field to pull bound targets through the dye-cushion and onto an imaging surface, leaving the unbound probes on the surface of the dye-cushion. The detecting step may then include imaging the imaging surface using digital imaging. Thus, as shown the mixing step includes exposing the sample to magnetic particles that bind to targets of interest and the separating step includes using a magnetic field to pull bound targets away from the unbound labels. Preferably, the separating step includes distributing magnetic particle bound targets over a surface of a dye-cushion, and using the magnetic field to pull bound targets through dye-cushion and onto an imaging surface, leaving the unbound labels on the surface of the dye-cushion.

As discussed, embodiments of the separation make use of a density gradient medium dye-cushion that may include a dye to provide a dye-cushion and density agent. The dye-cushion 803 may comprise a density agent (such as iodixanol) and a light-absorbing dye. The dye-cushion may optionally be dried or lyophilized prior to exposure to the sample) that further includes a dye that absorbs light. The dye-cushion forms an aqueous layer which is of higher density than the assay layer containing the sample and assay reagents. The dye-cushion can include various density agents singly or in combination (and at various concentrations) including for example, sucrose, diatrizoate, iodixanol (aka OptiPrep), NaCl, CsCl, Percoll, or albumin. Embodiments can also incorporate other density agents, including other commonly used density agents such as sodium diatrizoate, other sugars, oligosaccharides, synthetic polymers (e.g., Ficoll), and various salts such as potassium bromide, and others. Embodiments may use dyes to match the different various excitation and emission regimes for the photonic detection and the corresponding photonic signaling characters of the photonic labels in use. For example the dye Toluidine Blue O could be used with the fluorescent label Texas Red (sulforhodamine). One embodiment uses a 65 µL aliquot of dye-cushion reagent, which is 2 mg/mL Chromotrope R2 and 10% v/v OptiPrep (a 60% w/v solution of iodixanol) plus 5% w/v trehalose pipetted into assay wells. The dye-cushion may be 15% OptiPrep and 5 mg/mL Chromotrope R2 pre-aliquoted in 96-well half-area diameter clear bottom black plate or into the imaging wells of a cartridge. With reference to the well 915, the dye-cushion 903 can be formed by preparing a solution of iodixanol or polyvinylpyrrolidone, including any optional dye, and drying or lyophilizing the solution there in the well 915 to form the dye-cushion 915. The dye-cushion 915 will then be essentially a solid (e.g., dried, e.g., the well 915 can be stored in any orientation including upside-down until use). When a liquid sample is delivered into the well 915, the liquid rehydrates the dye-cushion 803. In fact, the reagents disclosed and discussed throughout herein for use in the method may be provided in dried or lyophilized form for later use. This allows the reagents to be prepared and loaded dry onto a cartridge that may then be shipped or stored and later used in methods of the disclosure.

Certain embodiments of the methods and devices for detecting microbes and molecules use magnetic particles conjugated to target-specific antibodies.

Figure 3:
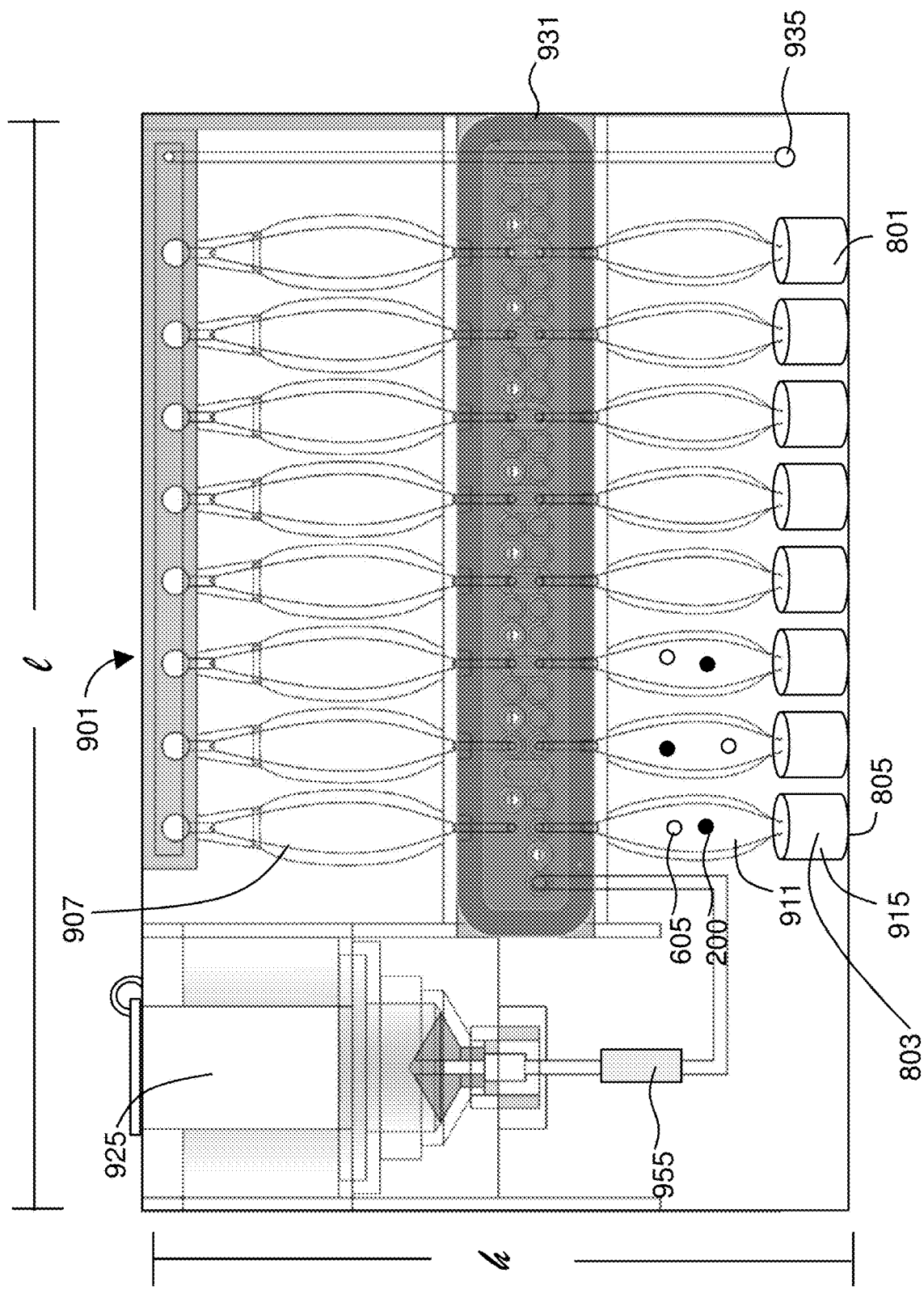
FIG. 3 shows an exemplary embodiment of a cartridge according to the invention.

FIG. 3 shows one embodiment of a cassette or cartridge 901 useful for performing the method. The cartridge 901 includes a mixing well 911. A sample potentially comprising targets of interest 201 is delivered into the mixing well 911. The sample may pass through a filter 955 before being delivered to the mixing well 911. A sample may be a stool sample comprising particulates. Passing the sample through a filter will reduce risk of clogging the cartridge. Any suitable filter may be used, such as a 0.45 micron membrane filter, 0.45 µm nitrocellulose filter, 0.65 µm nitrocellulose filter, or 0.6 µm polycarbonate filter.

The cartridge 901 also includes magnetic particles 605 that bind to targets of interest; and a dye-cushion adjacent a detection surface 805. When a magnetic field is applied across the dye-cushion 803, the magnetic field pulls the magnetic particles 605 through the dye-cushion to the transparent wall. The dye-cushion 803 comprises a solution of density gradient medium 801 that further includes a dye that absorbs light from unbound fluorescent particles 200. In the depicted embodiment, the dye-cushion 803 and the detection surface 805, such as a transparent wall, are provided in an imaging well 915 in fluidic communication with the mixing well 911. The dye-cushion 803 is provided in a dried or lyophilized state in the imaging well within the cartridge until wetted by sample.

As shown, the cartridge may include a plurality of paired imaging well/mixing well sets in parallel to one another. Here, the cartridge 901 is shown as including 8 parallel "channels" in which each channel includes a division well 901, a mixing well 911, and an imaging well 915. Embodiments of the cartridge may include 2 gangs of 8 channels such that the picture in FIG. 4 would look about the same, because the additional 8 channels would be behind the eight visible channels (the cartridge is a 3-dimensional object). The cartridge may be described according to its dimensions such as height h, length l, and width w (where width w is measured normal to the page in FIG. 3). Height h may be between about 3 and 10 cm. length l may be between about 5 and 12 cm. Width w may be between about 0.5 and 3 cm. For example, in one embodiment, h is about 6 cm, l is about 8 cm, and w is about 2 cm.

The cartridge 901 preferably includes a receiving reservoir 925 into which a user can pipette the sample into the cartridge. In certain embodiments, the cartridge 901 includes a slideable gate 931 comprising a gasket with channels therethrough. When the gate 931 is positioned at a first position, the receiving reservoir 925 is in fluid communication with at least the first division well 907. When the gate 931 is in a second position, the receiving reservoir 925, the first division well 907, and a first mixing well 911 are all sealed from one another. When the gate 931 is in a third position, the first division well 907 and the first mixing well 911 are in fluid communication with each other.

The cartridge 901 may include a fitting 935 for coupling to an external instrument to receive pneumatic pressure therefrom to divide (hence, "division") the sample from the receiving reservoir 925 into the division wells 927 and to subsequently pass liquid from the division wells 907 into corresponding mixing wells 911.

The dye-cushion 803 comprises a density agent 801 and a dye that absorbs light. The dye-cushion 803 may be provided in a dried or lyophilized state in the imaging well within the cartridge until wetted by sample.

Figure 4:
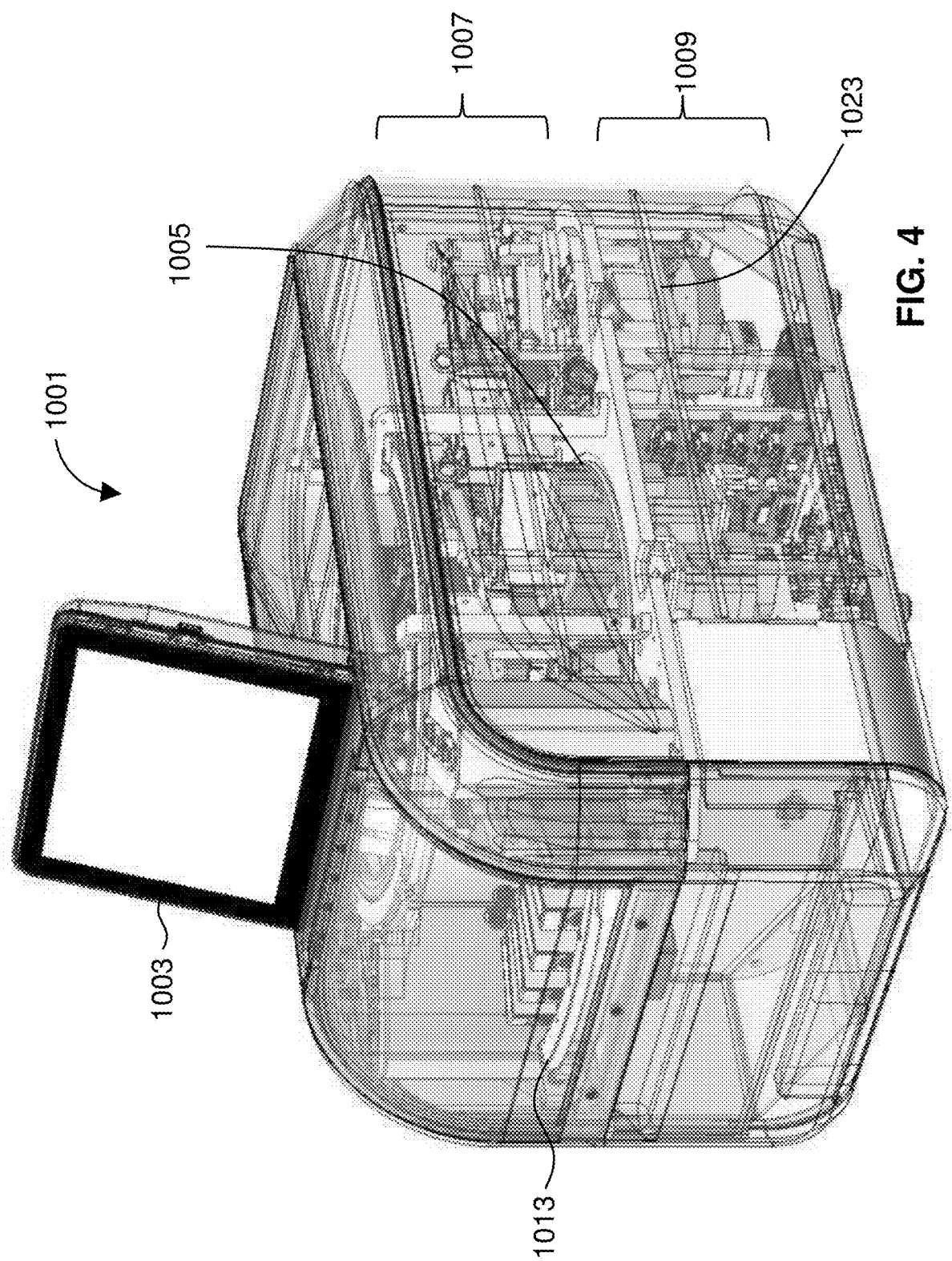
FIG. 4 shows an exemplary embodiment of an instrument for use in the invention.

FIG. 4 shows an exemplary instrument 1001 (e.g., analyzer) for performing target identification and analysis of samples within a cartridge 901. The instrument 1001 may be used to interact with cartridges 901 to perform methods 101 and processes entailed by the invention. The instrument 1001 can include a user interface 1003 (e.g., a touch screen) to display prompts, results, reports 129 and to receive commands. The instrument 1001 may include multiple work stations. The instrument may include a carousel 1005 for transporting cartridges, an upper compartment 1007 for housing processing and optional incubation equipment, and a lower compartment 1009 for housing electronics, imaging and pneumatic equipment. The instrument 1001 may include an input mechanism 1013 (e.g., a loading rack or tray) for accepting and cataloging a plurality of analytical cartridges. The instrument 1001 may also include a carousel 1005 and a pusher mechanism to move cartridges within the instrument. The instrument 1001 may also include a task scheduler. The instrument 1001 is preferably controlled by a computer to automate manipulation of analytical cartridges, performance of microbe identification and analysis, and generation of results. The instrument 1001 may include a plurality of subsystems to perform methods of the invention.

Subsystems of the instrument 1001 may include a pneumatic subsystem, a magnetic subsystem, a clamshell heater, and an imaging subsystem 1023. The magnetic subsystem may include, for example, a permanent magnet or an electromagnet to provide a magnetic field B to pull magnetic particles and targets on the detection surface of the analytical cartridge for imaging. The imaging subsystem may be such as those described in U.S. Pat. Nos. 9,643,180 and 8,021,848, both incorporated herein by reference, to capture images of targets, and a stage to manipulate the detection surface of the cartridge relative to the imaging module of the instrument 1001. The imaging subsystem 1023 can be operably associated with the computer to provide image processing, analysis, and display capabilities. The pneumatic subsystem may be operable to drive movement of the sample and reagents within the cartridge.

In some embodiments the pusher mechanism (e.g., mechanical conveyor arm) may be operable to move the cartridge 901 amongst the various subsystems within the instrument 1001. In some embodiments of the invention, the pusher mechanism transfers cartridges between the carousel 1005 and the various subsystems of the instrument. The pusher mechanism pushes or pulls cartridges onto and off of the carousel 1005. The carousel 1005 rotates to position a cartridge adjacent another one of the subsystems and the pusher may then apply force to slide the cartridge onto the subsystem. In some embodiments, the instrument includes a task scheduler for managing the analytical cartridges within the instrument 1001. The task scheduler is operable to control the movement, such as the transport and transfer of each of the analytical cartridges amongst the plurality of subsystems. In some embodiments, the time each cartridge spends in a subsystem may also be managed by the task scheduler. The task scheduler may reserve time on various subsystems as needed for analysis of each of the analytical cartridges. In some embodiments of the invention, the task scheduler may manage the movement of a cartridge (i.e., the steps/parameters of the analysis to be performed) by identifying the contents of the cartridge.

In some embodiments, the instrument 1001 may also include a reader operable to analyze unique identifiers (e.g., barcodes) on a cartridge. The contents of a cartridge and the required processing may be associated with a barcode on the cartridge. The instrument 1001 may read the unique barcode via a reader and associate the unique barcode with a particular set of instructions for the task scheduler to execute. The instrument preferably includes a computer (e.g., within or connected to interface 1003) to control operations described herein. The computer preferably includes a processor coupled to a non-transitory memory device. The memory preferably stores instructions executable by the processor to cause the system to manipulate analytical cartridges within the instrument 1001 and to obtain and process images of labelled microbes.

Processor refers to any device or system of devices that performs processing operations. A processor will generally include a chip, such as a single core or multi-core chip, to provide a central processing unit (CPU). A process may be provided by a chip from Intel or AMD. A processor may be any suitable processor such as the microprocessor sold under the trademark XEON E7 by Intel (Santa Clara, CA) or the microprocessor sold under the trademark OPTERON 10200 by AMD (Sunnyvale, CA).

Memory refers a device or system of devices that store data or instructions in a machine-readable format. Memory may include one or more sets of instructions (e.g., software) which, when executed by one or more of the processors of the computer can accomplish some or all of the methods or functions described herein. Preferably, the computer includes a non-transitory memory such as a solid state drive, flash drive, disk drive, hard drive, subscriber identity module (SIM) card, secure digital card (SD card), micro SD card, or solid-state drive (SSD), optical and magnetic media, others, or a combination thereof.

An input/output device is a mechanism or system for transferring data into or out of a computer to the instrument. Exemplary input/output devices include a video display unit (e.g., a liquid crystal display (LCD) or a cathode ray tube (CRT)), an alphanumeric input device (e.g., a keyboard), a cursor control device (e.g., a mouse), a barcode scanner, a reader, a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem. Input/output devices may be used to allow a user to control the instrument and display results and generate a report obtained from the analysis of the cartridges.

Thus the instrument may be used with a cartridge to perform methods of the invention for detecting a microorganism by mixing a sample with magnetic particles and fluorescent particles specific for binding to targets of interest; separating bound and unbound magnetic particles in the sample from the sample, wherein magnetic particles bound to targets separate from the sample; and detecting and counting targets by observing fluorescence from the fluorescent labels bound to the targets to show the presence of the targets in the sample. The mixing step preferably includes exposing the sample to magnetic particles and fluorescent particles that bind to targets of interest. The detecting step preferably includes imaging fluorescently labeled targets using digital imaging.

Targets of interest can be any type of cell or molecule. In certain embodiments, the targets comprise at least one of toxin A and toxin B of *Clostridium difficile*. In other embodiments, the targets comprise Lethal Factor, a subunit of Lethal Toxin, secreted from *Bacillus anthracis*. In some instances, targets are pathogens.

The present invention provides methods and kits for detection of targets, such as *C. difficile* toxins, that are more sensitive than commercial immunoassays, more rapid than the Cell Cytoxicity Neutralization Assay (CCNA), and more specific than nucleic acid tests. The technology can enumerate single targets with simple optical equipment, minimal sample preparation, and rapid turnaround time in a sample-to-answer format. It also demonstrates equivalence in performance to the highly sensitive toxin B cytotoxicity assay reference method used for regulatory clearance of *C. difficile* toxin tests.

The invention offers a novel method for rapid and sensitive detection of diagnostic markers directly in complex patient samples. As exemplified below, the analytical sensitivity of the 30 min *C. difficile* toxin B test in stool samples is found to be 45 pg/ml, which is more than 15 times more sensitive than the leading enzyme immunoassays (EIAs). Also, the accuracy of tested clinical samples is comparable to that of the CCNA. The unique dye-cushion format allows detection with minimal sample processing because it optically sequesters the sample and unbound label from the detection surface. Specifically, stool can be merely diluted in assay buffer and passed through a nylon mesh filter to remove large particulates before adding the assay reagents. The simple sample preparation, lack of wash steps, and elimination of stepwise addition of reagents offers the potential to eliminate significant hands-on time, lower cost, and simplify instrumentation when compared to other EIAs. Overall, this invention features a promising technology for the accurate and sensitive detection of *C. difficile* toxins and other targets, e.g., microbes and components thereof.

The invention is unique in its ability to rapidly and sensitively detect a broad range of analytes. In addition to detecting targets such as molecules, including but not limited to, toxins, nucleic acids, and biomarkers, the methods can also detect and count cellular pathogens (bacterial, fungi, and parasites), viruses, and diagnostically important human cells. The method described here can be used to simultaneously test a single sample for a variety of analytes including diagnostically informative human cells (for example, neutrophils), a toxin (for example *C. difficile* toxin B), a virus (for example, norovirus), and a biomarker (for example, a cytokine).

General methods, kits, and analyzers for carrying out the invention are described in WO 03/036290, WO 03/073817, WO 2010/036808, WO 2010/036827, and WO 2010/036829, the contents of each of which is incorporated by reference herein.

Methods of the invention employ labeled particles and magnetic particles that bind to targets of interest, e.g., a microbe, e.g., *C. difficile*, cell or component thereof, such as a secreted substance, e.g., *C. difficile* toxin A or toxin B, to form complexes.

The complexes are placed or formed in a liquid layer in a vessel. The method employs at least two liquid layers, the complexes are initially present in an overlying layer that is separated from the detection surface of the vessel by a cushion layer. The cushion layer is denser than the overlaying layer. The magnetic particles, whether unbound or in complexes, can be moved by a magnetic force through the overlying layer and cushion layer to deposit the magnetic particles and anything bound to them in a detection zone adjacent a detection area of the vessel. Unbound labeled particles, target, and other sample components remain in the overlying layer. The amount of target in the sample can then be detected by counting the number of labeled particles in the detection zone. In certain embodiments, the cushion can further include a dye that blocks signal generation or emission from unbound labeled particles in the overlying layer.

The method may also employ one or more controls. For example, the method may employ a positive control in which an aliquot of the sample is spiked with a known amount of target, such as a secreted substance, e.g., *C. difficile* toxin A or toxin B, to form complexes. The assay is then completed as with the unspiked sample. The positive control can be used to determine whether a component in the sample is inhibiting any part of the assay. As the positive control sample contains a known amount of target, the amount of target detected should be proportional to the amount spiked. If the amount detected is significantly lower than that expect, then it can be determined that the sample is interfering with the assay, and the assay of the sample is invalidated. For example, if the amount detected in the positive control is less than 95%, 90%, 85%, 80%, 75%, 70%, 65%, 60%, 50%, or some other fraction, of the expected amount, the assay of the sample may be invalidated. Of course, if more target is present in the sample than spike, the positive control will yield a higher amount of target than expected. Such samples are then not invalidated.

The method may alternatively or in addition include a neutralization control in which the sample is spiked with binding molecules that interfere with binding of the labeled particles and/or magnetic particles or both. The added binding molecule may be the same or different from those on the labeled and magnetic particles. The neutralization control can be used to determine a background count that is not specific for the target. This background can be subtracted from the amount detected in the sample assay. Alternatively, the amount from the neutralization sample can be used to set a threshold for determining a positive result. For example, for the assay sample to be considered positive, the amount of target detected may need to be greater than a threshold. Alternatively or in addition, for an assay sample to be considered positive, the ratio of the signal from the assay sample to the signal from the neutralization control may need to be greater than a threshold (or the inverse ratio may need to be lower than a threshold). In one example, the ratio of signal from the neutralization control to the signal from the sample assay is less than 0.75, 0.7, 0.65, 0.6, 0.55, 0.5, 0.45, or 0.4, e.g., less than 0.5, for a positive sample.

Furthermore, the assay requires no or minimal sample preparation. The invention simplifies test operation while delivering high sensitivity by employing detection and enumeration of individual labeled targets without requiring washing steps. Sample sources may range widely. Human samples can include for example urine, stool, blood, serum, plasma, saliva, nasal secretions, cerebral spinal fluid, skin, wound, and many others. Industrial samples can include food, beverages, and pharmaceuticals, and environmental samples can include water, air, or surface samples. In one embodiment, e.g., for *C. difficile* or other intestinal microbe, the sample is a stool sample (e.g., formed, semi-formed, or unformed) or samples derived from stool. For example, a stool sample may be diluted and filtered to remove large particulates.

Labeled particles may be any suitable particles known in the art, for example, labeled particles may be polystyrene, glass, or latex beads or quantum dots. Particles may be labeled by any detectable moiety, typically a optically detectable moiety, such as fluorophores, chemiluminescent agents, bioluminescent agents, resonance light scattering particles, light absorption or chromogenic signaling agents, quantum dots, or up-converting phosphors. Alternatively, particles may be natively detectable, e.g., optically. For example, particles may be detected by fluorescence, absorption, light scattering, phosphorescence, or luminescence. Magnetic particles are known in the art and include paramagnetic and superparamagnetic particles.

Labeled and magnetic particles can be provided in amounts that favor formation of complexes of one target, e.g., biomarker or molecule. This amount can be determined by providing an excess of the particles in view of the expected or maximum amount of target to be found in a sample. In this manner, the invention allows for counting of individual targets present in a sample by determining the number of labeled particles in the detection zone.

Binding molecules are known in the art and include antibodies or antigen binding fragments thereof or aptamers. Depending on the target, e.g., microbe, the binding molecule may also include ligands or other compounds that bind to cell surface receptors or markers.

The dye-cushion can include various density agents singly or in combination (and at various concentrations) including for example, sucrose, diatrizoate, iodixanol (tradenamed Optiprep®), NaCl, CsCl, Percoll®, metrizamide, or albumin. The density of the cushion layer may be of any suitable value, e.g., at least 1.01 g/ml, at least 1.05 g/ml, at least 1.1 g/ml, at least 1.2 g/ml, at least 1.3 g/ml or higher. The density of the layer may also be homogeneous or nonhomogeneous, e.g., a gradient. When a nonhomogeneous layer is present it can have an average density of at least 1.01 g/ml, at least 1.05 g/ml, at least 1.1 g/ml, at least 1.2 g/ml, at least 1.3 g/ml or higher. For example, hydration of a cushion by liquid from an overlying layer can lead to a density gradient in the cushion.

When the reaction medium is substantially transparent to excitation light or other illuminating light, as well as to reflected or emitted light producing the imaging signal, unbound labeled particles which are outside of the detection zone can contribute a large nonspecific optical signal to the image. Inclusion of a dye into the cushion can be used to eliminate or reduce the signal produced by unbound labeled particles residing outside of the detection zone. For example, dye at an appropriate concentration allows detection of fluorescence in the detection zone at or near the detection surface, while masking the signal from unbound labeled particles in the remainder of the vessel. When the signaling moiety is fluorescent, the dye used can have an absorbance of light overlapping the excitation or emission wavelengths of the fluorescent signaling moiety, or can absorb both exciting and emitted light. For example, dyes that are useful in the invention when the fluorescent signaling moiety is yellow-green in color include Chromotrope 2R and Acid Red 1. Many other dyes appropriate in this and other spectral regions are known to those familiar with the art, such as india ink or a Direct Black, such as 19 or 168.

The combination of the dense cushion layer and dye provides an efficient method for imaging labeled targets without washing. This approach can eliminate background signal due to unbound labeled particles and labeled entities other than the target. The cushion can ensure that only targets drawn through the dense layer by their association with magnetic particles reach the detection zone. The dye prevents the detection of signal due to the free labeled particles in the overlying bulk reaction mixture thereby isolating the signal of labeled targets complexed to magnetic particles deposited within the detection zone.

The cushion and dye may be employed in the methods in liquid or dried form. In one embodiment, the cushion, with or without dye, is in liquid form in a vessel and the sample (or control) is added over the cushion. In another embodiment, the cushion, with or without dye, is in dried form in the vessel, and addition of liquid hydrate the cushion. Advantageously, a dried cushion, with or without dye, may be hydrated by liquid from the sample (or control). When the sample (or control) is added to the vessel, liquid from the sample (or control) hydrates the dried reagents to form the cushion layer which then separates the rest of the sample from the detection surface.

The methods employ one or more vessels with a detection surface or detection area onto which labeled targets are deposited by selection for subsequent detection. Vessels typically have properties and features that support optical detection of labeled targets. These properties and features may include optically appropriate materials, geometries, and fiducial features for focusing.

In general, the face of the vessel that includes the detection area is optically transparent with properties that are well-suited for detecting the labeled particles used to label the target. For example, if fluorescence is to be detected, the optical window should be non-fluorescent at wavelengths in the corresponding spectral regime of the target. The vessel would also have low reflectance of incident light at specific wavelengths that might also interfere with imaging by increasing background signal.

The image surface may be protected against dust, scratches, and contamination. This may be beneficial in limiting nonspecific background or artifacts that may complicate imaging. Some means of protecting the surface include incorporating physical standoffs, feet, or barriers, or by covering the optical surface with a foil or plastic cover. Alternatively, a door that is hinged or slides can be used to protect the surface. These protective features can be removed before imaging occurs or can be removed automatically during imaging. Alternatively, these features might not be mobile features, as would be the case with protective or scratch-resistant coatings.

The vessel or detection surface can be a plastic such as a cyclic olefin copolymer, acrylics, polystyrenes, and other transparent materials. It can also be fabricated from glasses such as borosilicate glass, fused silica, quartz, or others. Other materials include, but are not limited to, PDMS, RTV, optical adhesives, and laminates. The vessel or detection surface may have built in optical filtering functionality which may include a coating or structural composition, such as a laminate or additional physical layer that block or absorb certain wavelengths of energy.

Detection may be by use of an array photodetector, e.g., CMOS or CCD. The detector may be sized to detect the entire detection zone in a single image. The detection may also not employ optical magnification or employ optical magnification of 5× or less. Typically, the method employs large area detection. For example, the detector will typically detect an area with at least one cross-sectional dimension of 1 mm, e.g., at least 1 cm.

By washing is meant a process for physically removing, from a container, liquid containing undesirable components from targets, which, in contrast to the undesired components, are either retained in the container.

By a test not requiring washing is meant a test in which targets are detected without using wash steps.

By cushion, density cushion, liquid cushion, cushion layer, or liquid density cushion is meant a substantially liquid layer which is denser than the overlying layer. In the invention, the cushion is found in a vessel lying between the detection surface and the liquid layer including the sample and test reagents, prior to selection. This cushion provides a physical separation between the test's reagents and the detection surface. Using selection, labeled particles and targets complexed with magnetic particles are moved through the cushion and deposited in the detection zone. Labeled particles that are not complexed with a magnetic particle are excluded from the detection zone by the dense liquid layer of the cushion.

By dye is meant a substance or mixture added to the reaction that interferes with the production or transmission of light to or from labeled particles. The dye reduces or eliminates signal originating outside of the detection zone while allowing detection of the signal derived from labeled particles within the detection zone. For fluorescent labeled particles, dyes can absorb light of the fluorescent excitation frequencies, the fluorescent emission frequencies, or both. Various dye properties can be useful for this purpose including light scattering and absorbance. In various embodiments, the dye reduces signal by at least 50%, 75%, 85%, 90%, 95%, 99%, or even more than 99%.

By dye-cushion is meant a cushion that includes dye. The dye-cushion simultaneously provides a physical exclusion of the bulk reaction from the detection zone (as a function of the density of the dyed cushion) while preventing or reducing the transmission of signal from the overlying reaction to the detector (as a function of the dye included in the dense layer).

In some embodiments, by target is meant a microbe, e.g., *C. difficile*, or component thereof, e.g., secreted product, such as *C. difficile* toxin A or toxin B, that is potentially present in a sample and the presence of which is tested by the invention. The term also includes cells from multicellular organisms, e.g., mammals such as humans, and components thereof.

By binding molecule is meant a molecule or molecular complex that specifically binds to a target. Examples of binding molecules are antibodies, antigen binding fragments thereof, and aptamers.

By particle is meant a matrix which is less than 50 microns in size. The size of a population or batch of particles is defined as the mean measurement of the longest pair of orthogonal dimensions for a sample of the particles. Many particles have some characteristics of a solid. However, molecular scaffolds or complexes, which may not be rigid, are also defined as particles. For example, dendrimers or other branching molecular structures are considered to be particles. Similarly, liposomes are another type of particle. Particles can be associated with or conjugated to signal elements. Particles are often referred to with terms that reflect their dimensions or geometries. For example, the terms nanosphere, nanoparticle, or nanobead are used to refer to particles that measures less than 1 micron along any given axis. Similarly, the terms microsphere, microparticle, or microbead are used to refer to particles that measure less than one millimeter along any given axis. Examples of particles include latex particles, polyacrylamide particles, magnetite microparticles, ferrofluids (magnetic nanoparticles), quantum dots, etc.

By fluorescent particle or labeled particle is meant a particle that can specifically bind to targets and generate a signal.

By a roughly planar surface or substrate is meant a surface that can be aligned in parallel to an imaginary plane such that when the distance is measured from points in any 1 mm×1 mm square on the surface to the closest points on the imaginary plane, the absolute value of the mean distance is less than 50 micrometers.

By detection surface is meant the surface of a roughly planar substrate. The detection surface is transparent to the signal of the labeled particles.

By detection area is meant the area of the vessel that is simultaneously analyzed by the invention. The detection area is typically greater than 1 mm, e.g., greater than 5 mm, 10 mm, or 15 mm, in its longest linear dimension. For example, the section of a glass slide that is simultaneously imaged by an optical device that includes a collection lens and a CCD chip might measure 0.8 cm×0.5 cm. The detection area is then 0.4 $cm^2$.

By detection zone is meant the volume in which targets can be detected. The detection zone has the same cross-sectional dimension as the detection area but has a depth corresponding to the depth in which a labeled particle can be detected and identified. The depth of the detection zone is therefore dependent on the threshold criteria used to score for positive signal. When optical detection is used, the depth of the detection zone is dependent on the optical depth of field.

By simultaneously detecting targets in a section of the detection area is meant detection of the signal from a section of a roughly planar detection surface in one step.

By sample is meant material that is scanned by the invention for the presence of targets.

By photoelectric detector is meant a man-made device or instrument that transduces photonic signals into electric signals. Examples of photoelectric detectors include CCD detectors, CMOS detectors, photomultiplier tube detectors, and photodiode detectors, e.g., avalanche photodiodes.

By illuminating is meant irradiating with electromagnetic radiation. Electromagnetic radiation of various wavelengths can be used to illuminate. It includes, for example, radiation with wavelengths in the X-ray, UV, visible, or infrared regions of the spectrum. Note that illuminating radiation is not necessarily in the visible range. Illuminating preferably occurs with the range of 190 to 1100 nm.

By microbe is meant a single celled organism, e.g., bacterium, protist, archaebacterium, or fungus, or a virus.

Figure 5:
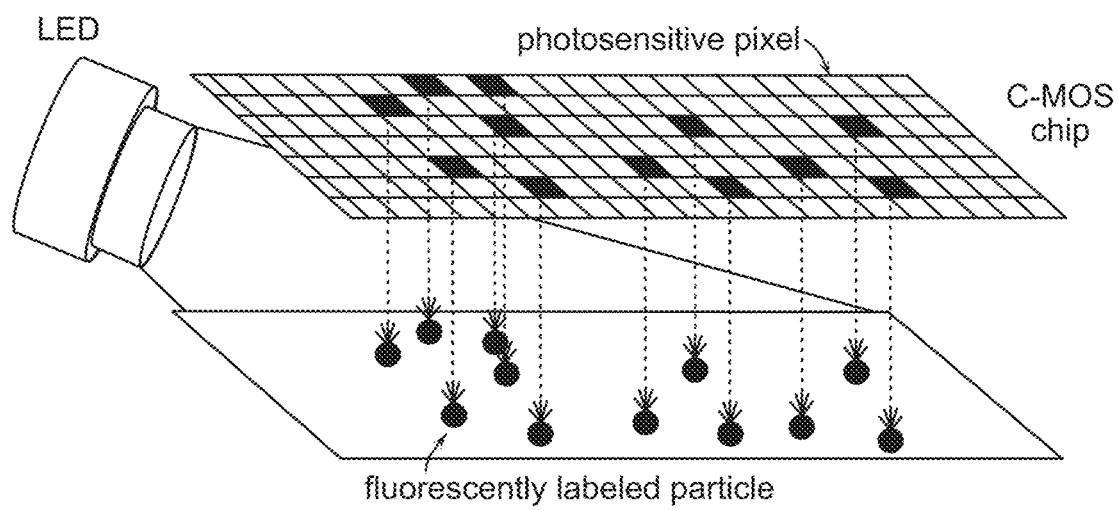
FIG. 5 shows a schematic representation of the invention.
Figure 6:
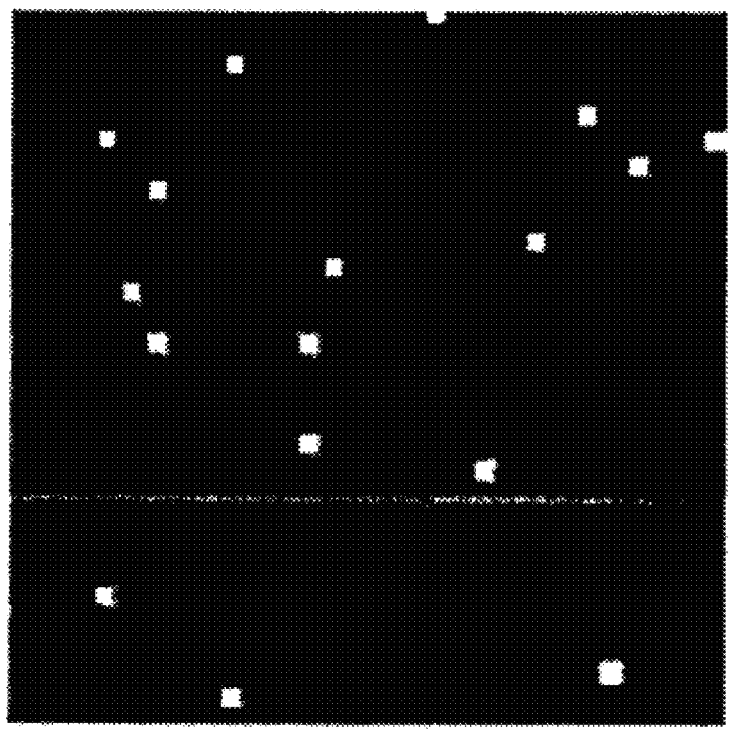
FIG. 6 shows a non-magnified image from the *C. difficile* toxin B test showing individual microscopic fluorescent particles that have been tethered by toxin B molecules to magnetic particles, drawn through the dye-cushion, and deposited on the detection surface.
Figure 7:
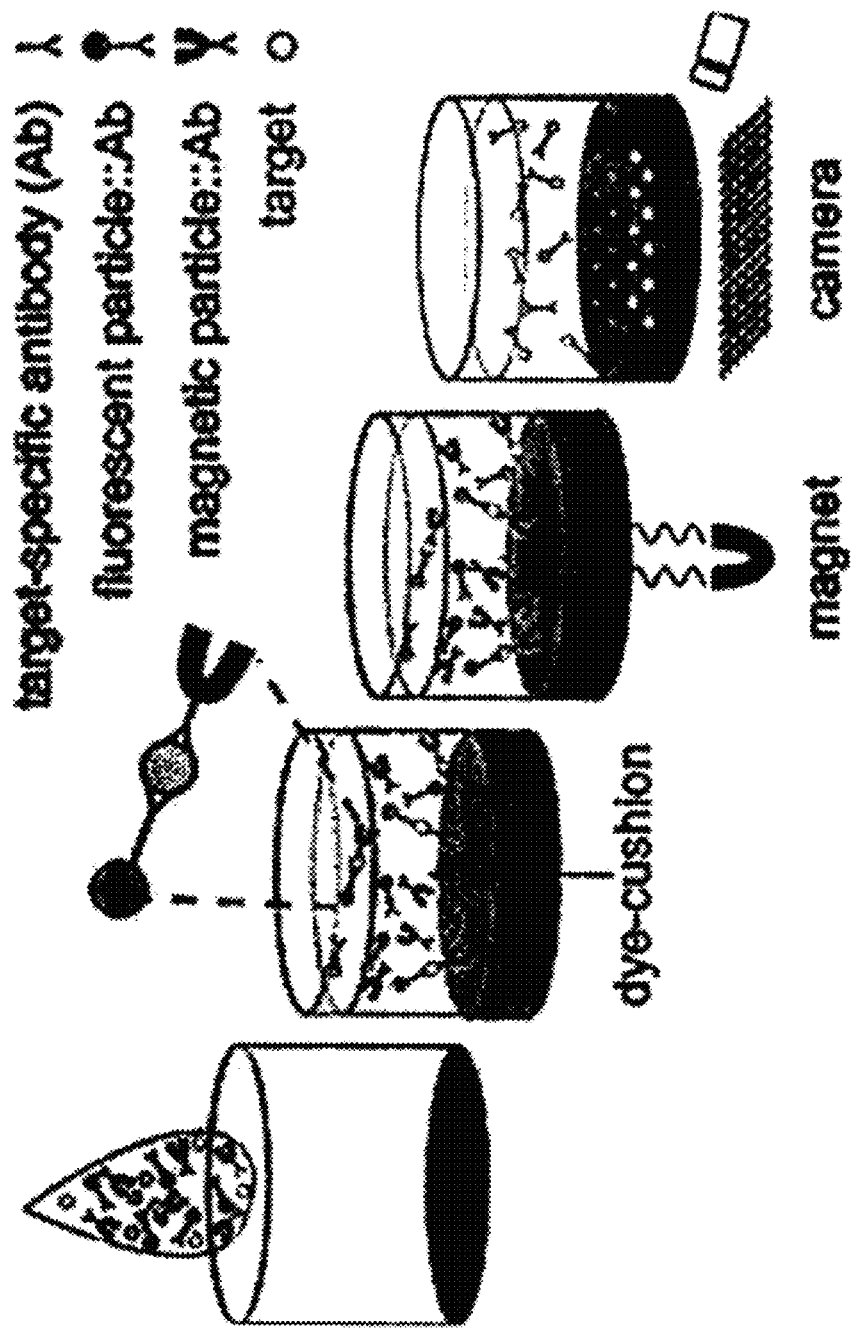
FIG. 7 is a figure depicting how the dye and cushion in the assay's vessel eliminates the need for wash steps.
Figure 8:
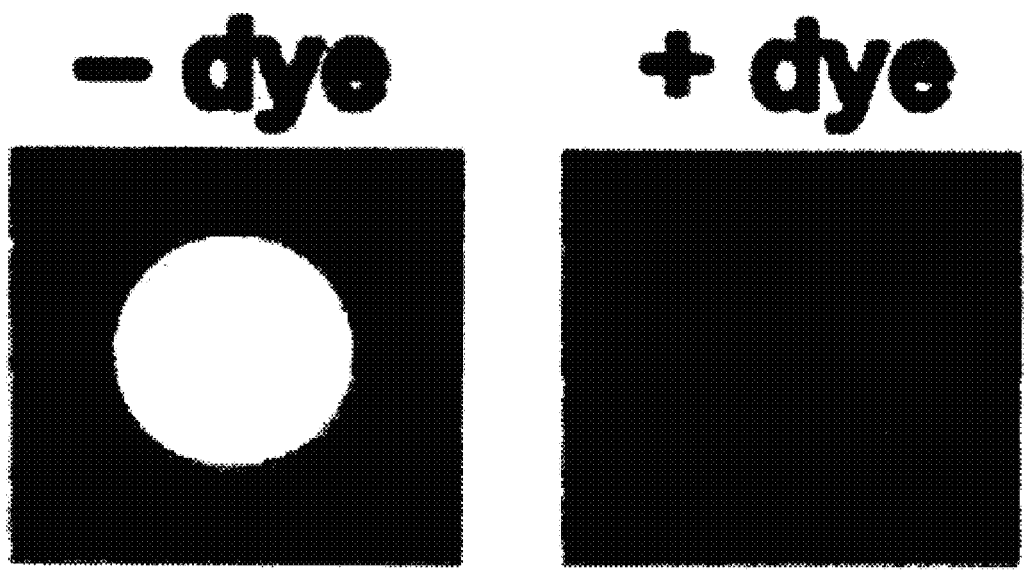
FIG. 8 shows images of wells containing unbound particles overlying cushion layers with or without dye, demonstrating the effectiveness of the dye and cushion for eliminating background from the unbound fluorescent particles.

In one embodiment, the method achieves single molecule counting and counts individual targets without magnification. FIG. 5 shows how the methods detect targets tagged with fluorescent nanoparticles without using magnification. Illuminating the fluorescent particle-tagged targets causes the labeled targets to emit photons. The photons impinge on a CMOS chip in a digital camera (like the one in cell phones) containing an array of independent photosensitive pixel elements. Thus, pixel elements lying directly above the individual targets "light up" as white spots in the resulting image (FIG. 6). The invention features a dye-cushion layer that allows the method to rapidly and specifically count targets, e.g., microbes, or a component thereof, e.g., *C. difficile* toxin molecules in a complex stool sample with minimal sample preparation (FIG. 7). A liquid sample potentially containing the target is added to a clear-bottomed vessel that contains two types of dried reagents: a dye (e.g., Direct Black) and a density agent (OptiPrep). Dried dye-cushion reagents at the bottom surface of the vessel form a dense layer when hydrated. Target-specific fluorescent and magnetic nanoparticles are stabilized in a small lyophilized ball (~1 mm diam.). The magnetic nanoparticles are coated with antibodies specific to one antigenic site on the target, e.g., microbe, or component thereof, e.g., *C. difficile* toxin molecule, and the fluorescent nanoparticles are coated with complementary antibodies binding to a distinct antigenic site on the same target. Upon hydration of the dried reagents by the sample, two layers form: the dense dye-cushion layer and the assay layer. In the assay layer, the target molecules bind to the magnetic and fluorescent nanoparticles, tethering them together. The high concentration (~109/ml) and small size (200-500 nm) of the particles drive rapid binding kinetics with diffusive mixing only, which simplifies the instrumentation by eliminating the need for mechanical mixing functionality. Placing the vessel, or cartridge, over permanent magnets for 3 minutes draws the magnetic particles—and any fluorescent particles that are tethered to them via target molecules—through the dye-cushion layer, depositing them in the detection zone. The captured fluorescent particles are imaged and counted instantaneously with non-magnified digital imaging. A computer instantaneously enumerates the illuminated pixels indicating the number of targets present. At low analyte concentrations, digitally counting individually labeled targets generates a better signal to noise ratio compared to the more common method of integrating the signal across the detection area. Non-magnified imaging allows a large field to be imaged in an instant—allowing for a small number of targets to be rapidly detected in large volume of sample. A key technical advantage arising from the method's innovative non-magnified digital imaging approach is the technology's ability to detect very low levels of targets quickly and with very low-cost components. Because a single molecule can tether a fluorescent particle to a magnetic particle at low target concentrations, counting the number of magnetically deposited labeled particles corresponds to the number of captured target molecules. The dye-cushion eliminates or reduces sample prep and wash steps. FIG. 8 shows that the dye-cushion completely blocks the intense fluorescence of the tens of millions of highly fluorescent unbound particles.

The dye-cushion layer passively forms a dense colored layer that absorbs both the excitation and emission wavelengths of light. This layer prevents light from reaching the unbound fluorescent particles in the assay layer (there are millions, and they would otherwise be very bright). Similarly, the dye-cushion optically and physically sequesters the sample from the detection surface, making the assay robust to even the most difficult sample matrices without requiring extensive sample preparation by the user.

In addition to the methods discussed above, the methods may be employed as a competitive assay, where the magnetic particles are conjugated to target competitors. At least two types of complex are formed, one complex forms between the magnetic particles and labeled particles, and another complex forms between the target and either the magnetic particles or the labeling particles. When present, the target reduces the number of complexes formed between the magnetic particles or the labeling particles by binding to one of the particles and preventing it from binding to the other particle. The detection of the target occurs indirectly by a reduction in the amount of complexes of the magnetic particles and the labeling particles formed in the absence of the target. As will be understood, thresholds for determining a positive result or a valid assay from controls will be inverted in a competitive assay.

The invention also provides kits for carrying out the methods described herein. The kits include labeled particles, magnetic particles, and a liquid cushion reagent or dried reagents that form a cushion on hydration. The kits may further include a vessel, or cartridge, having a detection surface, with the liquid or dried cushion reagent optionally stored in the vessel. Kits may further include a dye, e.g., mixed with the liquid or dried cushion reagents or stored separately. Kits may further include reagents required for a positive control, e.g., a predetermined amount of target, typically purified, and/or a neutralization control, e.g., free binding molecules.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

The invention is described with respect to the following non-limiting embodiments. In particular, although the examples illustrate detection of *C. difficile* toxin B, the methods may be employed with other targets. Unless otherwise noted, any element of a device specifically described in the examples may be employed generally with a device or kit of the invention.

Reagents. Fluorescent microparticles (500 nm) were purchased from Thermo Fisher Scientific (Waltham, MA). Polystyrene carboxylate magnetic particles (292 nm) were purchased from Ademtech (Pessac, France). Magnets for capturing magnetic particles were from Dexter Magnetic Technologies (Elk Grove, IL). Microtiter plates (96 well clear bottom, half area black plate) were from Greiner Bio-One (Monroe, NC). Native Toxin B standard purified from *C. difficile* (ribotype 087) was purchased from List Laboratories (Campbell, CA). Mouse monoclonal antibodies raised against *C. difficile* toxin B were from BBi Solutions (Cardiff, UK) and Fitzgerald (Acton, MA). Heterophilic blocker (HBR-11) was from Scantibodies (Santee, CA). Bovine serum albumin (BSA), Casein, Casein acid hydrolysate (Hy-Casein SF), Trizma® base, Trizma®-HCl, 1-Ethyl-3-(3-dimethylaminopropyl) carbodiimide (EDC), N-hydroxysuccinimide (NHS), Triton X-100 and OptiPrep were from Sigma-Aldrich (St. Louis, MO). Direct Black 19 was from Orient Corporation (Cranford, NJ). Protease inhibitor cocktail was from Takara Bio (Mountain View, CA).

Clinical Samples. De-identified discarded stool samples were obtained from Beth Israel Deaconess Medical Center (Boston, MA) and Discovery Life Sciences (Los Osos, CA). The samples were collected over a period of 12 months. We excluded formed stool samples (either semi-sold or solid) and samples from children under age of 2. Samples were stored at 4° C. for 3-7 days in the clinical microbiology laboratory and the samples were transferred to our laboratory in a cooler with ice or ice-packs to maintain>4° C. After receiving the samples, they were diluted to 40% with water and single use aliquots were made and then stored at −80° C. until use. A pooled negative stool sample was made from 14 individual stool samples that had been scored as *C. difficile* negative by real-time PCR. Stool diluent was added to the samples, prior to testing, so that the final composition in assay mixture was 8% stool, 4 mg/ml Casein, 8 mg/ml Hy-Casein SF, 50 mM Tris-HCl, pH 7.3 supplemented with 1 mg/ml HBR-11 and Protease inhibitor cocktail at a 1:150 dilution. The diluted stool samples were filtered through a 10 micron nylon mesh filter (PluriSelect, San Diego, US) prior to testing to remove particulates.

Imaging System. The imaging system is a custom-built instrument and software that is capable of automatically capturing image data from selected wells of a microtiter plate. it uses a high precision linear stage from Prior Scientific (Rockland, MA) to position each well over a fluorescence-based image acquisition subsystem. The instrument can image in 4 separate color channels and uses an objective lens, illumination LEDs, fluorescent filter sets, and camera. The objective lens has a field of view designed to capture the image of an entire microtiter plate well. The illumination module light source consists of 2 high power LEDs per color channel. A series of fluorescent image frames are captured with a camera using a 3.1 MP Sony IMX265 monochrome sensor with 12-bit per pixel quantization. The final image for each well is then formed by summing multiple frames. For the *C. difficile* toxin B tests, we used 470/40 nm excitation and 515/30 nm emission filters and captured 2 frames at a 20 msec exposure.

Preparation of Microtiter Plates Containing Dye-Cushion. Dye-cushion was prepared by adding 50 µL of a solution containing 0.25 mg Direct Black 19, 10% (v/v) OptiPrep in 50 mM Tris-HCl, pH 7.5 to each well of a surface-plasma-treated 96-well microtiter plate and drying at 60° C. for 3 hours. Dried plates were stored desiccated for up to 1 month.

Preparation of Antibody-Conjugated Magnetic and Fluorescent Particles. Anti-toxin B monoclonal antibodies were conjugated to magnetic and fluorescent particles through a carboxyl linkage (EDC/NHS chemistry) using standard conjugation methods recommended by the particle manufacturers (Ademtech, PESSAC, France and Thermo F1Sher Scientific, Waltham, MA), The conjugated magnetic particles were quantified by visible light absorption and the conjugated fluorescent particles were quantified using flow cytometry for the purposes of subsequent assay formulation.

C. *difficile* Toxin B Test. To prepare the assay mixture, stool was diluted to 8% with a mix of stool diluent, 7e8 particles/ml of antibody conjugated magnetic particles, 1.1e7 particles/ml of antibody conjugated fluorescent particles, and the Indicated amount of toxin B (diluted in 50 mM Tris-HCl, pH 7.8 buffer containing 2 mg/ml BSA, 0.05% w/v Tween-20 and 0.05% v/v Proclln•300) or just buffer for blank. 100 µL of the assay mixture was pipetted in to each dried dye-cushion-containing well. Following a 30-minute incubation at 35° C., magnetic particles were pulled down by placing the assay plate on the Dexter magnet for 3 minutes. The plate was then imaged using the imaging system, and the signal was quantified as described below.

Image Analysis. The number of fluorescent particles were quantified for each acquired image as follows. The image was masked with a fixed pixel threshold creating a binary image where all pixels with intensities above the threshold are set to 1. Pixels from the image were grouped using connectivity analysis such that each active pixel was grouped with all active pixels that were immediately adjacent in either the x or y image direction. A pixel group, or blob, was then processed to determine a set of parameters such as area (number of pixels), blob intensity (total Intensity of all pixels in a blob) and compactness $$\left(\frac{perimeter^2}{4\pi area}\right).$$

The list of blobs was then filtered to remove non-specific signal which could be caused by the sample matrix. This was done by removing blobs based on size, intensity, and/or irregular shape. Once the blob list was filtered, the total blob intensity was computed by summing the intensity of each blob. The number of detected fluorescent particles was then computed by dividing the total blob intensity by the reference intensity of a single fluorescent particle.

Limit of Detection, Limit of Blank, Dynamic Range, and Precision Profile. These measurements were performed using the pooled negative stool sample. The limit of detection for the C. *difficile* toxin B test was determined by running 24 replicates of sample with no analyte and 12 replicates each of 7 toxin B concentrations. The limit of the blank, limit of detection, and precision profile were determined according to Clinical & Laboratory Standards Institute (CLSI) guidelines.

Testing C. *difficile* Clinical Samples. 320 clinical samples were tested as described above using a 3 well assay (test, positive control, and neutralization control for each sample). Each sample examined was tested independently by two operators. For the positive control, assay mixture inclusive of patient sample was spiked with 100 pg/ml C. *difficile* toxin B to detect matrix inhibitory effects. For the neutralization control, the assay was spiked with 2.5 µg/ml C. *difficile* anti-toxin B antibodies to confirm that any signal in the un-neutralized sample was a result of toxin B detection.

Cell Cytotoxicity Neutralization Assay (CCNA). An aliquot of sample that have been used for testing was sent frozen on dry ice to Microbiology Specialists Inc. (Houston, TX) for CCNA. On receiving, the integrity of the sample was checked, and CCNA was performed using MRC-5 fibroblasts cells and Quidel cytotoxicity reagents (Quidel, Catalog number: 03-05000). 5-fold using specimen diluent and centrifuged at 2000 to 6000×g for 10-minutes to pellet solid material. The supernatant was filtered through sterile 0.45 micron membrane filter was used for inoculating tissue culture plate with appropriate controls and the plate was incubated 35° C. for 24-48 hours. Specific cytopathic effect development was observed under 24 hours for positive samples while negatives samples were held for up to 48 hours.

Data Analysis. Data were analyzed using JMP and Graph Pad Prism software. Confidence intervals were determined using Clopper-Pearson analysis.

Example 1: Detection of C. *difficile* Toxin B in Samples

The method detects molecules labeled with fluorescently dyed nanoparticles using digital imaging without magnification. Illuminating the fluorescent nanoparticle labels causes them to emit photons which are collected using a 1:1 f/4 relay lens. The light emitted by a particle impinges on a small cluster of pixels on the CMOS chip of a digital camera forming white spots in the resulting image. At low analyte concentrations, digitally counting individually labeled targets generates better signal to noise ratios compared to simply integrating the signal from the entire detection area. Non-magnified imaging allows a large field to be imaged, enabling detection of a small number of target molecules in a large volume of sample in milliseconds.

Samples were first mixed with a diluent and target-specific immunoreagents, which consisted of fluorescent and magnetic particles coated with complementary antibodies specific for C. *difficile* toxin B. The assay mixture was then added to a clear-bottomed microtiter well, the bottom of which had been coated with a dried dye-cushion reagent. The dye-cushion reagent was a mixture of a dye that absorbs visible light (Direct Black 19 in these experiments) and a density agent, iodixanol (OptiPrep™). The dried dye-cushion reconstituted following addition of the assay mixture and formed a dense opaque aqueous layer underneath the assay layer. Light could not penetrate the dye-cushion layer to the assay layer. This feature optically sequestered unbound fluorescent labels and sample matrix from the detection surface. Therefore, the dye-cushion eliminated the need for laborious sample preparation and wash steps required in other immunoassay formats to eliminate background signal from unbound label and sample matrix components.

Example 2: Estimating the Analytical Performance

Figure 9:
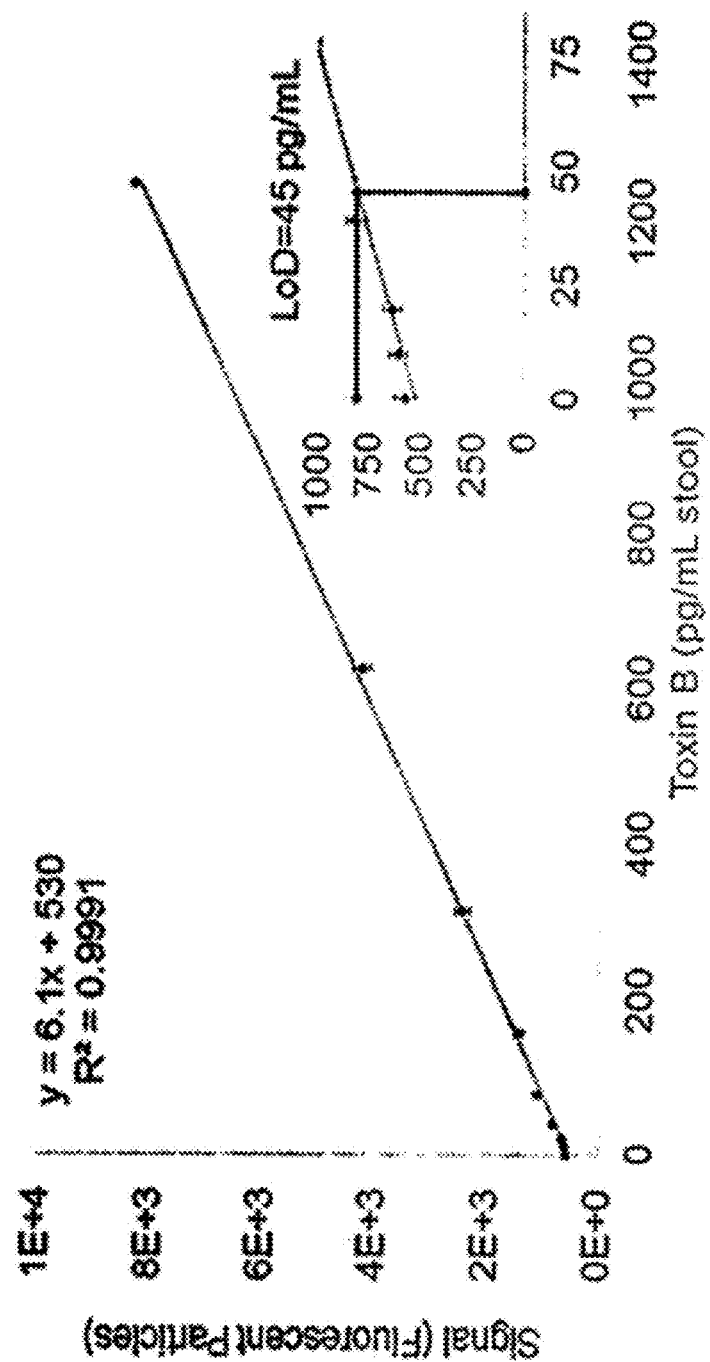
FIG. 9 depicts the analytical sensitivity of the *C. difficile* toxin B test.
Figure 10:
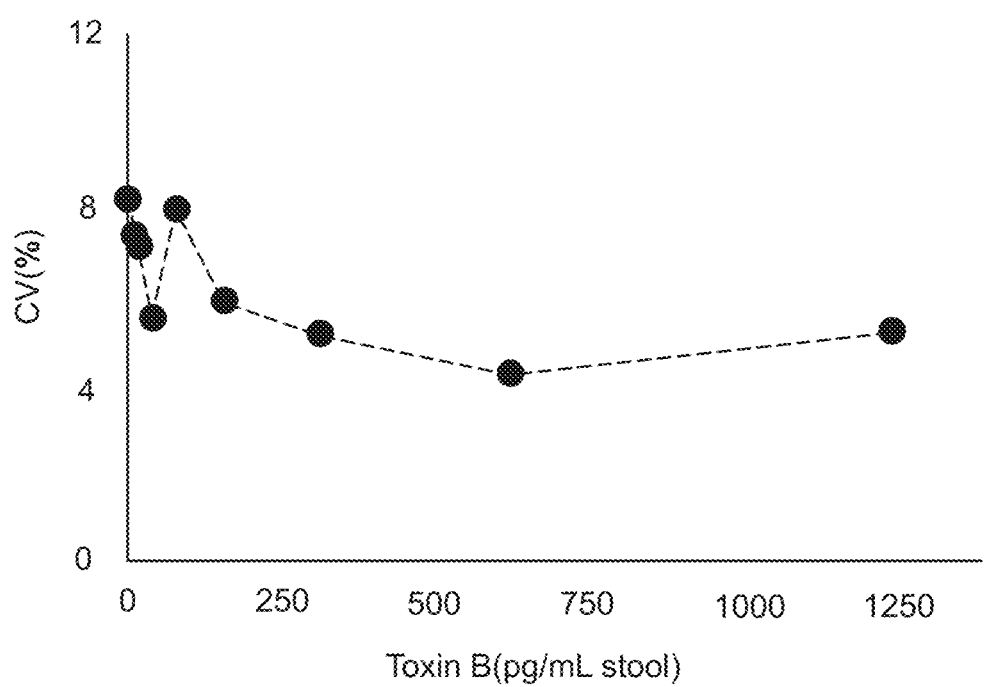
FIG. 10 depicts the assay precision profile of the *C. difficile* toxin B test.

To estimate the analytical sensitivity of the C. *difficile* toxin B test in stool matrix, a pooled stool sample was used, which included 14 randomly chosen clinical samples that gave negative results when tested by a real-time PCR C. *difficile* test. The pooled sample spiked with C. *difficile* toxin B was tested in a series of two-fold dilutions. The method delivered a limit of detection of 45 pg/ml for C. *difficile* toxin B (FIG. 9). Similar results were also observed when a different pool of PCR negative stool samples was used. At a toxin B concentration of 45 pg/ml, the reaction contained approximately 100-fold excess of magnetic particles compared to the number of toxin B molecules. At this analyte concentration, magnetic and fluorescent particles must, on average, be tethered together by single toxin B molecules confirming that the method detects single molecules by imaging without using magnification. Furthermore, the precision profile in FIG. 10 shows coefficients of variation (CVs) below 10% for the data shown in FIG. 9, demonstrating the method's potential for delivering reproducible results at low concentrations of toxin B.

Figure 11:
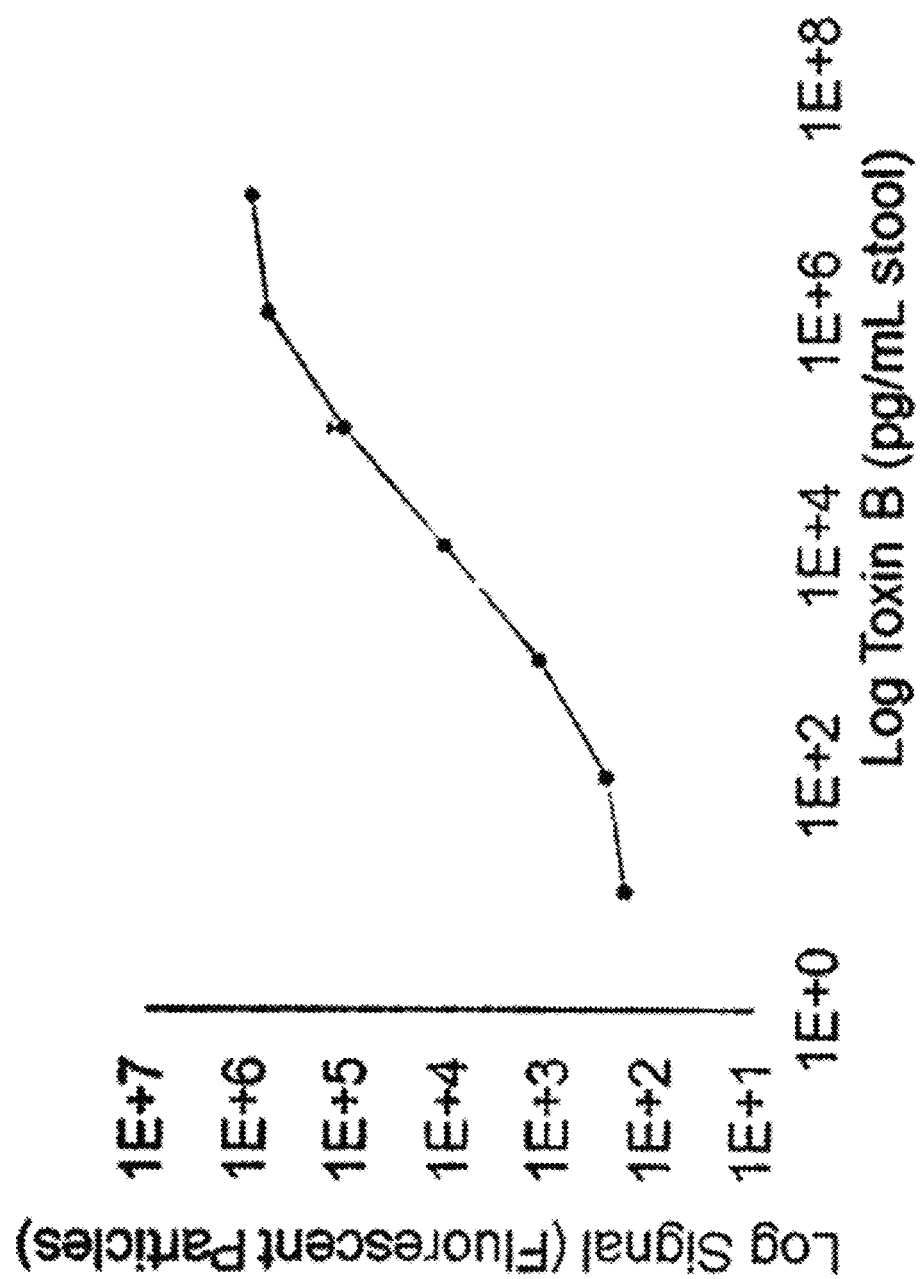
FIG. 11 depicts the dose response and dynamic range of the *C. difficile* toxin B test.

FIG. 11 shows the *C. difficile* toxin B test dose response in a pooled stool sample containing a range of concentrations of exogenously added purified *C. difficile* toxin B. The data were essentially linear over a concentration range of 4-5 orders of magnitude up to approximately 1 µg/ml, above which the response plateaus. It is noteworthy that covering this range exceeds the highest levels of *C. difficile* toxin B reported clinically, about 100 ng/ml.

Example 3: Detection and Mitigation of Matrix Effects by Assay Controls

Positive and neutralizing assay controls were designed to facilitate detection and subsequent mitigation of sample matrix effects. The assay controls and the toxin B test were performed in parallel on equal aliquots of a mixture containing clinical sample and assay reagents. The positive control includes a defined amount of spiked toxin (100 pg). A deviation of the positive control signal that is lower than the expected result indicates negative assay interference (assay inhibition). The neutralization control contains toxin B neutralizing antibodies that sequesters toxin B in the clinical sample, making it undetectable in the assay. In this way, the neutralization control distinguishes specific signal derived from toxin B in the sample from non-specific signal. Non-specific signal can result from analyte-independent deposition of either fluorescent particles or auto-fluorescent sample components on the detection surface. In this work, a training set of clinical samples was used to empirically establish signal, neutralization, and interference thresholds for optimizing diagnostic accuracy relative to the cytotoxicity assay reference method.

Figure 12:
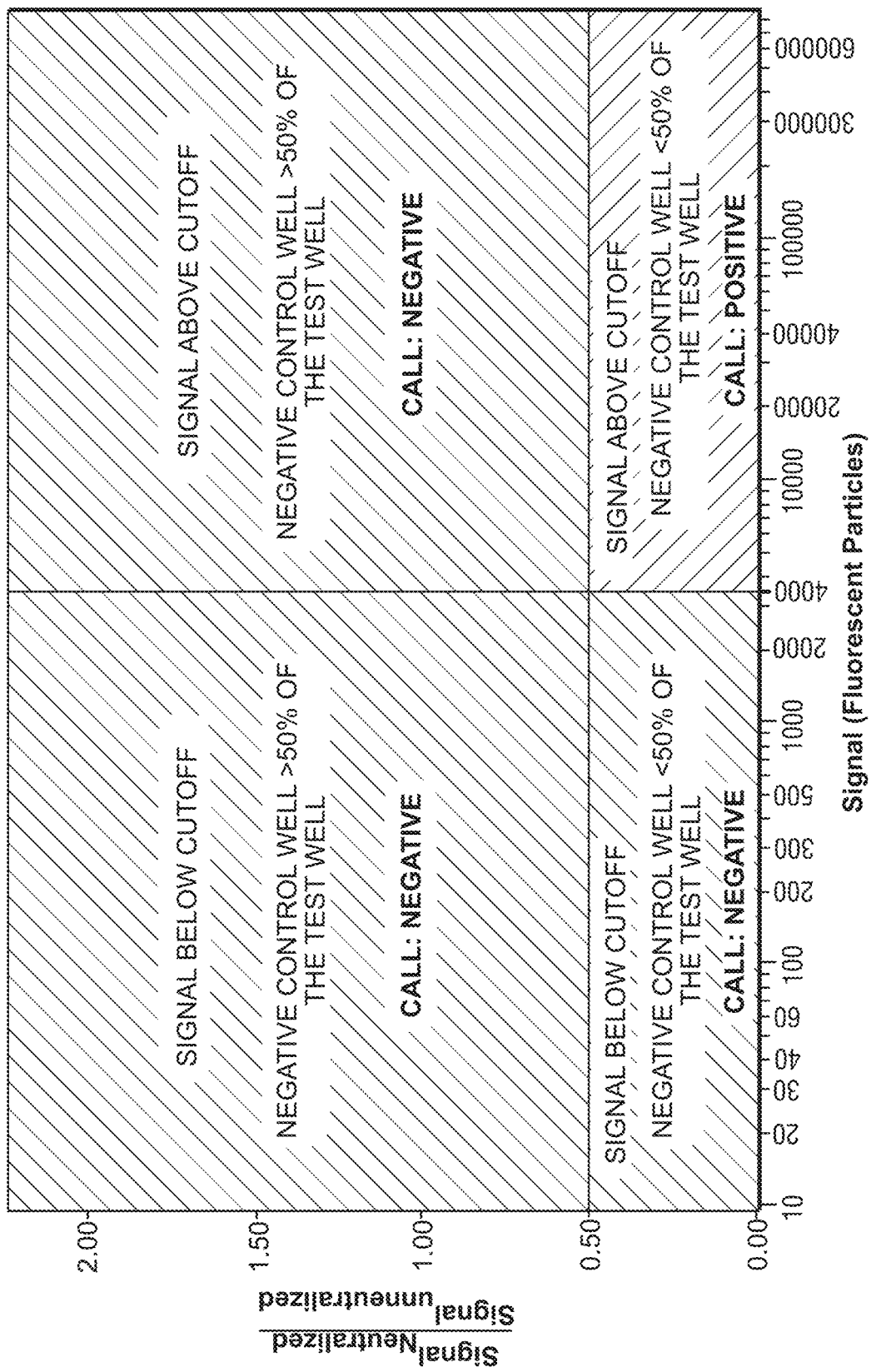
FIG. 12 is a graphical representation of the thresholds for calling positives in *C. difficile* toxin B test using clinical samples.

FIG. 12 graphically demonstrates the decision matrix for positive and negative calls by the *C. difficile* test. The decision matrix is comprised of 2 thresholds, a signal threshold (on the x-axis) and a neutralization threshold (on the y-axis). Only samples that exceed the signal threshold as well as the neutralization threshold are called positive. This is visualized as positive calls in the lower right-hand quadrant in FIGS. 12 and 13, and negative calls for the other three quadrants. In addition, if interference is detected in the positive control (>75% change compared to the expected signal) the sample is declared invalid.

Example 4: Accuracy of the *C. difficile* Toxin B Test on Clinical Samples

The *C. difficile* toxin B test was used to analyze 320 clinical stool samples from patients suspected of having *C. difficile* infection. Samples were tested in duplicate. The results from this sample training set were compared to the results of the toxin B cytotoxicity assay reference method. Receiver Operator Curve analysis was used to empirically develop assay thresholds for optimizing accuracy. Of the 320 clinical samples, only one sample (both replicates) was rejected from this analysis because it showed more than 98% inhibition of the positive control.

Figure 13:
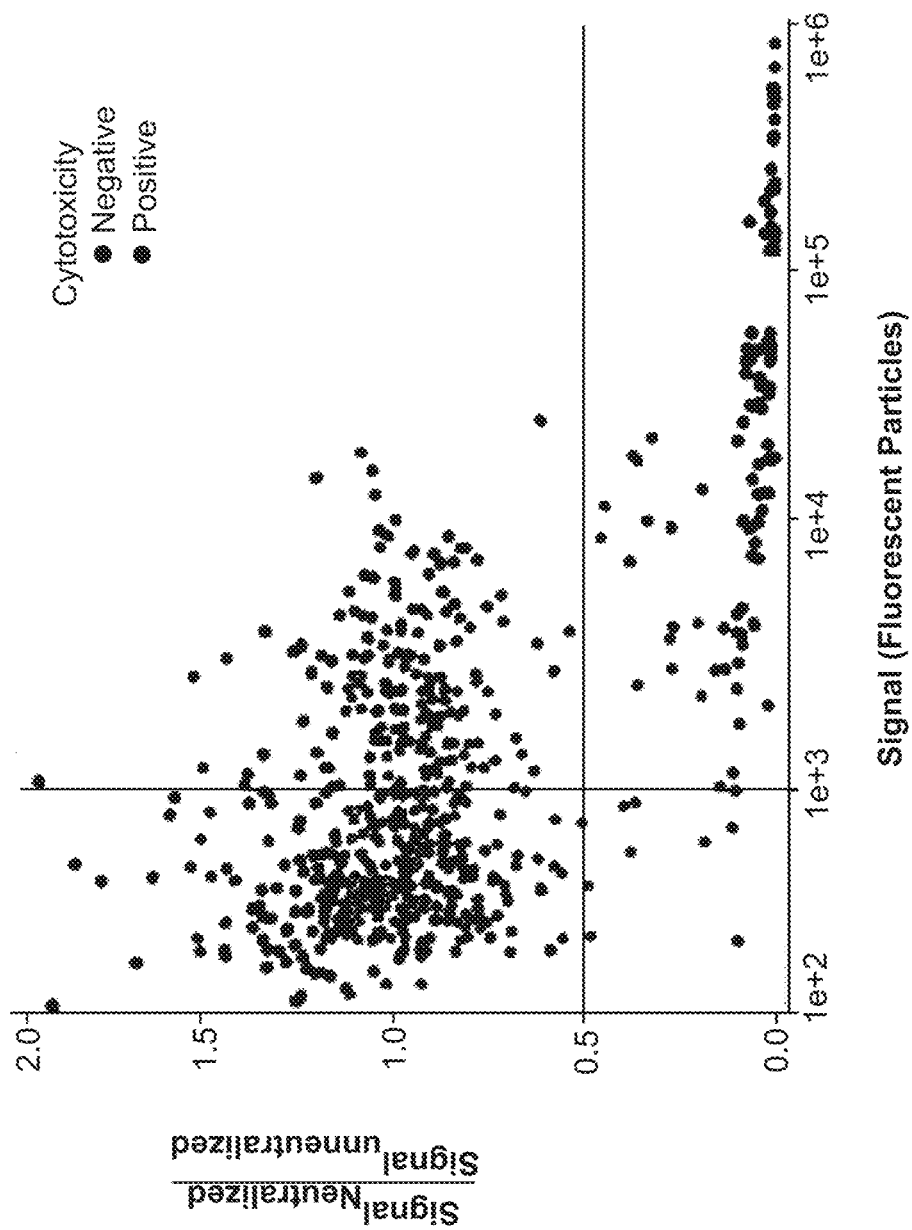
FIG. 13 depicts the results of *C. difficile* toxin B test using clinical samples.

FIG. 13 plots the training set results. The data illustrates that the chosen thresholds effectively distinguish positive and negative samples. Samples that scored positive using the cytotoxicity assay (red dots) fall almost entirely within the lower right-hand quadrant, representing samples with significant neutralizable signal. In contrast, samples that scored negative by the reference test (blue dots) fall almost entirely in one of the other three quadrants representing results that have either low signal, non-neutralizable signal, or both.

Table 1 compares the results of the *C. difficile* toxin B test to the reference cytotoxicity assay.

TABLE 1

*C. difficile* toxin B test compared to cytotoxicity assay (Microplate)

|  |  | Cytotoxicity Assay | |
|---|---|---|---|
|  |  | Positive | Negative |
| Multipath Assay | Positive | 96 | 9 |
|  | Negative | 3 | 530 |
|  |  | Sensitivity | 97.0% |
|  |  | Specificity | 98.3% |
|  |  | Accuracy | 98.2% |

Using the chosen thresholds, the new method presented here achieved 97.0% sensitivity (95% Cl, 91.4-99.4%); 98.3% specificity (95% Cl, 96.8-99.2%); and 98.2% accuracy (95% Cl, 96.7-99.0%) when compared to the cytotoxicity assay reference method.

Example 5: Improving Performance of *C. diff* Assay and Adding *C. difficile* Toxin A Table 1 shown above displays the microplate assay performance. Table 2 displays the cartridge/analyzer performance.

TABLE 2

*C. difficile* toxin B test compared to cytotoxicity assay (Cartridge/analyzer)

|  |  | Cytotoxicity Assay | |
|---|---|---|---|
|  |  | Positive | Negative |
| Multipath Assay | Positive | 82 | 17 |
|  | Negative | 11 | 442 |
|  |  | Sensitivity | 88% |
|  |  | Specificity | 96% |
|  |  | Accuracy | 95% |

Figure 14:
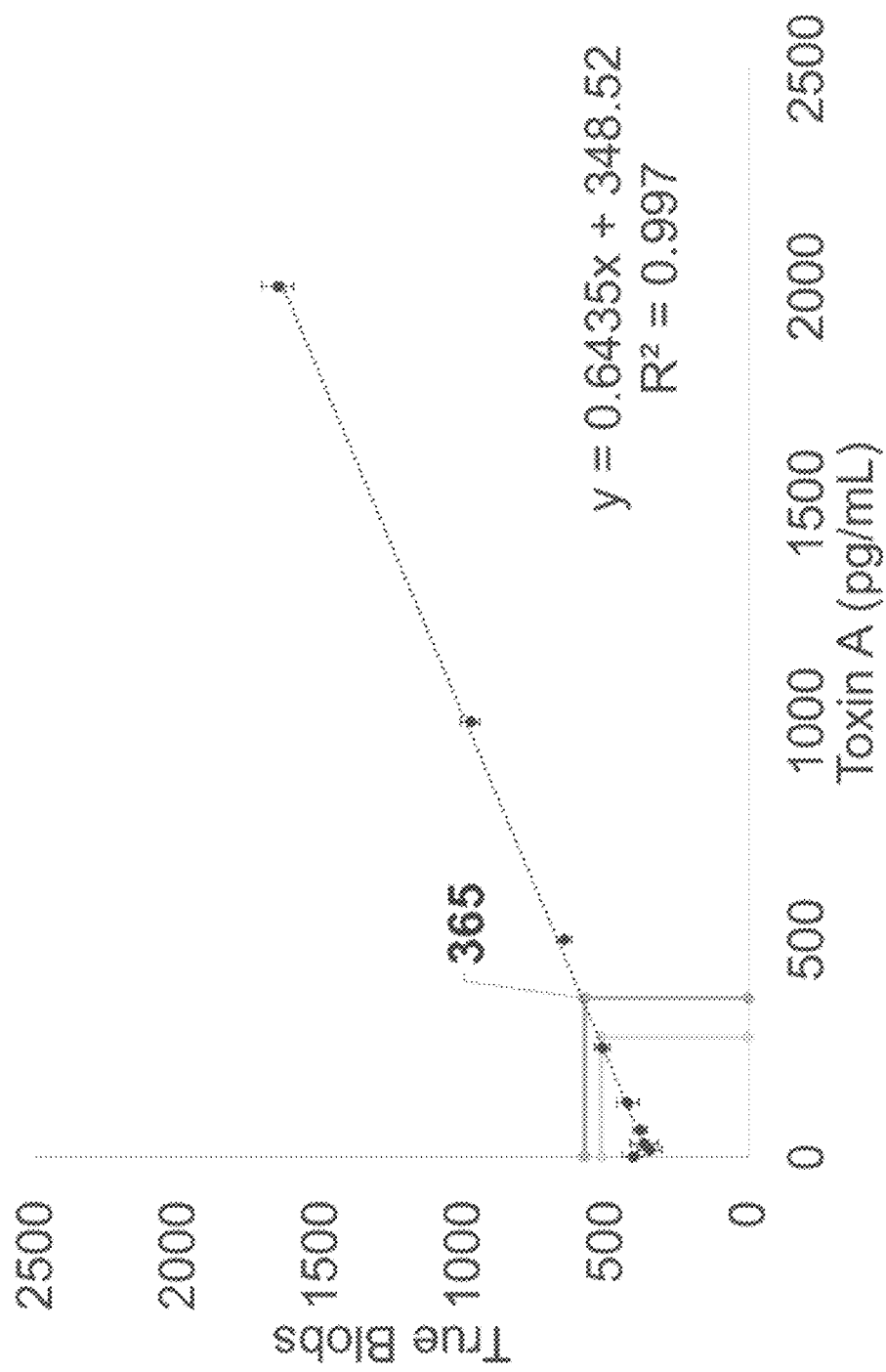
FIG. 14 shows the toxin A performance (LoD).
Figure 15:
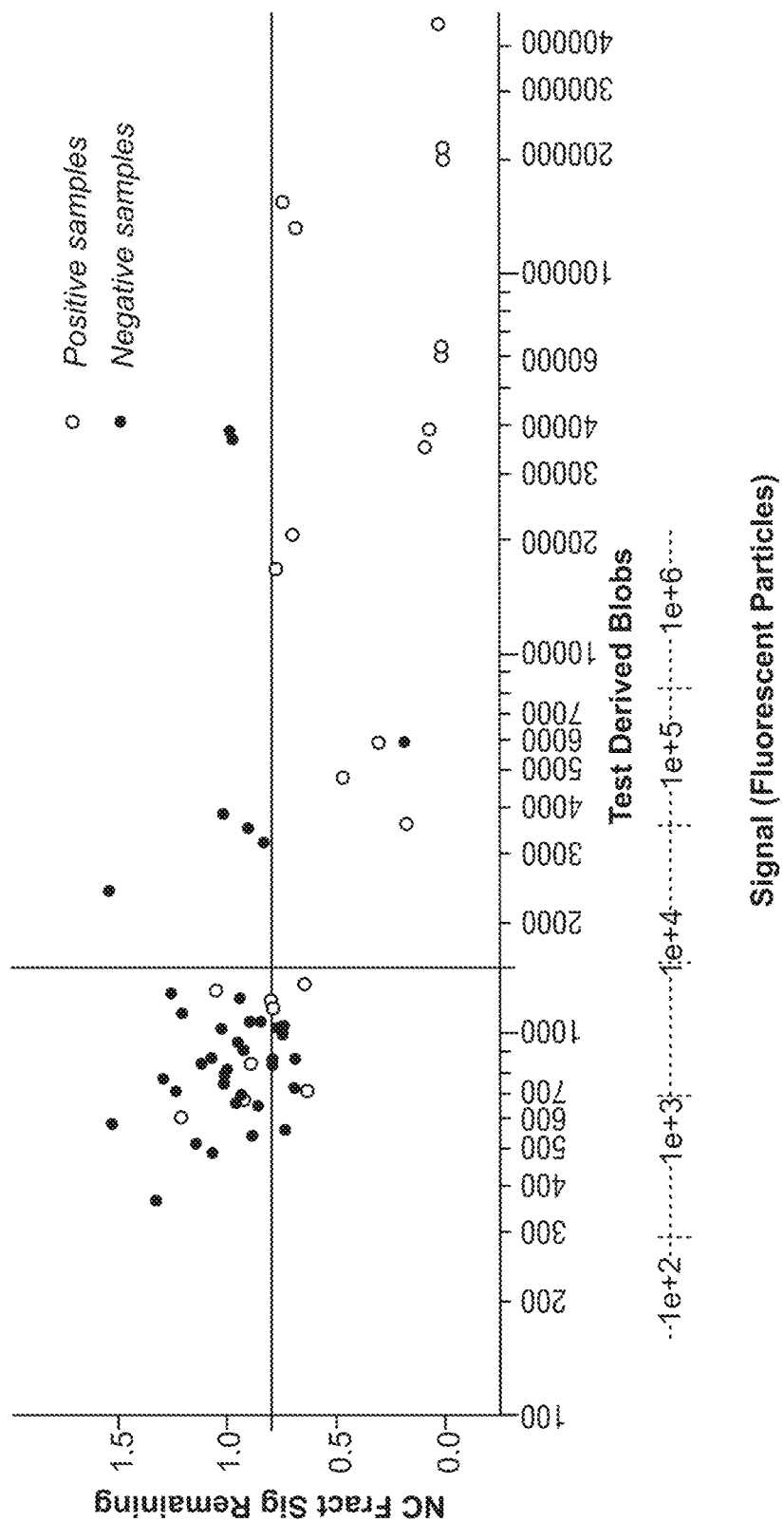
FIG. 15 shows toxin A clinical sample testing for an antibody pair of magnetic particle and fluorescent particle.
Figure 16:
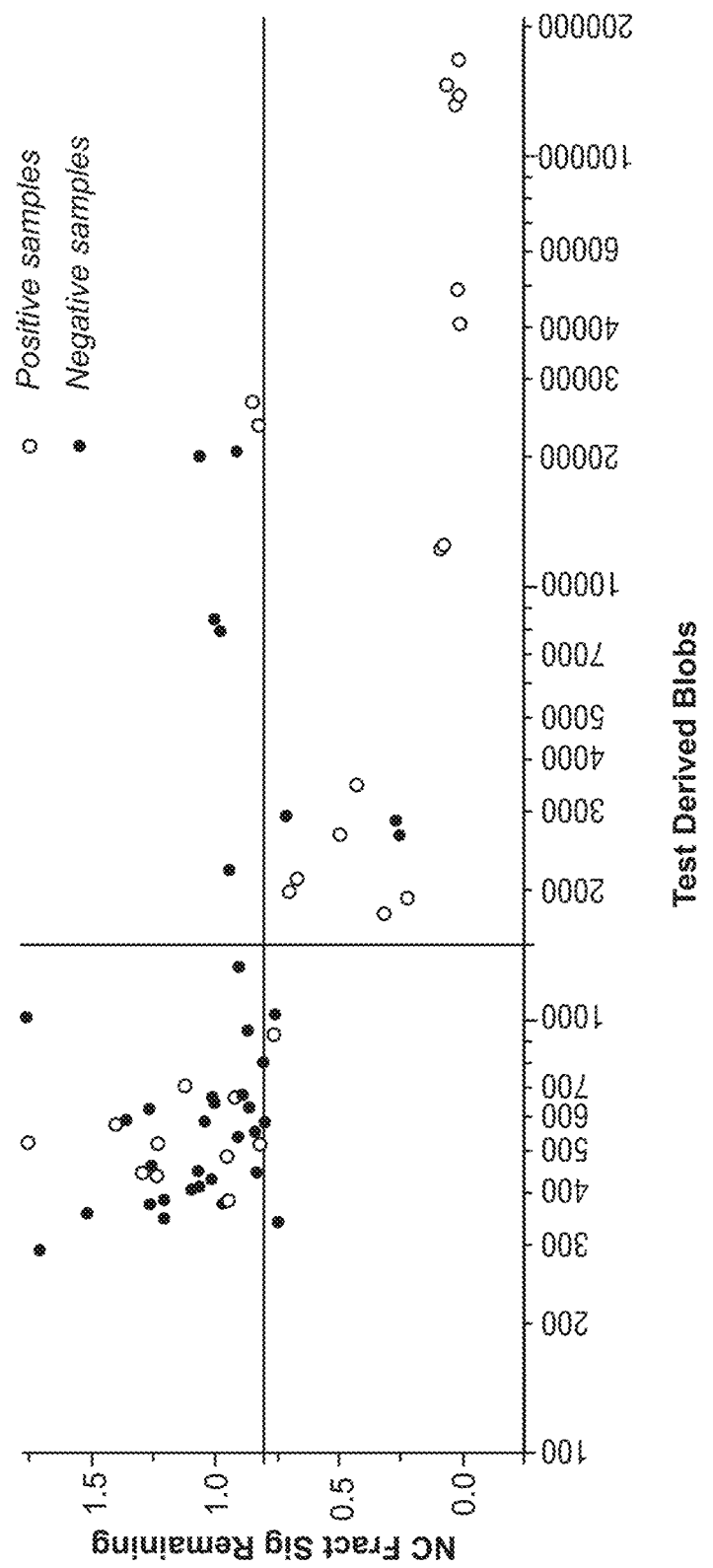
FIG. 16 shows toxin A clinical sample testing for an antibody pair of magnetic particle and fluorescent particle.
Figure 17:
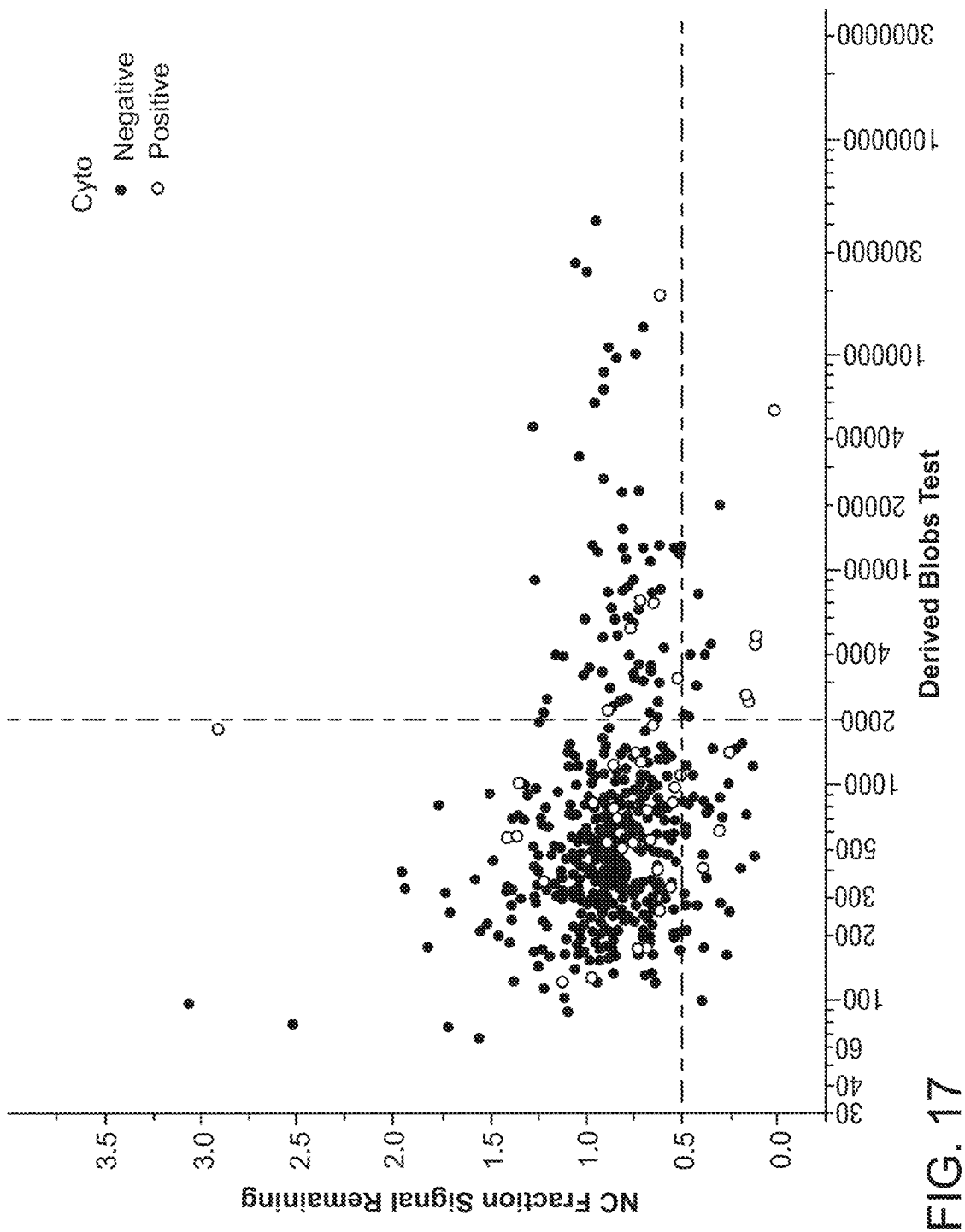
FIG. 17 shows a plot of data using plates for fresh clinical samples using toxin A.
Figure 18:
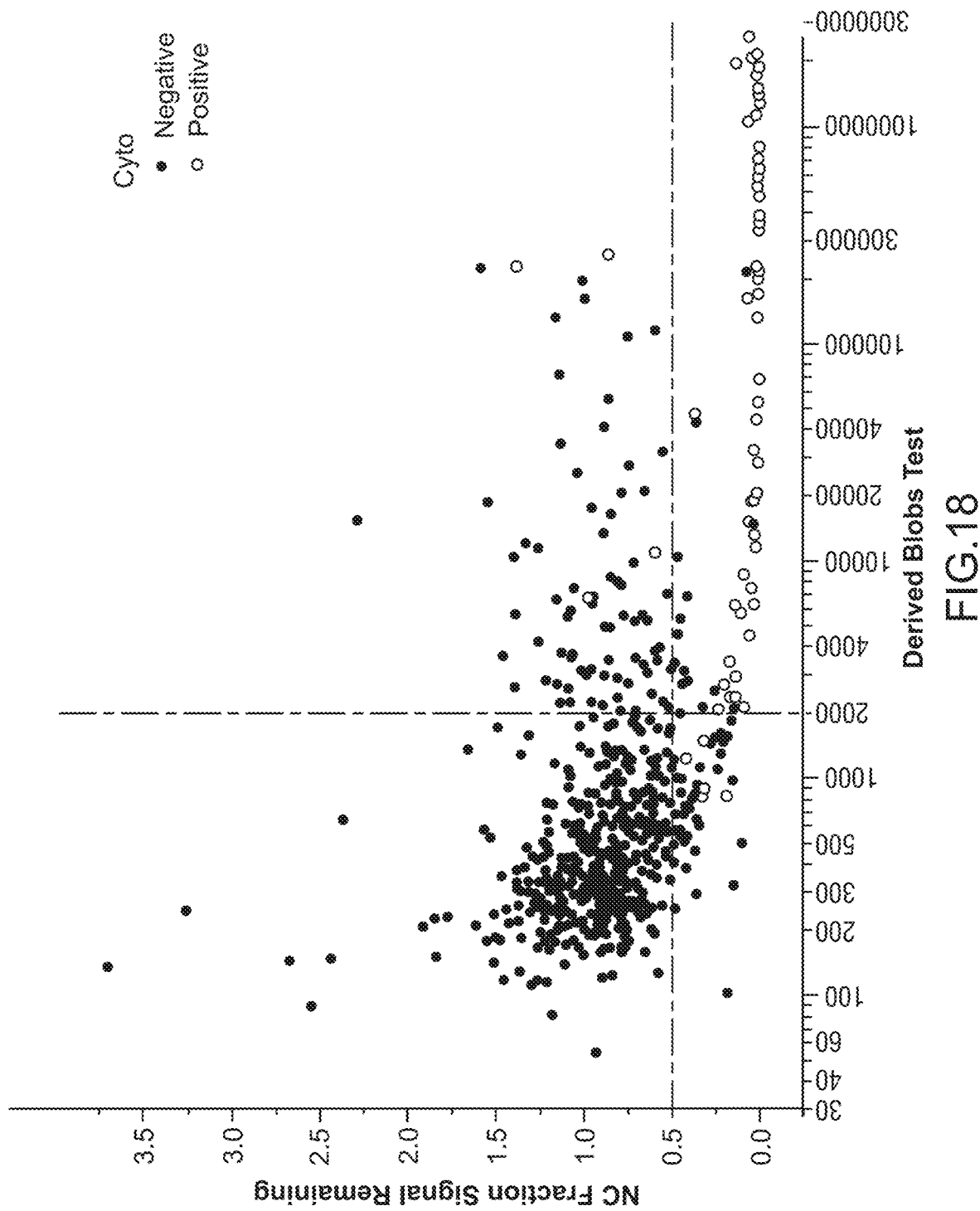
FIG. 18 shows a plot of data using plates for fresh clinical samples using toxin B.

A total of 144 toxin A antibody pairs were screened in order to select the toxin A antibody pair FIG. 14 shows the Toxin A LoD (antibody pair J/L) (½ LoD). Toxin A clinical sample testing for antibody pairs was carried out for magnetic particle G with fluorescent particle L (FIG. 15), as well as for magnetic particle J with fluorescent particle L (FIG. 16). Antibodies for toxin A were selected based on testing for the LoD and performance on clinical samples. LoD for both toxin A and B meet product requirements. LoD for toxin B is 45 pg/mL. LoD for toxin A is 365 pg/mL. Moreover, testing with fresh clinical samples using toxin A (FIG. 17) and toxin B (FIG. 18) shows excellent performance.

Table 3 displays the cartridge/analyzer performance.

TABLE 3

*C. difficile* toxin A + B test compared to cytotoxicity assay (Cartridge/analyzer)

|  |  | Cytotoxicity Assay | |
|---|---|---|---|
|  |  | Positive | Negative |
| Multipath Assay | Positive | 90 | 20 |
|  | Negative | 4 | 721 |
|  |  | Sensitivity | 96% |

TABLE 3-continued

C. difficile toxin A + B test compared to cytotoxicity assay (Cartridge/analyzer)

| | Cytotoxicity Assay | |
|---|---|---|
| | Positive | Negative |
| Specificity | | 97% |
| Accuracy | | 97% |

Example 6: A Rapid Single Molecule Counting Method Sensitively Detects *Clostridium difficile* Toxin B Directly in Stool Samples Background. An ultrasensitive MultiPath *Clostridium difficile* toxin B test based on a novel digital imaging technology was developed that counts single target molecules in stool samples with little or no sample preparation. Current tests for *C. difficile* gastrointestinal infection can be inaccurate. *C. difficile* toxin immunoassays often lack clinical sensitivity. Nucleic acid amplification tests have excellent clinical sensitivity but can have diminished clinical specificity due to their inability to distinguish patients with *C. difficile* infection from patients that are carriers of *C. difficile* organisms. Because production of toxin is a hallmark of *C. difficile* infection, an ultrasensitive *C. difficile* toxin test, such as the one presented in this report, could address the issues associated with the current tests and offer improved accuracy for detecting patients with this devastating infection.

Technical Approach. The MultiPath *C. difficile* toxin B test uses non-magnified digital imaging to count target-specific magnetic and fluorescent particles that have been tethered together by toxin molecules. The method includes the use of a novel dye-cushion that eliminates the need for sample preparation and wash steps. Clinical stool samples were tested to estimate the limit of detection, imprecision, and dynamic range. The potential for achieving good clinical accuracy was assessed by comparing the results of the new toxin test to those of the sensitive cell cytotoxicity reference method for toxin detection.

Figure 19:
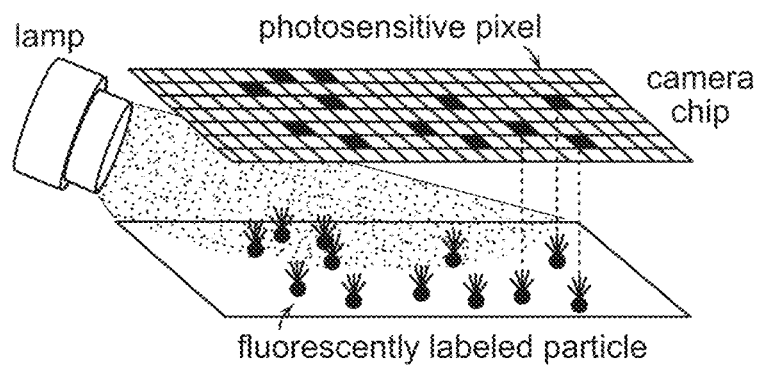
FIGS. 19-21 show the technology used for detection of *Clostridium difficile* Toxin B.
Figure 20:
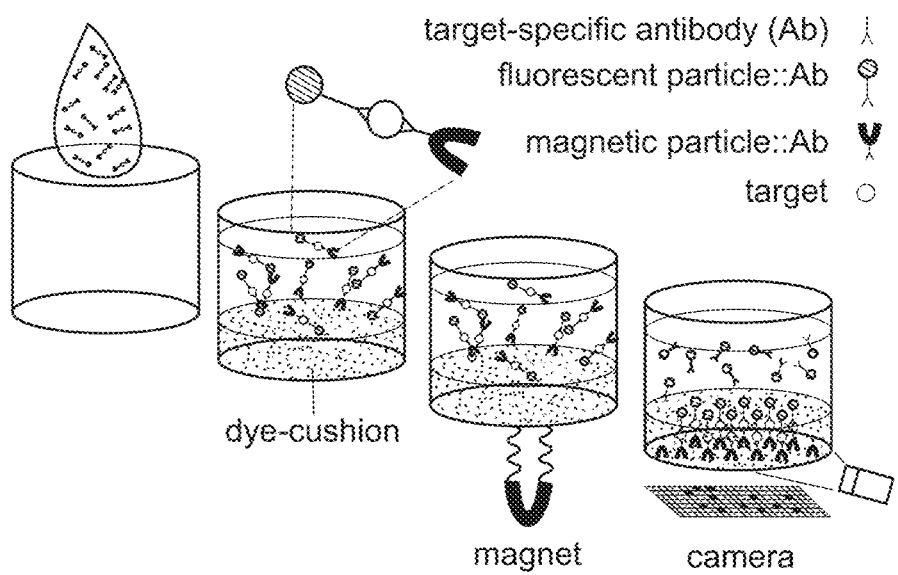
Figure 21:
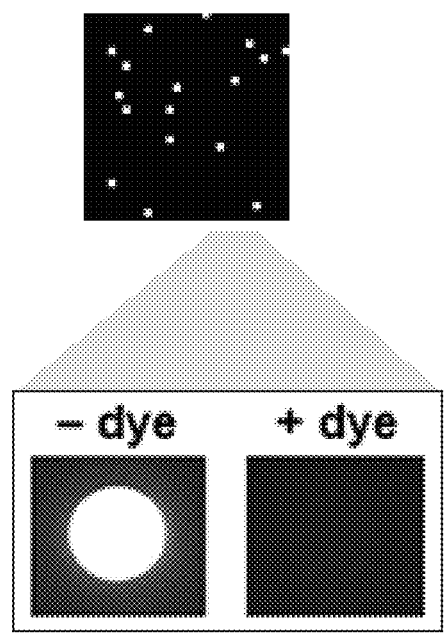

Technology. Technology used includes a dye-cushion, which eliminates sample prep and washes. The technology has a 30 minute test turnaround. Technology used includes positive and neutralization internal controls. All steps are carried out in a cartridge on an automated analyzer. All reagents are stabilized in the cartridge. Technology used is shown in FIGS. 19-21.

Platform Workflow. A sample cartridge, labeled reference numeral 1, and a sample analyzer, labeled reference numeral 2, are shown in FIG. 22.

Figure 23:
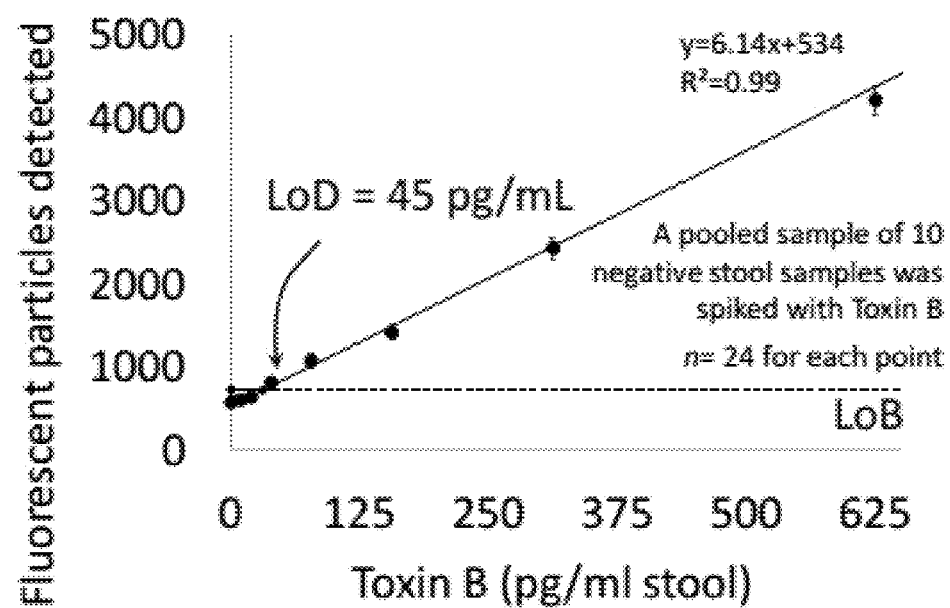
FIGS. 23-25 show the analytical results for detection of *Clostridium difficile* Toxin B.
Figure 24:
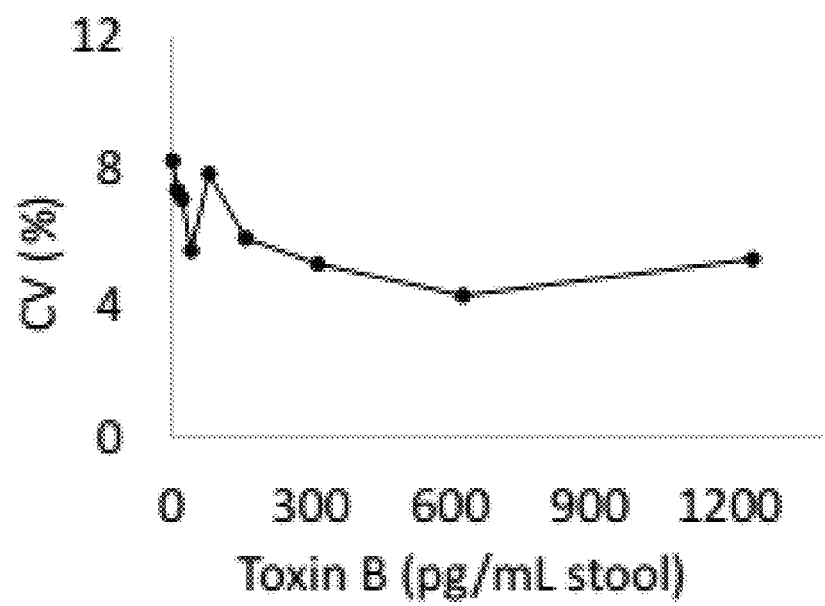
Figure 25:
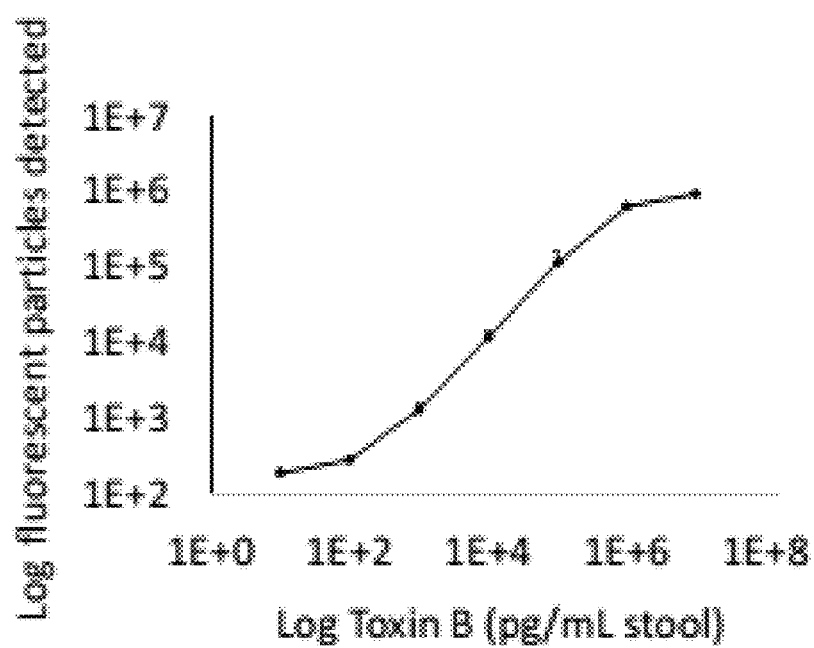

Analytical Results. Analytical results are shown in FIGS. 23-25.

Interference. 20 potentially interfering substances commonly associated with diarrheal stool samples were found to have no impact on the assay results for samples spiked with toxin B.

Inclusivity. Analysis of toxins from strains representing common ribotypes (027, 106, 014, 002, 017, 001, 078, 036, 087) showed similar dose/responses when spiked into a pooled stool sample.

Exclusivity/Cross-Reactivity. The toxin assay performance in stool samples was evaluated in the presence of 23 commonly encountered off-target species≥1e8 CFU/mL. None of them inhibited detection of toxin B spiked or caused false positive results.

Clinical Feasibility Results.

Semi-Manual Analysis. A training set of 320 clinical unformed stool samples from patients suspected of having *C. difficile* infection was used to select parameters to yield optimum accuracy relative to the cellular cytotoxicity neutralization assay (CCNA) reference test. The assays were conducted using microtiter plates and manual pipetting steps. The results of a commercial enzyme immunoassay and a PCR test were compared to the CCNA results.

TABLE 4

Multipath 30 minutes test compared to CCNA

| | | Reference (CCNA) | |
|---|---|---|---|
| | | Positive | Negative |
| Multipath 30 minutes | Positive | 96 | 9 |
| | Negative | 3 | 528 |
| | | Sensitivity | 97.0% |
| | | Specificity | 98.3% |

TABLE 5

Nucleic acid amplification test compared to CCNA

| | | Reference (CCNA) | |
|---|---|---|---|
| | | Positive | Negative |
| Nucleic Acid | Positive | 97 | 77 |
| Amplification | Negative | 2 | 460 |
| | | Sensitivity | 98.0% |
| | | Specificity | 85.7% |

TABLE 6

Enzyme immunoassay test compared to CCNA

| | | Reference (CCNA) | |
|---|---|---|---|
| | | Positive | Negative |
| Enzyme Immunoassay | Positive | 21 | 5 |
| | Negative | 6 | 84 |
| | | Sensitivity | 77.8% |
| | | Specificity | 94.4% |

Fully Automated Analysis. A random subset of samples was tested on an automated MultiPath Analyzer prototype and MultiPath consumable cartridge and compared the results to the CCNA results.

TABLE 7

Multipath Analyzer test compared to CCNA

| | | CCNA | |
|---|---|---|---|
| | | Positive | Negative |
| Multipath Automated | Positive | 54 | 10 |
| Analyzer & Cartridge | Negative | 3 | 304 |
| | | Sensitivity | 95% |
| | | Specificity | 97% |

Limitations. The test detects only *C. difficile* toxin B but not toxin A or binary toxin. The study was not blinded and it treated the samples as a training set to optimize parameters. We only tested unformed stool samples, they had no associated patient information for sub-analyses, and they were not fresh but rather had been frozen at −80° C.

Conclusion. The data presented demonstrate the potential of the ultrasensitive MultiPath technology to deliver rapid, accurate, easy-to-use test for *C. difficile* toxin B. The technology should also have value for a variety of other important infectious disease applications.

Example 7: Rapid and Sensitive Detection of *Bacillus anthracis* Toxin Lethal Factor Direct from Blood Sample Abstract. Secreted Lethal Factor (LF), a subunit of Lethal Toxin, is the earliest known biomarker of *Bacillus anthracis* infection, making it a logical target for diagnostics to detect exposure to this potentially lethal pathogen. There are currently no commercial methods for anthrax LF detection that are rapid (time to result of fewer than 30 minutes), simple enough to use in a physician's office laboratory, and sensitive enough to detect low concentrations of LF (<100 pg/mL) early in infection. The MultiPath Anthrax test can be performed on a small volume (<60 mL) of venous or finger stick whole blood added to the disposable cartridge with no sample preparation. Once loaded into the analyzer, the test proceeds automatically without further user input. The time from sample loading to diagnostic result is fewer than 20 minutes and as many as 20 samples can be processed simultaneously on the platform. The limit of detection (LoD) of the assay, determined using whole blood samples spiked with pure LF protein, is <60 pg/mL. The dynamic range of the assay covers 5 logs of LF concentration, an important performance metric given the broad range of LF concentrations observed over the course of anthrax infections. With its ease of use, rapid time to result and high sensitivity the MultiPath Anthrax Test potentially fills an important gap in the toolkit for anthrax diagnostics.

Figure 26:
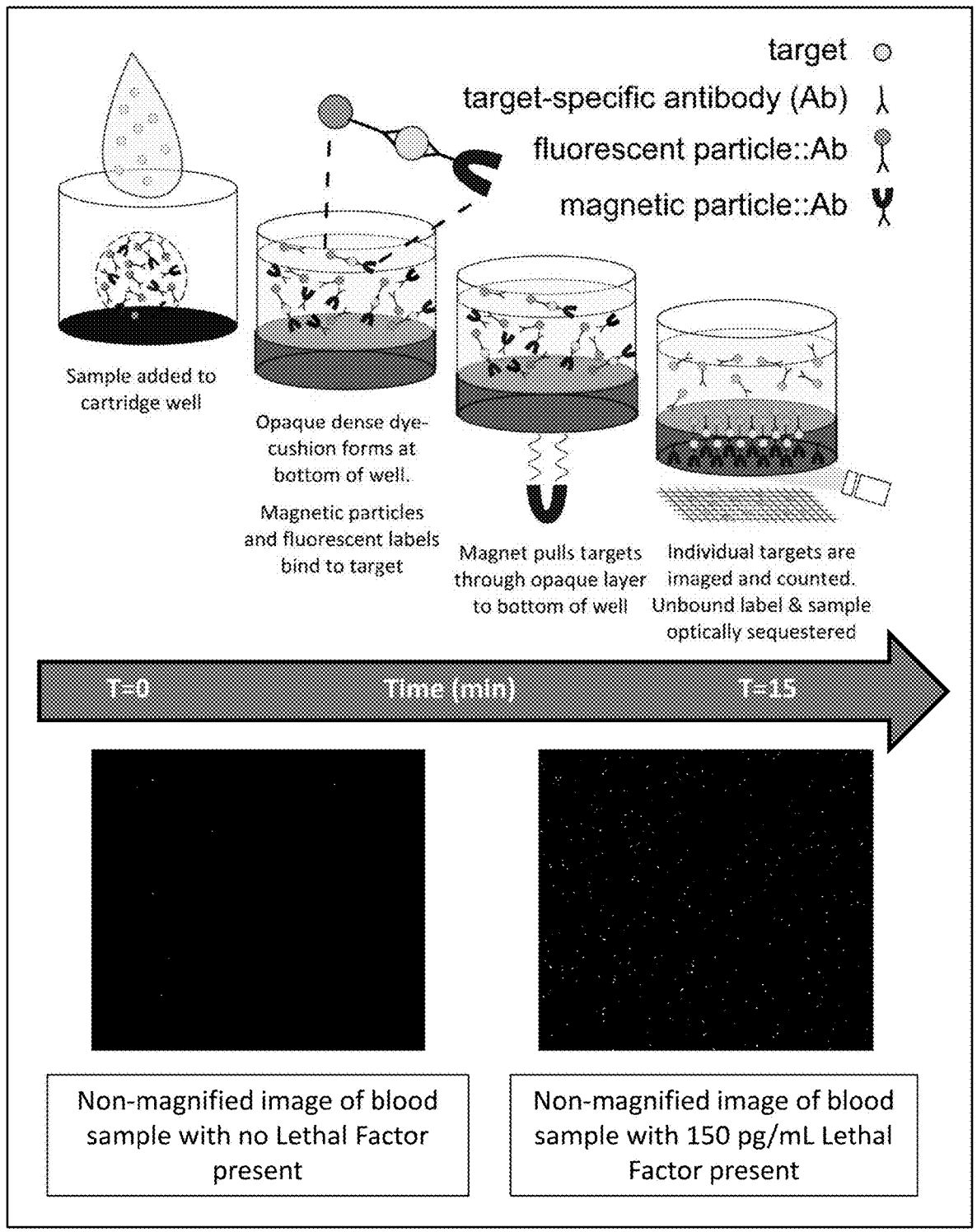
FIG. 26 shows the assay overview for detection of *Bacillus anthracis* Toxin Lethal Factor.

Overview of Assay. The assay overview is shown in FIG. 26.

Figure 27:
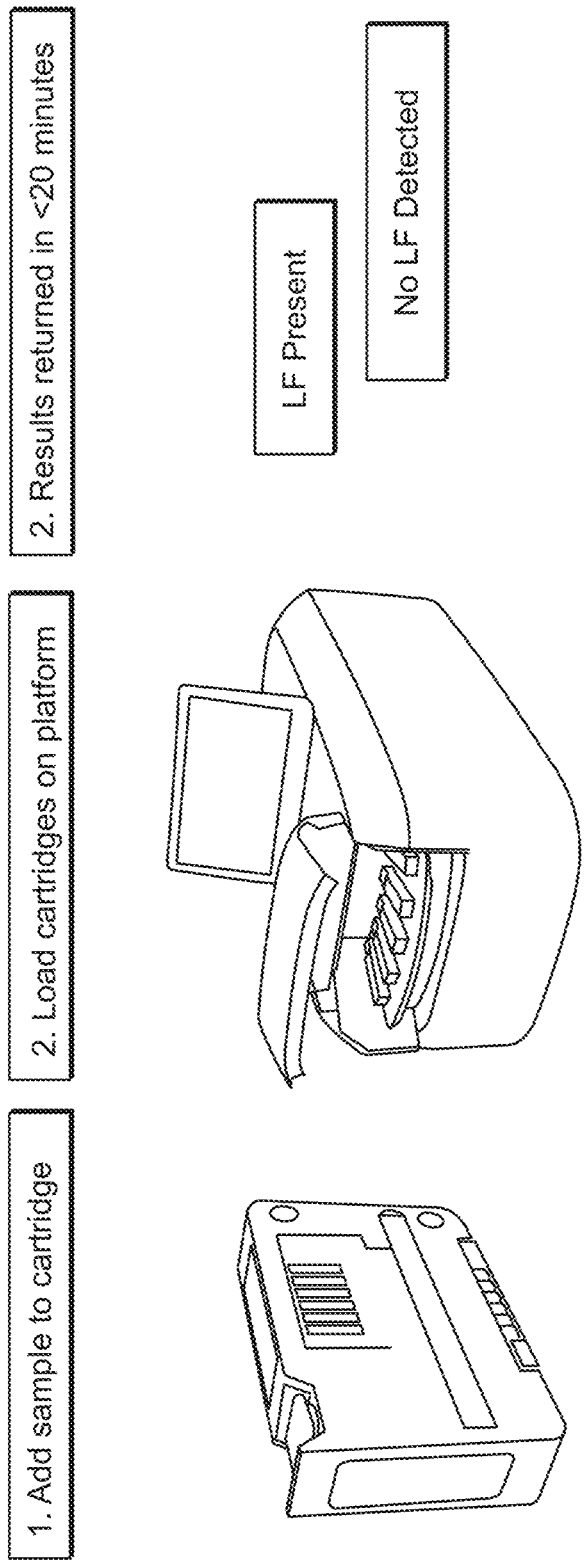
FIG. 27 shows the workflow for detection of *Bacillus anthracis* Toxin Lethal Factor.

Workflow. The MultiPath platform currently being developed requires no sample preparation. Venous whole blood or finger-stick blood is added to a sample diluent stored in the cartridge. Cartridges are loaded onto the MultiPath Analyzer. The analyzer provides a diagnostic readout in <20 minutes. The workflow is shown in FIG. 27.

Figure 28:
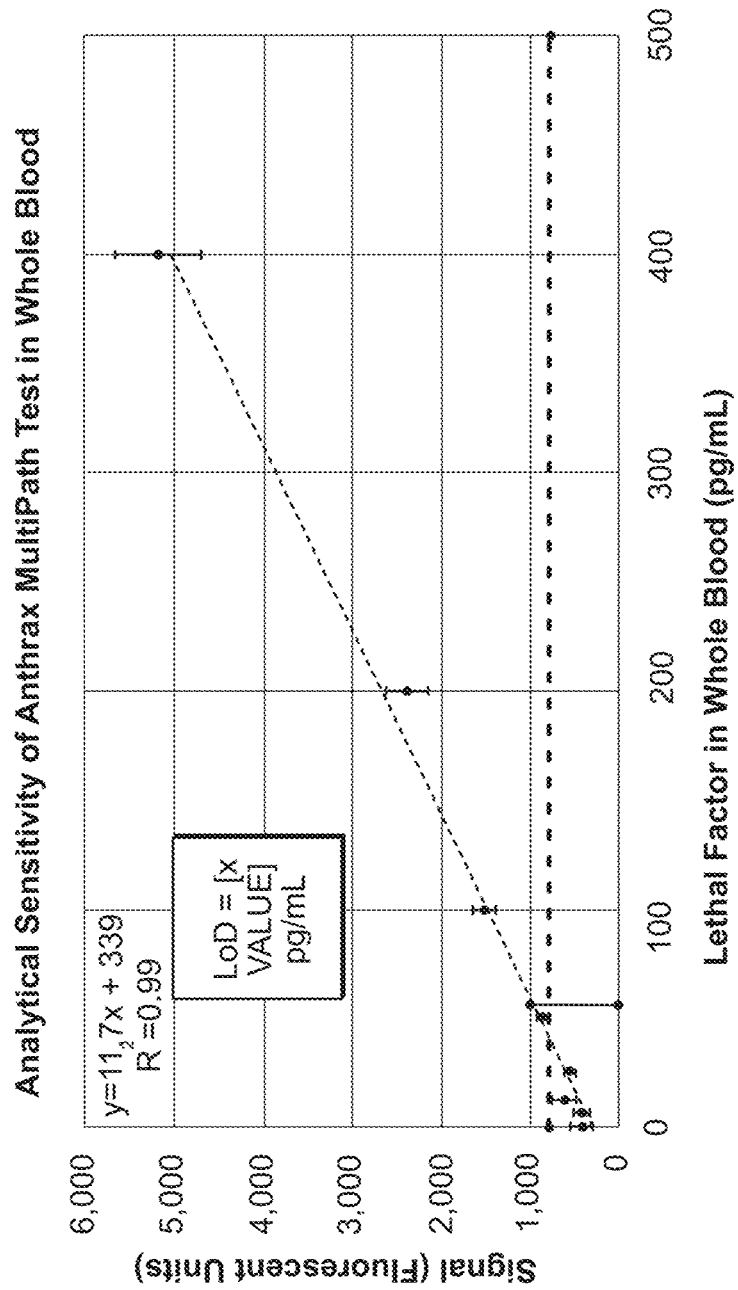
FIG. 28 shows the results for detection of *Bacillus anthracis* Toxin Lethal Factor.

Analytical Sensitivity. Lethal Factor was serially diluted into venous whole blood samples, then run through the MultiPath platform. Limit of the Blank was determined as 3 standard deviations above the mean of 24 independently prepared blank samples. The analytical sensitivity was determined by determining the lowest interpolated concentration of Lethal Factor at which 95% of data points are expected to reside above the limit of the blank. Comparable performance is seen across a panel of blood samples. Results are shown in FIG. 28.

Figure 29:
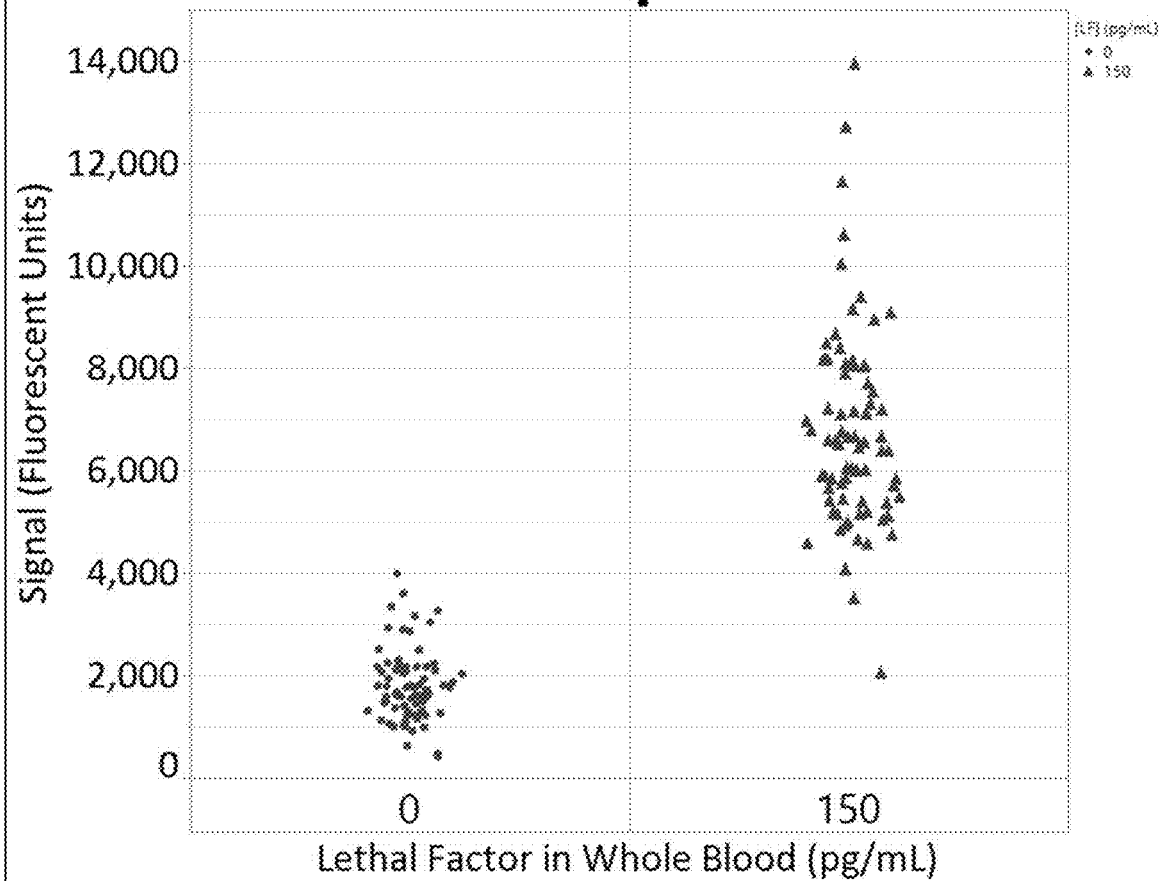
FIG. 29 shows the distribution of signal of the population of un-spiked and spiked samples for detection of *Bacillus anthracis* Toxin Lethal Factor.

Detection of Lethal Factor Spiked into Whole Blood Samples. 48 negative individual patient samples of whole venous blood were run on the MultiPath platform in duplicate. Lethal Factor was then spiked into the same 48 samples at 150 pg/mL and run in duplicate on the MultiPath platform. The distribution of signal of the population of un-spiked and spiked samples is shown in FIG. 29 and Tables 8 and 9 below, as is the presumptive diagnostic performance using a signal cutoff of 4000 fluorescent units.

TABLE 8

| Comparison of Spiked and Unspiked | | |
| --- | --- | --- |
| | MultiPath Positive | MultiPath Negative |
| Spiked | 94 | 2 |
| Unspiked | 1 | 95 |

TABLE 9

| Diagnostic Performance Diagnostic Performance | |
| --- | --- |
| Positive % Agreement | 98% |
| Negative % Agreement | 99% |
| Accuracy | 99% |

Robustness to Microbial Interference. The ability of the MultiPath system to correctly identify the presence or absence of Lethal Factor was tested in the presence of various common microbial organisms, which were spiked into whole blood at 1E7 cfu/mL, as per CLSI guidelines. The MultiPath system was able to correctly detect the presence or absence of Lethal Factor in all cases.

TABLE 10

| Presence of Lethal Factor for Potential Microbial Interferents | | |
| --- | --- | --- |
| Potential Microbial Interferent (at 1E7 cfu/mL) | 0 pg/mL | 150 pg/mL |
| *Enterobacter cloacae* | No LF Detected | LF Present |
| *Staphylococcus epidermis* | No LF Detected | LF Present |
| *Bacillus licheniformis* | No LF Detected | LF Present |
| *Klebsiella oxytoca* | No LF Detected | LF Present |
| *Candida albicans* | No LF Detected | LF Present |
| *Staphylococcus aureus* | No LF Detected | LF Present |
| *Escherichia coli* | No LF Detected | LF Present |
| *Pseudomonas pneumonia* | No LF Detected | LF Present |
| *Klebsiella pneumonia* | No LF Detected | LF Present |
| *Enterococcus faecalis* | No LF Detected | LF Present |

Robustness to Chemical Interference. The ability of the MultiPath platform to correctly identify the presence or absence of Lethal Factor was tested in the presence of various potential interfering substances. Common potentially interfering endogenous and exogenous substances were tested at recommended concentrations as per CLSI guidelines. The MultiPath platform was able to correctly detect the presence or absence of Lethal Factor in all cases.

TABLE 11

| Presence of Lethal Factor for Potential Chemical Interferents | | | |
| --- | --- | --- | --- |
| Potential Interferent | 0 pg/mL | 150 pg/mL | 300 pg/mL |
| Acetaminophen (0.2 mg/mL) | No LF Present | LF Detected | LF Detected |
| Amoxicillin (0.08 mg/mL) | No LF Present | LF Detected | LF Detected |

TABLE 11-continued

Presence of Lethal Factor for Potential Chemical Interferents

| Potential Interferent | 0 pg/mL | 150 pg/mL | 300 pg/mL |
|---|---|---|---|
| Ascorbic Acid (0.06 mg/mL) | No LF Present | LF Detected | LF Detected |
| Albuterol (0.4 ug/mL) | No LF Present | LF Detected | LF Detected |
| Cefotaxime 0.31 mg/mL) | No LF Present | LF Detected | LF Detected |
| Ciprofloxacin HCl (0.01 mg/mL) | No LF Present | LF Detected | LF Detected |
| Doxycycline (0.03 mg/mL) | No LF Present | LF Detected | LF Detected |
| EDTA (1 ug/mL) | No LF Present | LF Detected | LF Detected |
| Glucose (1.2 mg/mL) | No LF Present | LF Detected | LF Detected |
| Erythromycin (0.06 mg/mL) | No LF Present | LF Detected | LF Detected |
| Ethanol (3.5%) | No LF Present | LF Detected | LF Detected |
| N acetylcysteine (1.66 mg/mL) | No LF Present | LF Detected | LF Detected |
| Gentamicin (0.01 mg/mL) | No LF Present | LF Detected | LF Detected |
| Heparin (0.02 mg/mL) | No LF Present | LF Detected | LF Detected |
| Ibuprofen (0.5 mg/mL) | No LF Present | LF Detected | LF Detected |
| Naproxen (0.5 mg/mL) | No LF Present | LF Detected | LF Detected |
| Rifampicin (0.06 mg/mL) | No LF Present | LF Detected | LF Detected |
| Sulfamethoxazole (0.28 mg/mL) | No LF Present | LF Detected | LF Detected |
| Tetracycline (0.02 mg/mL) | No LF Present | LF Detected | LF Detected |
| Isopropanol (0.32%) | No LF Present | LF Detected | LF Detected |
| Trimethoprim (0.04 mg/mL) | No LF Present | LF Detected | LF Detected |
| Acetone (0.03%) | No LF Present | LF Detected | LF Detected |
| Chloroquine (0.05 mg/mL) | No LF Present | LF Detected | LF Detected |
| Albumin (50 mg/mL) | No LF Present | LF Detected | LF Detected |
| Streptomycin (0.35 mg/mL) | No LF Present | LF Detected | LF Detected |
| Sodium citrate (38 mg/mL) | No LF Present | LF Detected | LF Detected |
| SPS (0.5 mg/mL) | No LF Present | LF Detected | LF Detected |
| Cromolyn sodium (0.04 mg/mL) | No LF Present | LF Detected | LF Detected |
| Flunisolide (0.84 ug/mL) | No LF Present | LF Detected | LF Detected |
| Tobramycin (0.02 mg/mL) | No LF Present | LF Detected | LF Detected |
| Triglycerides (5 mg/mL) | No LF Present | LF Detected | LF Detected |
| Human IgG (36 mg/mL) | No LF Present | LF Detected | LF Detected |
| DMSO (1.1%) | No LF Present | LF Detected | LF Detected |
| NH4OH (0.45%) | No LF Present | LF Detected | LF Detected |
| Bleach (1%) | No LF Present | LF Detected | LF Detected |
| Bilirubin (0.15 mg/mL) | No LF Present | LF Detected | LF Detected |
| Cholesterol (2.5 mg/mL) | No LF Present | LF Detected | LF Detected |
| Hemoglobin (2 mg/mL) | No LF Present | LF Detected | LF Detected |
| Acid-citrate-dextrose (10%) | No LF Present | LF Detected | LF Detected |
| Acid-citrate-dextrose (1%) | No LF Present | LF Detected | LF Detected |

Figure 30:
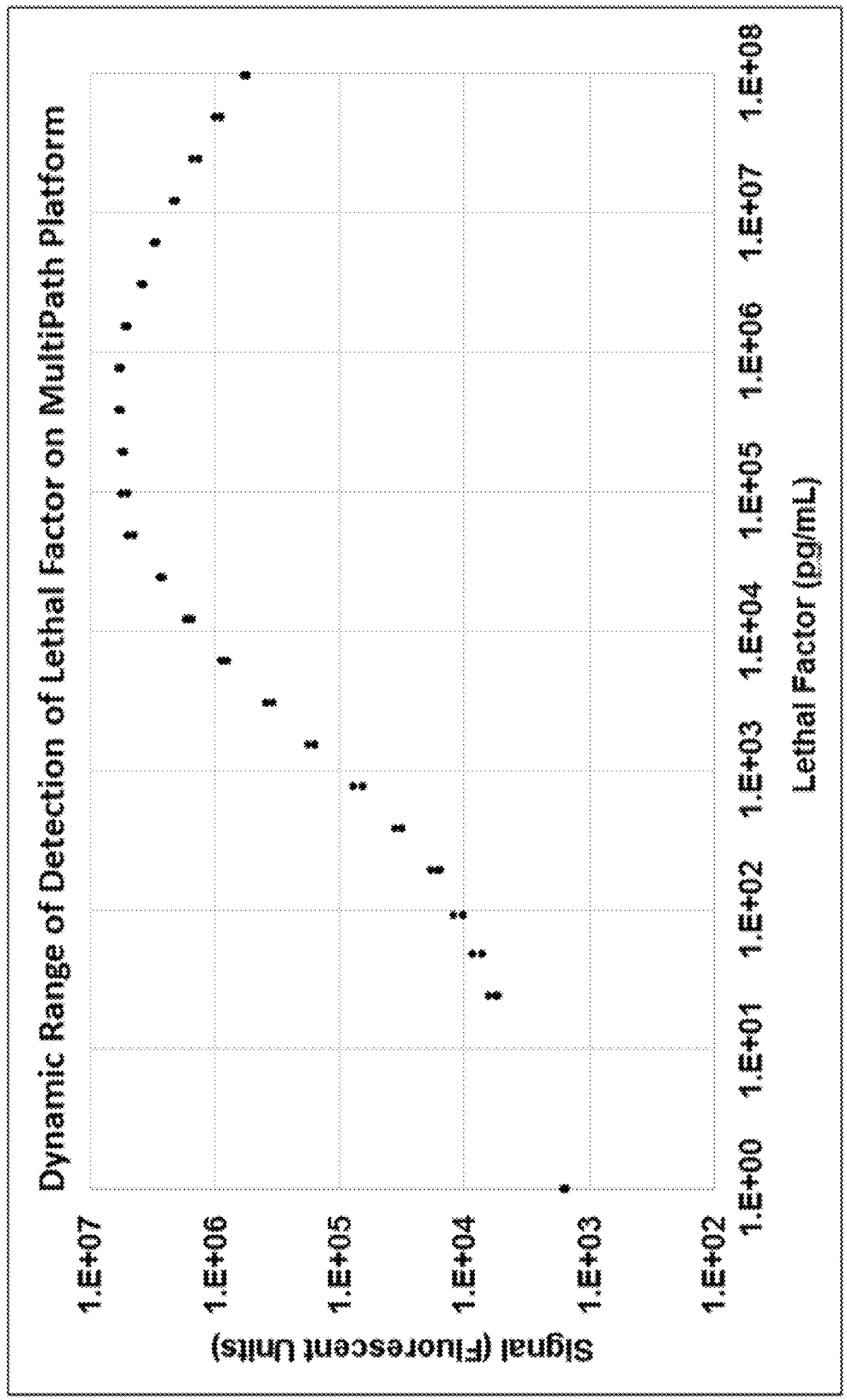
FIG. 30 shows the results dynamic range results for detection of *Bacillus anthracis* Toxin Lethal Factor.

Dynamic Range. The MultiPath platform has a dynamic range of over 1E5 pg/mL of Lethal Factor. Lethal Factor was serially diluted from 1 µg/mL to 100 pg/mL and spiked into pooled human plasma. The samples were then run in triplicate for each spike level on the MultiPath platform. Results are shown in FIG. 30.

Summary. The MultiPath Anthrax test run on the MultiPath platform requires minimal sample preparation, returns a result in <20 minutes, and can detect Lethal Factor over a large dynamic range down to <60 pg/mL in whole blood while demonstrating robustness to commonly interfering substances and organisms, offering health care providers a rapid testing solution at the point of medical need in the event of public exposure to *Bacillus anthracis*.

Example 8: Rapid and Sensitive Anthrax and AST Tests on an Automated Platform

Testing using the methods herein saves lives, lowers costs, and decreases resistance. Patients get targeted narrow spectrum therapy at the onset of infection. The methods lower morbidity, mortality, and length of hospital stay, and decrease the spread of resistance.

Technology used addresses a uniquely broad range of key market applications. Proof-of-concept data was obtained from clinical samples, and working platform prototypes were used. There is pressure to lower inappropriate use of antibiotics (POC, hospitals), and significant financial pressure on hospitals to lower infection rates.

The platform provides high-performance, rapid, affordable tests for hospitals, clinics, and physician office labs. The dual-use platform is suitable for key clinical and public health applications and provides rapid AST for all major syndromic infections and rapid ultrasensitve tests for toxins and pathogens.

Figure 31:
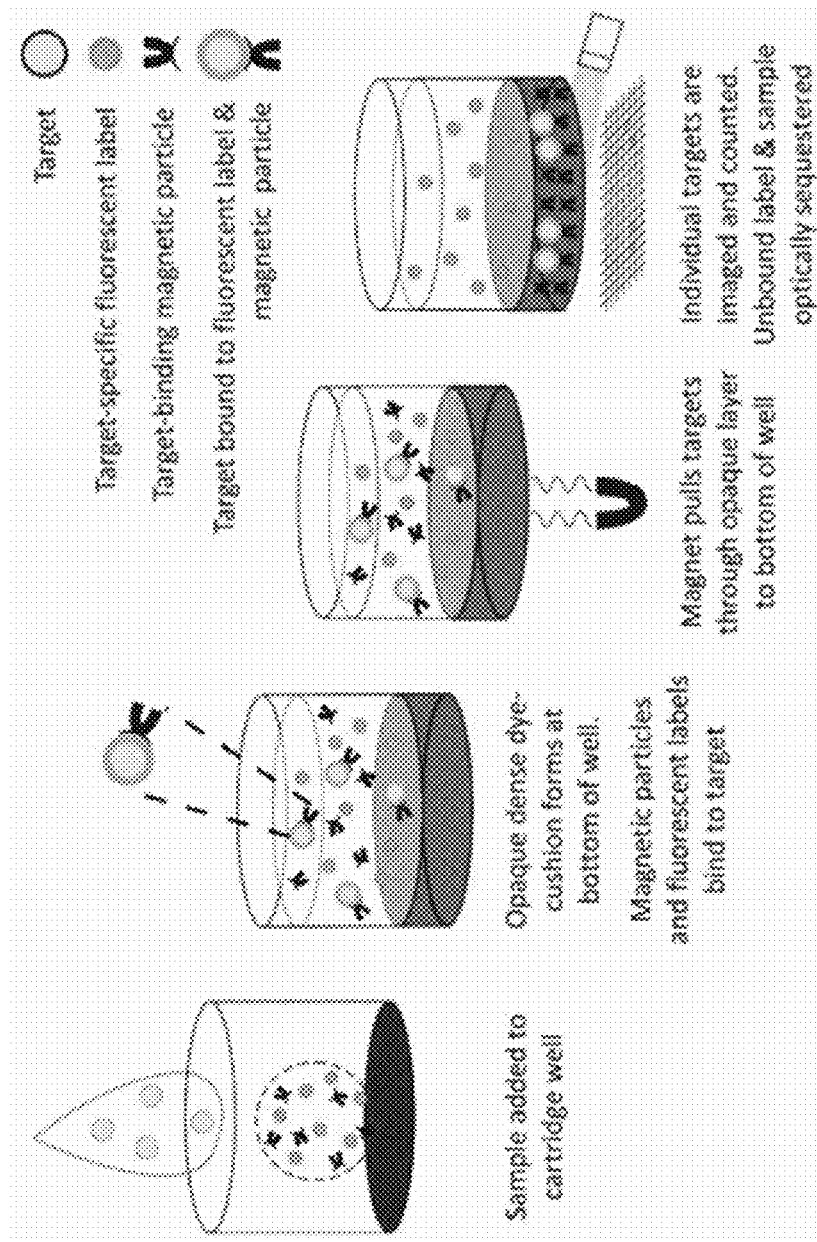
FIG. 31 shows detecting targets without sample prep or wash steps.

The technology detects infections and counts molecules, cells, viruses, and toxins in 30 minutes and phenotypic AST for pathogens in 4 hours. The technology directly uses samples (blood, nasal swab, stool, urine), with no sample prep. The technology is highly sensitive and specific and counts individual targets, such as for low pg/mL LoD for biomarkers/toxins, with bacterial detection comparable to qPCR (~10 CFU/mL). The technology determines antibiotic susceptibility in 1 to 3 doubling times. All reagents are contained in the cartridge. Tests in development address significant medical applications, such as a bio-defense tests like an Anthrax Test and commercial tests for *C. difficile*, UTI ID/AST, and CAUTI ID/AST. FIG. 31 shows detecting targets without sample prep or wash steps. The dye-cushion eliminates user sample prep and wash steps.

The Analyzer includes enclosure and thermal controls required for assay robustness, reduced test time, and bacterial growth. The cartridge rack loading interface with safety interlocks. The Analyzer includes a built in computer and integrated results analysis and database and a Graphical User Interface and touch screen. The Analyzer has an Industrial Design and a smaller footprint. An exemplary analyzer has dimensions of H 18"×W 20"×25" D. Another exemplary analyzer has dimensions of H 15"×W 15"×24" D.

Software includes analyzer user interface, software development quality process, automated image & results analysis, results database, software for expanding the test menu without software update, cartridge loading & trash monitoring software, and automated results verification tests.

Cartridges include a universal modular cartridge design for all tests in the pipeline. Cartridges increase the well number from 6 to 16, have improved fluidics (i.e., minimize bubbling), reduce part count while increasing number of wells, reduce assembly steps, and reduce pneumatic ports from 5 to 1.

Anthrax Test

The test comprises detecting anthrax following a biothreat event. The test detects lethal factor (LF) in blood samples. LF is a toxin subunit secreted by *B. anthracis*, appears early in inhalational anthrax infection, and occurs free or complexed to Protective Antigen (Lethal Toxin). The test includes a finger-stick or venous whole blood samples (70 uL). There is a positive test result if ≥150 pg/ml blood. Internal controls improve accuracy.

Figure 33:
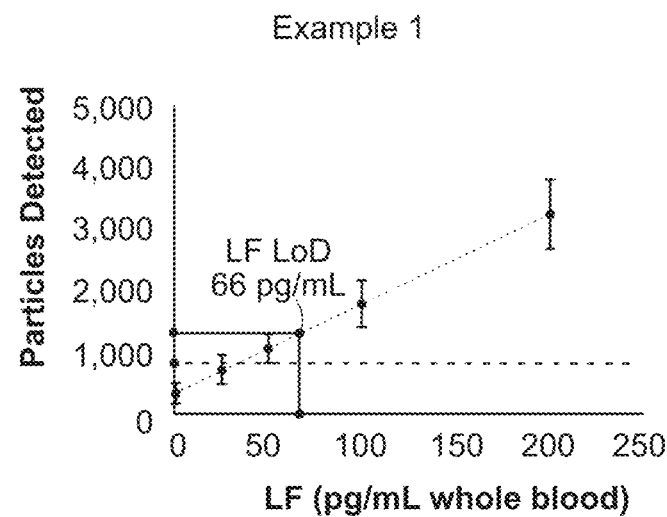
FIG. 33 shows Example 1 of the Anthrax Test.
Figure 34:
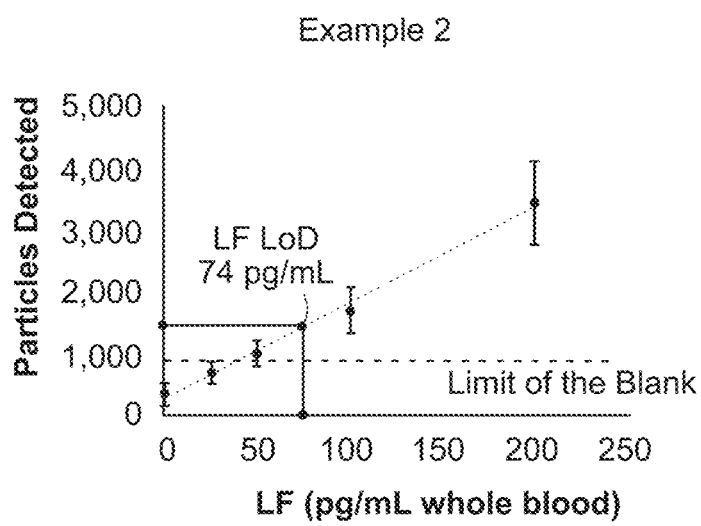
FIG. 34 shows Example 2 of the Anthrax Test.

Analytical performance is shown in FIG. 32. FIG. 33 shows Example 1 and FIG. 34 shows Example 2. Testing was side by side on 4 different days. Venous blood samples from 4 patients were tested. Replicates were $n_{BLANK}=24$, $n_{SPIKED}=12$. Testing NHP inhalation anthrax samples on Example 2 are shown in FIG. 35. Samples cover time course of infection for 2 animals. MultiPath results (pos/neg) were compared to ref. method results.

Figure 36:
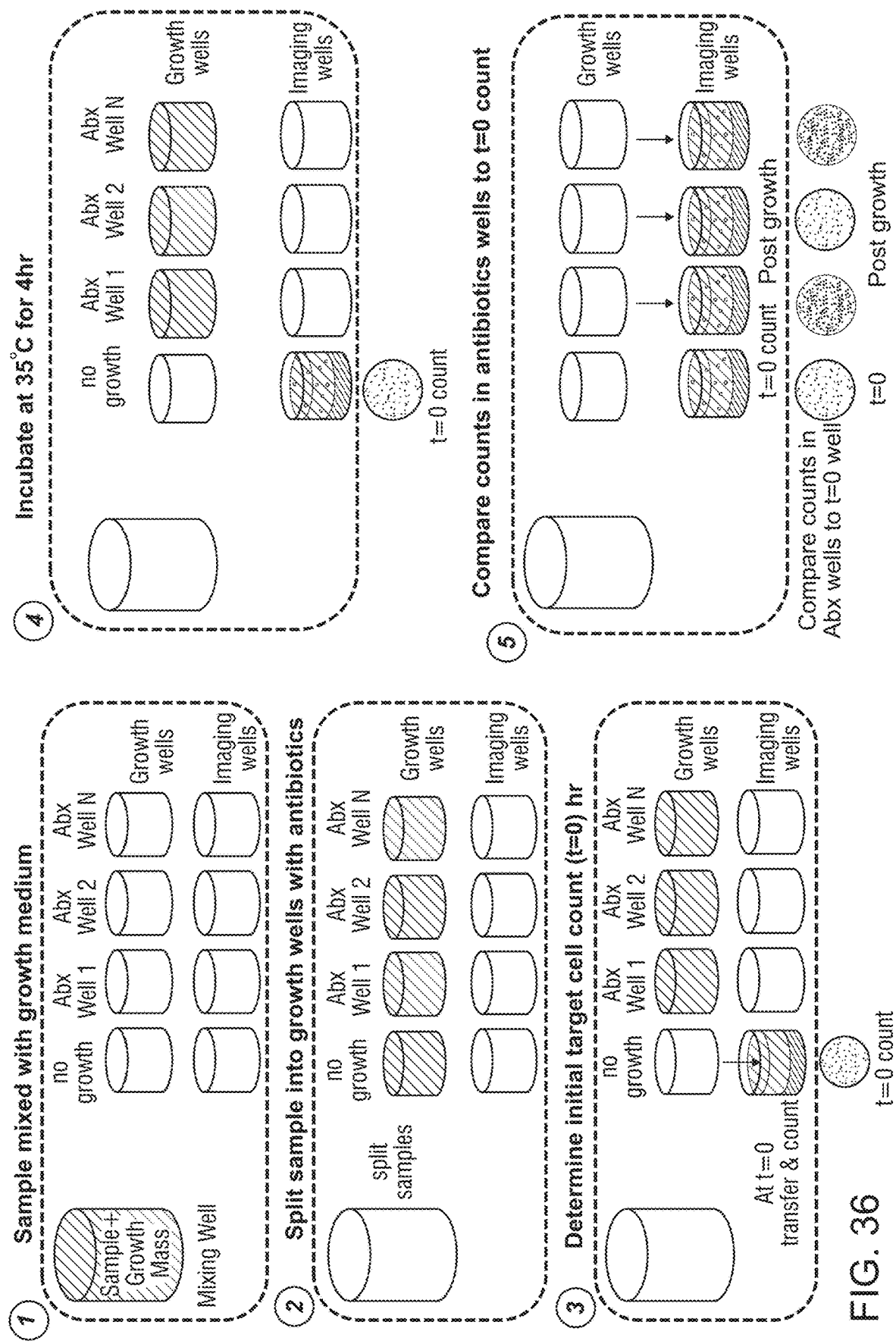
FIG. 36 shows AST workflow in cartridge.

There are values in rapid ID/AST testing. Current ID/AST testing takes days to determine optimum therapy. Unnecessary or ineffective antibiotics may be prescribed. Empiric broad spectrum antibiotic therapy increases resistance. The goal of rapid AST is to prescribe narrow-spectrum therapy at outset, and only treat infected patients. The value to clinicians and patients includes improved patient outcomes, reduced antibiotic resistance, and improved antibiotic stewardship. AST workflow in cartridge is shown in FIG. 36.

A streamlined FISH method for MultiPath ID/AST was developed. Key competitive advantage vs. other rapid AST methods is provided. The test has detection of specific pathogens after differential growth, and rapid AST for non-sterile & polymicrobial infections. The result is a streamlined classical fluorescent in situ hybridization (FISH). Comparison of Traditional FISH to MultiPath FISH is shown in FIG. 37.

The UTI ID/AST Test determines if the patient does not have a UTI (<10K total CFU/mL urine), if the patient is infected by one of 4 most common UTI pathogens, and which of 4 primary antibiotics are effective. Workflow includes adding urine directly to cartridge containing growth medium. If positive for one of the UTI pathogens, reflexes to AST. The time to result goal: ID in 30 minutes, AST in 4 hours.

Figure 39:
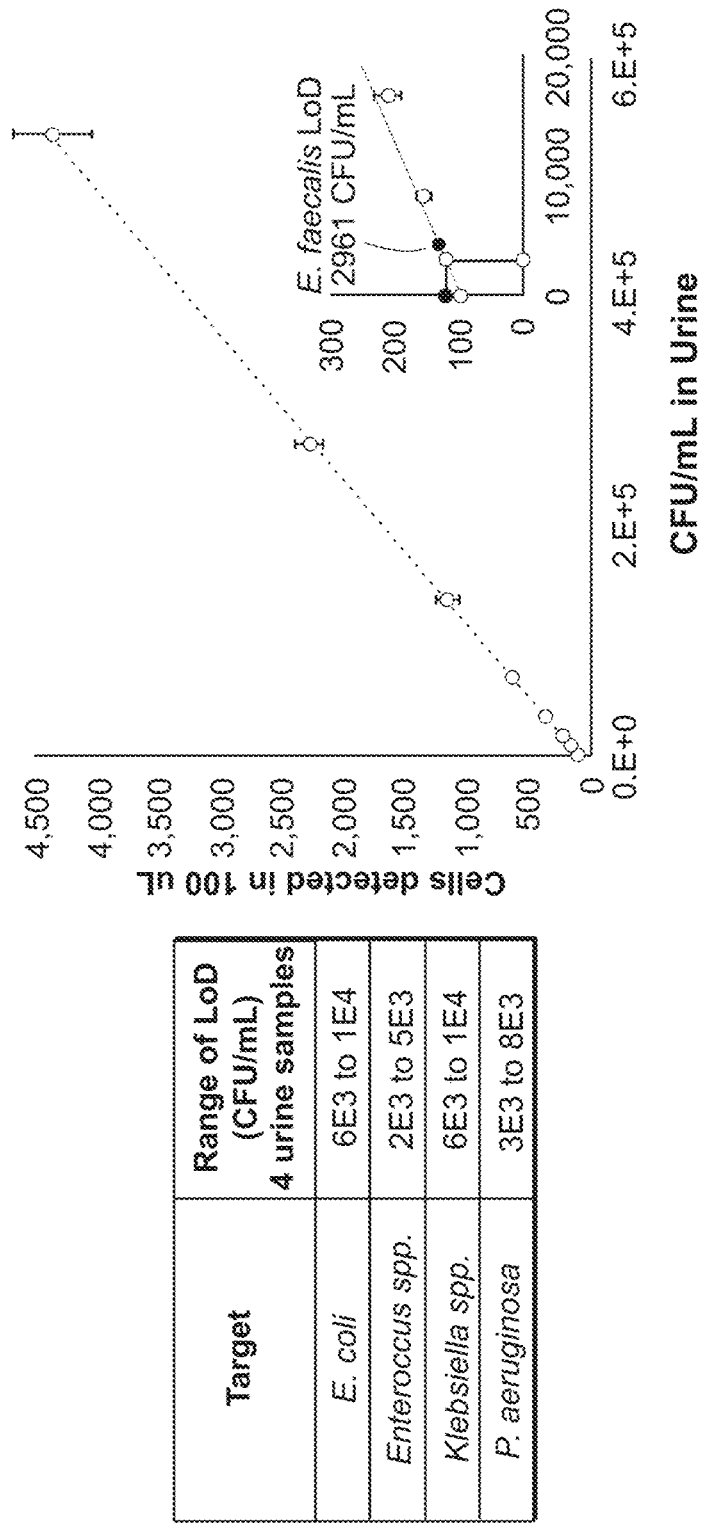
FIG. 39 shows high analytical sensitivity for UTI pathogens.

The UTI ID Test: studies in microtiter plates is shown in FIG. 38. FIG. 39 shows high analytical sensitivity for UTI pathogens. The test was 30 minutes, 30% urine spiked with pathogens, and 4 different urine samples were tested. The method detects <10K CFU/ml urine, a common threshold for UTI.

Figure 41:
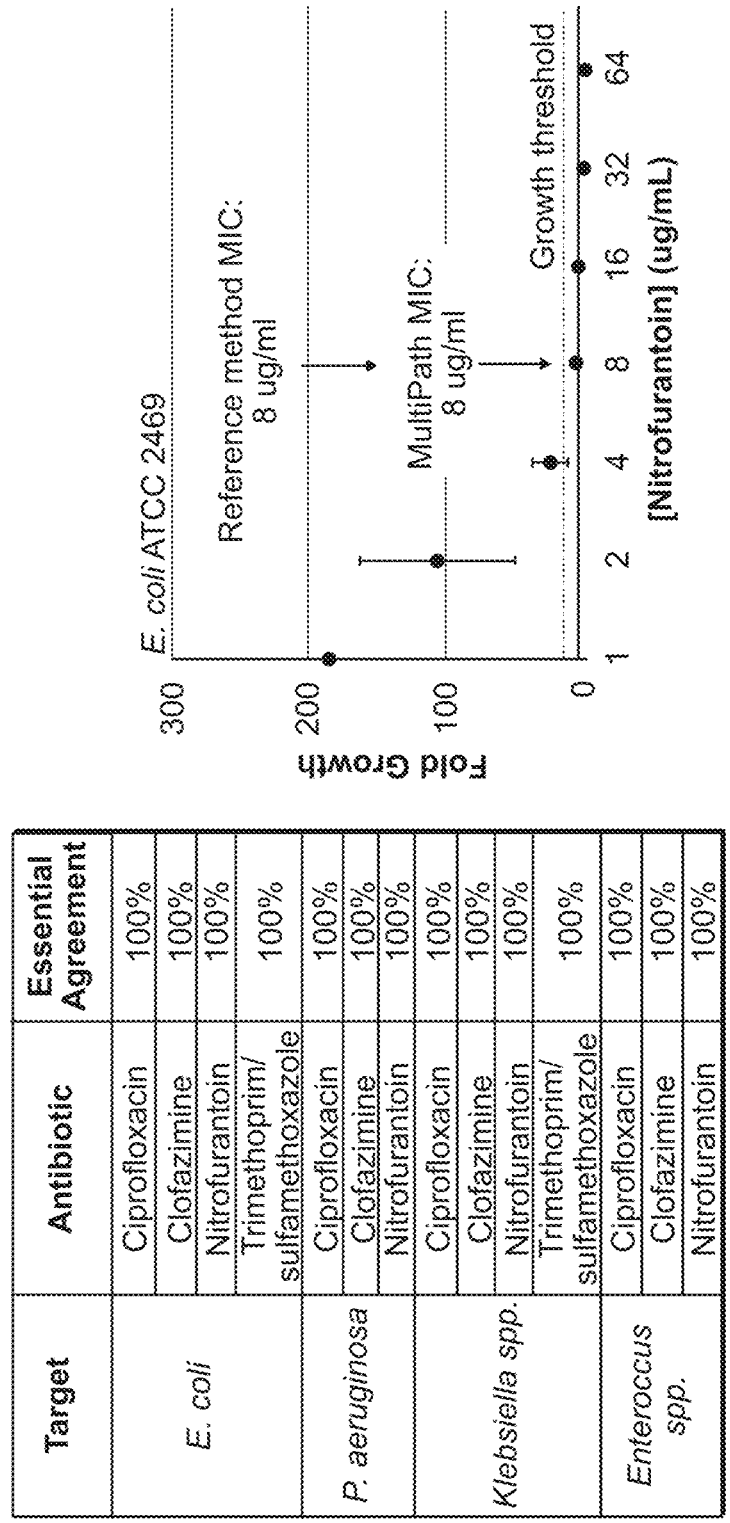
FIG. 41 shows UTI AST accuracy.

The UTI AST Test: studies in microtiter plates is shown in FIG. 40. FIG. 41 shows UTI AST accuracy. The method compared MuitiPath AST (4 hr) to broth microdilution reference test (18 hr). 4 species, 7-10 strains for each, 3-4 Abx were included, with 1 minor error in 200 observations and no Very Major or Major Errors. The MultiPath AST showed high accuracy vs. reference method.

Figure 42:
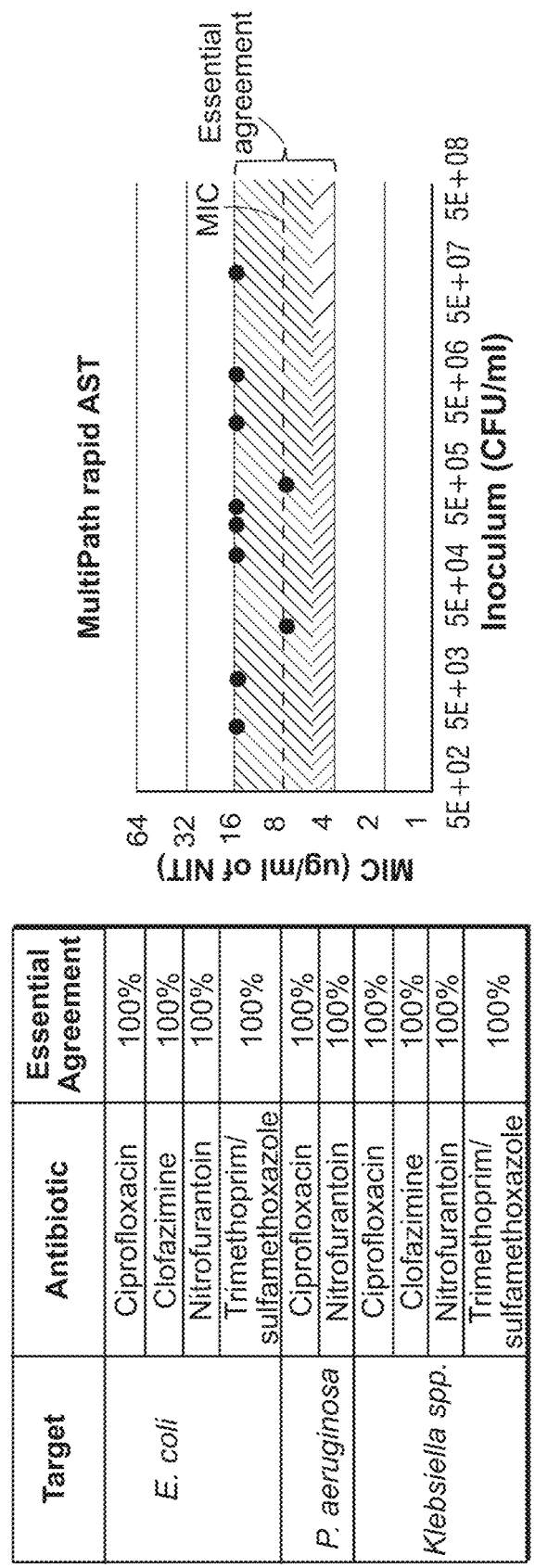
FIG. 42 shows MultiPath rapid AST robustness to variable inoculum levels.

FIG. 42 shows MultiPath rapid AST robustness to variable inoculum levels. The impact on AST of inocula covering 4 orders of magnitude was tested, for 3 species and 4 antibiotics, with 100% essential agreement for all samples. No inoculum effect was seen with inocula covering 4 orders of magnitude.

Figures 43, 44:
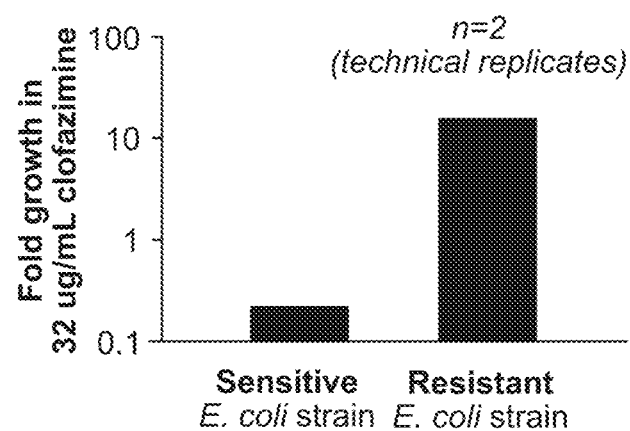
FIG. 43 shows the impact of polymicrobial samples on rapid AST results.
FIG. 44 shows results from the UTI ID/AST.

FIG. 43 shows the impact of polymicrobial samples on rapid AST results. Non-target bacteria added included *Staphylococcus epidermidis, Micrococcus luteus, Corynebacterium minutissimum, Staphylococcus aureus, Acinetobacter baumannii, Citrobacter freundii*, and *Klebsiella pneumoniae* NDM1. Ran MultiPath AST for *E. coli* in the presence of high levels of other bacteria. *E. coli* MIC was compared to reference test for 5 antibiotics. >98% essential agreement compared to reference method for 84 samples tested. *E. coli* MIC for imipenem was unaffected in the presence 1E7 CFU/mL of a carbapenemase secreting *K. pneumoniae* NDM1. Thus, rapid AST results were not impacted by polymicrobial samples.

FIG. 44 shows results from the UTI ID/AST. A resistant and a sensitive *E. coli* strain using ID/AST on Platform were tested. Methods included measuring fold growth after 4 hr incubation in 32 ug/ml clofazimine. The potential for automated rapid MultiPath AST on Platform was shown. FIG. 45 shows Option 1 UTI ID/AST Summary.

LF Test performance across a range of blood samples was explored. Whole blood samples from 54 patients. Each sample was tested both unspiked and spiked with 150 pg/ml LF in the LF assay. All samples were correctly identified as spiked or unspiked with a single exception. Results are shown in Table 12 and Table 13 below. FIG. 46 shows FISH Probe Inclusivity. FIG. 47 shows FISH Probe Exclusivity. 55 strains were tested for cross-reactivity and microbial interference specifications.

TABLE 12

Results

| | | Lethal Factor Added | |
|---|---|---|---|
| | | 150 pg/mL | 0 pg/mL |
| MultiPath ™ Call | Positive | 108 | 1 |
| | Negative | 0 | 107 |
| | Positive Percent Agreement | 100% | |
| | Negative Percent Agreement | 99.1% | |
| | Total Accuracy | 99.5% | |

TABLE 13

| | Conditions |
|---|---|
| | Conditions |
| Sample | Various whole blood |
| n | 54 patient samples |
| | 2 conditions (spiked and unspiked) |
| | 2 data points per cartridge |
| Cartridge | Breadboard |
| Analyzer | Breadboard |

Platform and Workflow

MultiPath Platform may be used. The platform is a bench top, sample-to-answer laboratory instrument (Analyzer). No sample prep or culture/isolation required. Test one sample in one cartridge for organism Identification (ID) or Antibiotic Susceptibility Test (AST) or combinations/variants thereof. Runs approximately 40 patient samples per 8 hour shift. Test Results in approximately ½ hour (ID) and 4 hours (AST). Test menu: expandable, cartridge barcodes contain test and sample identification. Location: physician's office, urgent care, or hospital laboratory. Size: approximately 15" (38 mm) wide, 15" (38 mm) tall, & 24" (61 mm) deep. Power: 120-240 VAC, 50-60 Hz. Computer: internal. Communication: via customer network/LIS or manually via USB port.

Workflow steps include 1) load 1-5 cartridges in removable rack, 2) dispense samples, as specified by test (e.g., blood, urine, stool) into cartridge, with all reagents contained in the cartridge, 3) load rack into Analyzer, 4) use touch screen to initiate run and report results, 5) empty removable waste bin (up to 20 cartridges).

Figure 48:
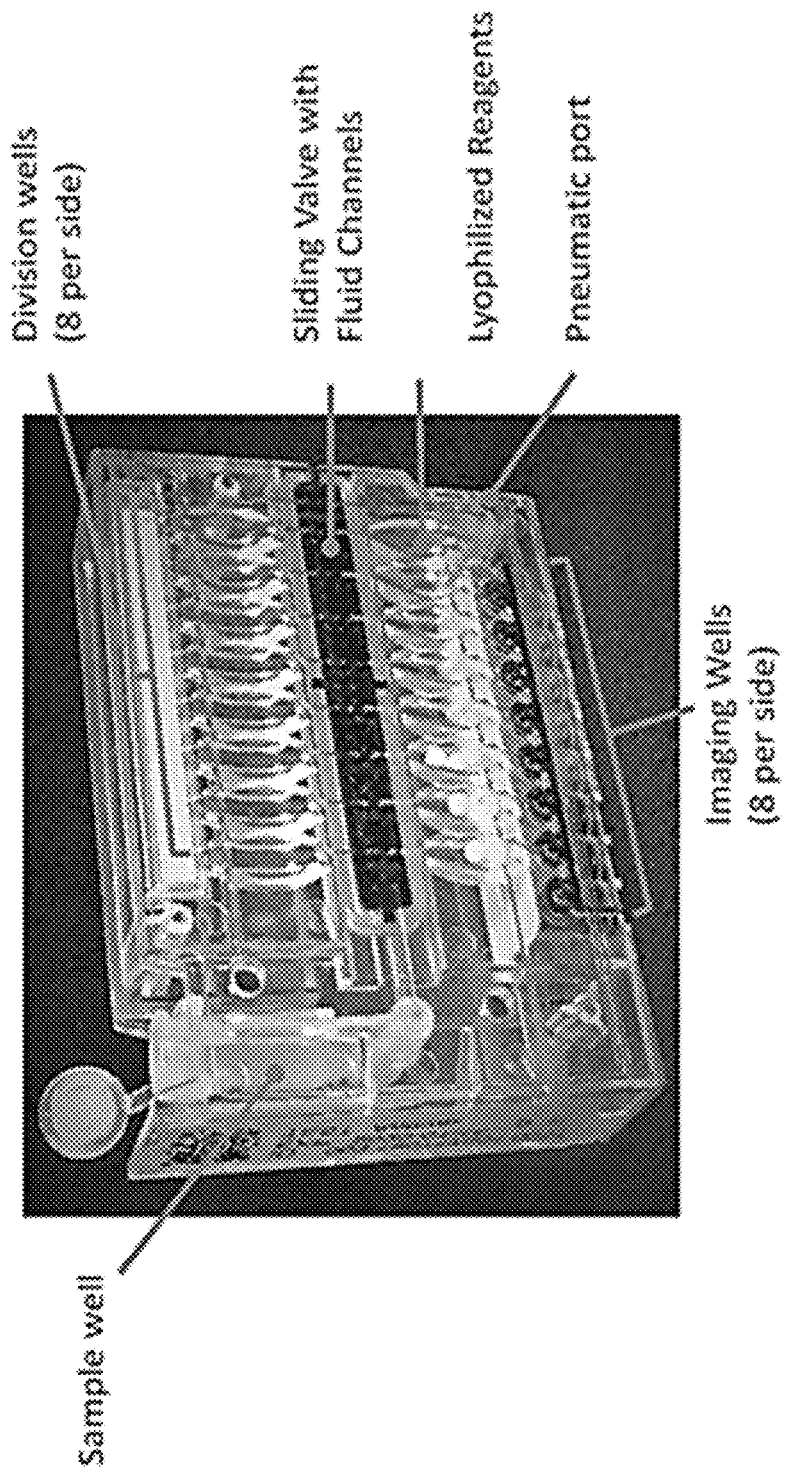
FIG. 48 shows an example platform cartridge.

The Analyzer has a rotating carousal and pusher for transporting and incubating up to 20 cartridges. The Analyzer has an upper compartment for cartridge processing and incubation (such as at 35° C.) and a lower compartment comprising electronics, optics, and pneumatics. An example platform cartridge is shown in FIG. 48. Cartridges contain up to 16 wells, each of which can perform up to 4 assays.

The platform user interface (UI) may report results. The touch screen UI is used to initiate/monitor a run, and to display, print and export test results. After the final imaging of a Cartridge, the Software generates the results & stores all test data in a database. The UI also provides a means for the database to be queried, sorted, and other data management functions. The Software has a Laboratory Information System (LIS) API which can be accessed by the User to automatically upload data to their LIS. The user can configure a local or network printer. The Software has User identification and permission levels to control access.

The invention claimed is:

1. A method for detecting targets comprising:
introducing a biological sample directly to a cassette for analysis;
labeling targets in the sample with a photonic label in a first liquid layer in the cassette; and
separating photonically-labeled targets out of the sample into a second liquid layer within the cassette; and detecting and counting, without magnification, the photonically-labeled targets in the second layer,
wherein the separating step comprises: introducing magnetic particles to the sample to bind to targets; and applying a magnetic field to separate magnetic particle-bound targets from the sample,
wherein the targets are single molecules,
wherein all reagents required for forming the first and second liquid layers and labeling the targets are contained within the cassette to which the biological sample is introduced,
wherein the cassette comprises a channel comprising a neutralization control, wherein the neutralization control comprises detecting and counting targets in a neutralization control sample where neutralization binders are introduced that sequester targets of interest, thereby preventing photonic labeling of the targets.

2. The method of claim 1, wherein the targets are selected from the group consisting of proteins, nucleic acids, carbohydrates, and sugars.

3. The method of claim 1, wherein the photonic signal is fluorescence.

4. The method of claim 1, wherein the photonic label is a fluorescent particle or a fluorophore.

5. The method of claim 1, wherein the targets comprise at least one of toxin A and toxin B of *Clostridium difficile*.

6. The method of claim 1, wherein the targets comprise at least one of toxin A and toxin B of *Clostridium difficile*.

7. The method of claim 1, wherein the targets comprise a biomarker secreted by *Bacillus anthracis* cells.

8. The method of claim 7, wherein the biomarker is Lethal Factor.

9. The method of claim 1, wherein said photonic label is a fluorescent particle.

10. The method of claim 1, wherein the first and second layers have different densities.

11. The method of claim 1, wherein photonic labels comprise fluorescently-labeled antibodies, or fragments thereof, that bind to one or more targets.

12. The method of claim 1, wherein the magnetic particles comprise antibodies that bind to a target of interest.

13. The method of claim of 1, wherein the second liquid layer is a dye-cushion, the dye-cushion comprising: a density agent; and a dye that absorbs light.

14. The method of claim 1, wherein the cassette is pre-loaded with target-specific fluorescent particles and magnetic particles.

15. The method of claim 14, the cassette further comprising: a receiving reservoir into which a user introduces the sample; a dye-cushion and a detection surface provided in an imaging well in fluidic communication with a mixing well; and a plurality of paired imaging well and mixing well sets in parallel to one another.

16. The method of claim 15, the cassette further comprising a filter that filters particulates from the sample.

17. The method of claim 1, wherein the detecting step comprises: detecting and counting targets on a detection surface by observing a photonic signal from the photonically-labeled targets.

18. The method of claim 17, wherein the detecting step further comprises digital imaging.

19. The method of claim 18, wherein the photonic label is a fluorescent particle and the digital imaging comprises illuminating fluorescent particles on the detection surface and detecting the signal emitted from the fluorescent particles on a photoelectric array detector.

20. The method of claim 1, wherein the cassette further comprises a channel comprising reagents to detect the target in the sample.

21. The method of claim 1, wherein the cassette further comprises a channel comprising reagents to detect the target in the sample plus positive control reagents to demonstrate that the target detection in the sample is effective even if the sample does not contain endogenous target.

22. The method of claim 21, wherein the positive control comprises detecting and counting targets in a positive control sample where a known amount of targets of interest is introduced.

23. The method of claim 1, further comprising calculating a ratio of a detection signal from a sample to a signal detected from the neutralization control.

24. The method of claim 23, further comprising determining whether the ratio exceeds a threshold.

25. The method of claim 1, wherein the sample is a human stool sample or is derived from human stool.

* * * * *